United States Patent
Wengner et al.

(10) Patent No.: US 11,712,440 B2
(45) Date of Patent: Aug. 1, 2023

(54) PREDICTIVE MARKERS FOR ATR KINASE INHIBITORS

(71) Applicant: Bayer Aktiengesellschaft, Leverkusen (DE)

(72) Inventors: Antje Margret Wengner, Berlin (DE); Gerhard Siemeister, Berlin (DE); Li Liu, East Hanover, NJ (US)

(73) Assignee: Bayer Aktiengesellschaft, Leverkusen (DE)

( * ) Notice: Subject to any disclaimer, the term of this patent is extended or adjusted under 35 U.S.C. 154(b) by 319 days.

(21) Appl. No.: 16/770,462

(22) PCT Filed: Dec. 4, 2018

(86) PCT No.: PCT/EP2018/083486
§ 371 (c)(1),
(2) Date: Jun. 5, 2020

(87) PCT Pub. No.: WO2019/110586
PCT Pub. Date: Jun. 13, 2019

(65) Prior Publication Data
US 2020/0375997 A1 Dec. 3, 2020

Related U.S. Application Data

(60) Provisional application No. 62/596,356, filed on Dec. 8, 2017.

(51) Int. Cl.
*A61K 31/5377* (2006.01)
*A61P 35/00* (2006.01)
*C12Q 1/6886* (2018.01)

(52) U.S. Cl.
CPC .......... *A61K 31/5377* (2013.01); *A61P 35/00* (2018.01); *C12Q 1/6886* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| WO | WO2012138938 A1 | 10/2012 | | |
|---|---|---|---|---|
| WO | WO2013152298 A1 | 10/2013 | | |
| WO | WO 2016/020320 | * | 2/2016 | .......... C07D 471/04 |
| WO | WO2016020320 A1 | | 2/2016 | |
| WO | WO 2017/121684 | * | 7/2017 | .......... C07D 471/04 |
| WO | WO2017118734 A1 | | 7/2017 | |
| WO | WO2018153968 A1 | | 8/2018 | |

OTHER PUBLICATIONS

Buisson, R. et al. (Sep. 2017) "AAPOBEC3A and APOBEC3B Activities Render Cancer Cells Susceptible to ATR Inhibition," Cancer Res., 77(17):4567-4578.
Hocke, S. et al. (2016) "A synthetic lethal screen identifies ATR-inhibition as a novel therapeutic approach for POLD1-deficient cancers," Oncotarget; 7(6)7080-7095.
International Search Report dated Feb. 11, 2019 for PCT Application No. PCT/EP2018/083486, filed Dec. 4, 2018, 6 pages.

* cited by examiner

*Primary Examiner* — Craig D Ricci
(74) *Attorney, Agent, or Firm* — James G. Dilmore

(57) ABSTRACT

The present invention covers an ATR kinase inhibitor, particularly 2-[(3R)-3-methylmorpholin-4-yl]-4-(1-methyl-1H-pyrazol-5-yl)-8-(H-pyrazol-5-yl)-1,7-naphthyridine ("Compound A"), for use in the treatment of a hyperproliferative disease in a subject, wherein the hyper-proliferative disease or the subject is or has been characterized by one or more biomarker(s), wherein the biomarker(s) comprise(s) a) one or more functional mutations in one or more gene(s)/protein(s) selected from RBBP8, APOBEC3A, APOBEC3B, CLSPN, ERCC, HUS1, MAD2L2, PGBD5, POLD1, RAD1, TIMELESS and/or TIPIN; and/or b) the expression of a fusion gene encoding a fusion protein selected from EWSR-ERG, EWSR1-FLI1, SS18-SSX and/or SS18-SSX2 gene/protein.

3 Claims, No Drawings

Specification includes a Sequence Listing.

PREDICTIVE MARKERS FOR ATR KINASE INHIBITORS

CROSS REFERENCE TO RELATED APPLICATIONS

This application is a national stage application under 35 U.S.C. § 371 of International Application No. PCT/EP2018/083486, filed internationally on Dec. 4, 2018, which claims the benefit of priority to U.S. Provisional Application No. 62/596,356, filed Dec. 8, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: BHC173076 ST25.txt, dated May 11, 2023, having a file size of 247,048 bytes).

The present invention covers an inhibitor of ATR kinase, particularly of 2-[(3R)-3-methylmorpholin-4-yl]-4-(1-methyl-1H-pyrazol-5-yl)-8-(1H-pyrazol-5-yl)-1,7-naphthyridine (in the following called "Compound A") for use in the treatment of a hyper-proliferative disease in a subject, wherein the hyper-proliferative disease or the subject is or has been characterized by one or more biomarker(s), wherein the biomarker(s) comprise(s)
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

BACKGROUND

The integrity of the genome of eukaryotic cells is secured by complex signalling pathways, known as DNA damage response (DDR). Recognition of DNA damage activates DDR pathways resulting in cell cycle arrest, suppression of general translation, induction of DNA repair, and, finally, in cell survival or cell death. Proteins that directly recognize aberrant DNA structures recruit and activate kinases of the DDR pathway, such as ATR. ATR responds to a broad spectrum of DNA damage, including double-strand breaks and lesions derived from interference with DNA replication as well as increased replication stress that is observed in oncogene-driven tumor cells (e.g. Ras mutation/upregulation, Myc upregulation, CyclinE overexpression).

ATR kinase inhibitors are specifically or generically disclosed in the following publications: J. Med. Chem. 2013, 56, 2125-2138; Exp. Rev. Mol. Med. 16, e10, 2014; WO2010054398A1; WO2010071837A1; WO2010073034A1; WO2011143399A1; WO2011143419A1; WO2011143422A1; WO2011143423A2; WO2011143425A2; WO2011143426A1; WO2011154737A1; WO2011163527A1; WO2012138938A1; WO2012178123A1; WO2012178124A1; WO2012178125A1; WO2013049719A1; WO2013049720A1; WO2013049722A1; WO2013049859A1; WO2013071085A1; WO2013071088A1; WO2013071090A1; WO2013071093A1; WO2013071094A1; WO2013152298A1; WO2014062604A1; WO2014089379A1; WO2014143240; WO 2014143241; WO 2014143242; ACS Med. Chem. Lett. 2015. 6, 37-41; ACS Med. Chem. Lett. 2015. 6, 42-46, WO 2015085132, WO 2015187451.

2-[(3R)-3-methylmorpholin-4-yl]-4-(1-methyl-1H-pyrazol-5-yl)-8-(1H-pyrazol-5-yl)-1,7-naphthyridine (in the following called "Compound A") is a new ATR kinase inhibitor, which is described in International Patent Application WO2016020320. Identification of one or more biomarkers that predict sensitivity to Compound A could result in more effective biomarker-driven targeted therapy for hyper-proliferative diseases.

No predictive markers for ATR kinase inhibitors have been identified yet in the clinical setting. However, preclinical evidence suggests a number of candidate predictive biomarkers for ATR kinase inhibitors VE-821, VX-970 and AZD6738: Williamson et al. suggest that ATR kinase inhibitors could have potential as single-agent treatments for ARID1A defective cancers (Nature Communications 7:13837 DOI: 10.1038/ncomms13837, (2016)). According to Mohni et al. ATR pathway inhibition is synthetically lethal in VE-821 treated cancer cells with ERCC1 deficiency and loss of the structure-specific endonuclease ERCC1-XPF (ERCC4) is synthetic lethal with ATR pathway inhibitors (Cancer Res. 74, (2014), 2835-2845). ATR inhibition by VE-821 also seems to synergize with loss of ERCC1, ATM and XRCC1 (Mohni et al., PLOS ONE | DOI:10.1371/journal.pone.0125482 May 12, 2015). According to Hocke et al. (Oncotarget Vol. 7, No. 6, (2016), 7080-7095) POLD1 deficiency might represent a predictive marker for treatment response towards ATR inhibitors. Flynn et al. (Science 347, (2015), 273-277) suggest that ATR kinase inhibitors may be useful for treatment of ALT-positive cancers. According to the data described by Menezes et al. (Mol. Cancer. Res. 13(1), (2015), 120-129) single-agent ATR inhibitors may have therapeutic utility in the treatment of mantle cell lymphoma with ATM loss-of-function. Middleton et al. (Oncotarget, Vol. 6, No. 32, (2015), 32396-32409) suggest that defects in ATM, BRCA2, XRCC3 and XRCC1 and high DNA-PKcs expression conferred sensitivity to VE-821 monotherapy.

According to Jones et al. (Cancer Research (2017), Author Manuscript Published OnlineFirst on Oct. 16, 2017; DOI: 10.1158/0008-5472.CAN-17-2056) in Synovial sarcoma SS18-SSX1 or SS18-SSX2 fusion proteins induce ATR kinase inhibitor sensitivity. Nieto-Soler et al. (Oncotarget. 2016; 7:58759-58767) suggest that expression of EWS-FLI1 (also called EWSR1-FLI1) or EWS-ERG (also called EWSR1-ERG oncogenic translocations sensitizes non-ES cells to ATR inhibitors.

Remi-Buisson et al. (Cancer Res 77(17), (2017), 4567-4578) describe that APOBEC3A and APOBEC3B activities confer susceptibility to ATR kinase inhibitors.

The object of the present invention is to provide one or more biomarker(s) for the treatment of one or more hyper-proliferative disease(s) with an ATR kinase inhibitor, particularly with Compound A, as described herein, in a subject.

DETAILED DESCRIPTION OF THE INVENTION

Definitions of Terms Used in the Context of the Present Invention

The term "ATR kinase inhibitor" or the term "inhibitor of ATR kinase" as used herein means any compound that inhibits ATR kinase. Examples of ATR kinase inhibitors which may be used in context with the present invention include VX-803, VX-970, AZD-6738 and preferably Compound A (described infra), particularly Compound A.

In context with the present invention the term "VX-803" means 2-amino-6-fluoro-N-[5-fluoro-4-(4-{[4-(oxetan-3-yl)piperazin-1-yl]carbonyl}piperidin-1-yl)pyridin-3-yl]pyrazolo[1,5-a]pyrimidine-3-carboxamide. VX-803 has the following structure

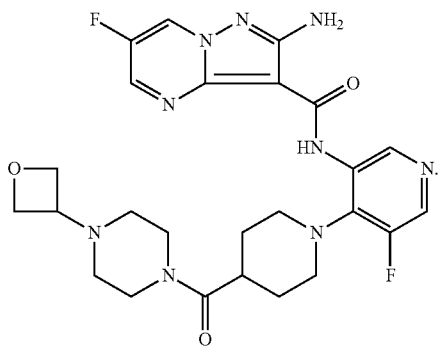 [SMILES: Nc1nn2cc(F)cnc2c1C(=O)Nc1cncc(F)c1N1CCC(C(=O)N2CCN(C3COC3)CC2)CC1]

In context with the present invention the term "VX-970" means 3-(3-{4-[(methylamino)methyl]phenyl}-1,2-oxazol-5-yl)-5-[4-(propan-2-ylsulfonyl)phenyl]pyrazin-2-amine. VX-970 has the structure

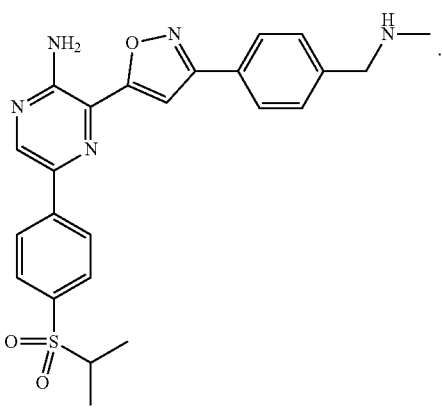 [SMILES: CNCc1ccc(-c2cc(-c3nc(-c4ccc(S(=O)(=O)C(C)C)cc4)cnc3N)on2)cc1]

In context with the present invention the term "AZD-6738" means 4-{4-[(3R)-3-methylmorpholin-4-yl]-6-[1-(S-methylsulfonimidoyl)cyclopropyl]pyrimidin-2-yl}-1H-pyrrolo[2,3-b]pyridine. AZD-6738 has the structure

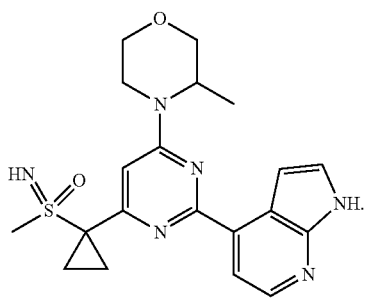 [SMILES: CC1COCCN1c1cc(C2(S(C)(=N)=O)CC2)nc(-c2ccnc3[nH]ccc23)n1]

The term "Compound A" as used herein means 2-[(3R)-3-methylmorpholin-4-yl]-4-(1-methyl-1H-pyrazol-5-yl)-8-(1H-pyrazol-5-yl)-1,7-naphthyridineofstructure:

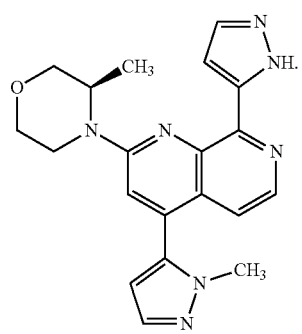

Compound A

The expression "gene/protein" means one gene or one protein. The expression "gene(s)/protein(s)" means one or more gene(s) or one or more protein(s). The expression "gene(s)" means one gene or more genes. The expression "protein(s)" means one protein or more proteins.

The term "hyper-proliferative disease" includes but is not limited, e.g., psoriasis, keloids, and other hyperplasias affecting the skin, benign prostate hyperplasia (BPH), as well as malignant neoplasia. Examples of malignant neoplasia treatable with an ATR kinae inhibitor, particularly Compound A, include solid and hematological tumors. Solid tumors can be exemplified by tumors of the breast, bladder, bone, brain, central and peripheral nervous system, colon, anum, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

Examples of breast cancer include, but are not limited to invasive ductal carcinoma, invasive lobular carcinoma, ductal carcinoma in situ, and lobular carcinoma in situ, particularly with bone metastases. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, urethral and human papillary renal cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

In particular, the present invention covers the treatment of lung cancer, colorectal cancer, cervical cancer, bladder cancer, breast cancer, melanoma, B-cell lymphoma, particularly diffuse large B-cell lymphoma (DLBCL), mantle cell lymphoma, prostate cancer, gliomas, ovarian cancer, glioblastoma, neuroblastoma, chronic lymphocytic leukemia (CLL), fibrosarcoma, gastric cancer, esophageal cancer, pancreatic cancer, chronic and acute myeloid leukemia (CML/AML), acute lymphoblastic leukemia (ALL), Hodgkins disease, multiple myeloma (MM) and T-cell lymphoma, endometrial cancer, vaginal cancer, and vulvar cancer, as well as sarcoma of the uterus.

Preferably, the present invention covers the treatment of prostate cancer, B-cell lymphoma, particularly diffuse large B-cell lymphoma (DLBCL), mantle cell lymphoma, melanoma, particularly malignant melanoma, ovarian, particularly, ovarian adenocarcinoma, colorectal cancer, lung, particularly non-small cell lung carcinoma, cervical cancer, and breast cancer, particularly triple-negative mammary carcinoma, pancreatic cancer, fibrosarcoma.

The term "biomarker(s)" as used herein means one or more biomarker(s), wherein the biomarker(s) comprise(s)
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

Particularly, the term biomarker(s) as used herein means one or more biomarker(s), wherein the biomarker comprise(s)
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

A preferred biomarker of the present invention is RBBP8 gene/protein, which is characterized by one or more deleterious mutation(s).

The term "functional mutation" as used herein means a mutation of a gene which results in an altered function of the gene, its corresponding RNA or its corresponding protein compared to the function of the respective wildtype gene, corresponding wildtype RNA or corresponding wildtype protein.

The term "altered function" as used herein means either reduced or increased function of the gene, its corresponding RNA or its corresponding protein compared to the function of the respective wildtype gene, corresponding wildtype RNA or corresponding wildtype protein. The term "altered function" also includes the complete loss of the function or the gain of a new function of the gene, its corresponding RNA or its corresponding protein compared to the function of the respective wildtype gene, corresponding wildtype RNA or corresponding wildtype protein.

The functional mutation of the gene/protein can be a "deleterious mutation" or an "activating mutation".

The term "deleterious mutation" as used herein means a mutation of the gene which has a deleterious effect on the function of said gene, its corresponding RNA or its corresponding protein compared to the function of the respective wildtype gene/RNA/protein. For example, the deleterious mutation of the gene may result in a reduced gene expression level of said gene, a reduced amount or a reduced activity of the protein corresponding to said gene, or it may result in a nonfunctional gene/protein ("loss-of-function") compared to the respective wildtype gene/protein.

Examples of a deleterious mutation include but are not limited to the following: The deleterious mutation can be a nonsense mutation, which is a point mutation in the respective gene, resulting in a premature stop codon, or a nonsense codon in the transcribed mRNA, and in a truncated, incomplete, and nonfunctional protein corresponding to the respective gene.

The deleterious mutation can be a missense mutation, which is a point mutation in the respective gene, resulting in the production either of a nonfunctional protein (complete loss of function) or in a protein with partial loss of function compared to the respective wildtype protein.

The deleterious mutation can also result in a frameshift mutation, which is a genetic mutation in the respective gene caused by insertions or deletions of one or more nucleotides in such gene, wherein the number of nucleotides is not divisible by three, and resulting in a (sometimes truncated) nonfunctional protein corresponding to the respective gene.

The deleterious mutation can also be a large rearrangement mutation, for example a deletion of one or more exons disrupting the reading frame or a critical functional domain of the corresponding protein. Another example for a large rearrangement mutation is a duplication of one or more non-terminal exons disrupting the reading frame or a critical functional domain of the corresponding protein.

The deleterious mutation can also be a splice site mutation, which is a genetic mutation that inserts, deletes or changes a number of nucleotides in the specific site at which splicing takes place during the processing of precursor messenger RNA into mature messenger RNA. Splice site consensus sequences that drive exon recognition are located at the very termini of introns. The deletion of the splicing site results in one or more introns remaining in mature mRNA thereby resulting in the production of a nonfunctional protein corresponding to the respective gene.

The deleterious mutation can also be a copy number variant (CNV), particularly a decrease of the gene copy number (e.g. a homozygous or heterozygous deletion) compared to the normal gene copy number of the respective wildtype gene.

The term "activating mutation" as used herein means a mutation of the gene which changes said gene, its corresponding RNA and/or its corresponding protein in such a way, that its effects (e.g. the amount of corresponding RNA/protein, or the protein activity) get stronger compared to the respective wildtype gene/RNA/protein. The term "activating mutation" also includes a mutation of a gene, in which the protein corresponding to said gene gets a new function compared to the function of the corresponding wildtype protein. Examples of activating mutations include but are not limited to the following: The activating mutation can be a substitution of one amino acid residue by another that confers a new or higher activity upon the protein. The activating mutation can be a copy number variant (CNV), particularly an increase of the gene copy number compared to the normal gene copy number of the respective gene.

The activating mutation can also be a fusion gene or fusion protein, e.g. occurring as a result of translocation, interstitial deletion or chromosomal inversion.

The respective wildtype gene is characterized by a reference nucleotide sequence of the cDNA of said gene, which is described under SEQ ID Nos 1 to 7 and SEQ ID Nos 15 to 19, particularly by the coding sequence of said cDNA described under SEQ ID Nos 1 to 7 and SEQ ID Nos 15 to 19. The reference amino acid sequence of the respective wildtype protein is described under SEQ ID Nos 8 to 14 and SEQ ID Nos 20 to 24.

The term "stratification method" as used herein means the method by which one or more of the functional mutation(s) as defined herein, particularly of the deleterious mutations, the activating mutations and/or the expression of the fusion-proteins is (are) determined. Preferably, the stratification method is an in-vitro method. Examples of stratification methods, which can be used in context with the present inventions, are described infra.

The term "sample" as used herein means the sample from the subject, preferably an in vitro sample, which is used in the stratification method (as defined herein), e.g. a sample of tumor cells or of tumor tissue, a blood sample, particularly a sample of tumor tissue containing tumor cells.

The term "therapeutically effective amount" of an inhibitor of ATR kinase, particularly of Compound A means an amount of said compound, or a pharmaceutically acceptable salt, isomer, polymorph, metabolite, hydrate, solvate or ester thereof, which is effective to treat the hyperproliferative disease.

Aspects of the Present Invention:
Use(s) of the Present Invention

The present invention covers an inhibitor of ATR kinase, particularly 2-[(3R)-3-methylmorpholin-4-yl]-4-(1-methyl-1H-pyrazol-5-yl)-8-(1H-pyrazol-5-yl)-1,7-naphthyridine (in the following called "Compound A") or a tautomer, an N-oxide, a hydrate, a solvate, or a pharmaceutically acceptable salt thereof, particularly Compound A, for use in the treatment of a hyper-proliferative disease in a subject, wherein the hyper-proliferative disease or the subject is or has been characterized by one or more biomarker(s), wherein the biomarker(s) comprise(s)
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

The present invention also covers an inhibitor of ATR kinase, particularly 2-[(3R)-3-methylmorpholin-4-yl]-4-(1-methyl-1H-pyrazol-5-yl)-8-(1H-pyrazol-5-yl)-1,7-naphthyridine (in the following called "Compound A") or a tautomer, an N-oxide, a hydrate, a solvate, or a pharmaceutically acceptable salt thereof, particularly Compound A, for use in a method of treating a hyper-proliferative disease in a subject, wherein the hyper-proliferative disease or the subject is or has been characterized by one or more biomarker(s), wherein the biomarker(s) comprise(s)
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

In another embodiment of the use of the present invention the hyper-proliferative disease or the subject is or has been characterized by one or more biomarker(s), wherein the biomarker(s) comprise(s)
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

In another embodiment of the use of the present invention the hyper-proliferative disease or the subject is or has been characterized by one or more biomarker(s), wherein the biomarker(s) comprise(s) one or more deleterious mutation(s) in one or more gene(s)/protein(s) selected from RBBP8, CLSPN, ERCC1, HUS1, MAD2L2, POLD1, RAD1, TIMELESS and/or TIPIN.

In another embodiment of the use of the present invention the hyper-proliferative disease or the subject is or has been characterized by one or more biomarker(s), wherein the biomarker(s) comprise(s) one or more deleterious mutation(s) in RBBP8 gene/protein.

The present invention therefore also covers an inhibitor of ATR kinase, particularly Compound A, or a tautomer, an N-oxide, a hydrate, a solvate, or a pharmaceutically acceptable salt thereof, preferably Compound A, for use in the treatment of a hyper-proliferative disease in a subject, wherein said subject or hyper-proliferative disease is or has been characterized by one or more deleterious mutation(s) in the RBBP8 gene/protein.

In another embodiment of the use of the present invention the hyper-proliferative disease or the subject is or has been characterized by one or more biomarker(s), wherein the biomarker(s) comprise(s) one or more activating mutation(s) in one or more gene(s)/protein(s) selected from APOBEC3A, APOBEC3B and/or PGBD5.

In another embodiment of the use of the present invention the hyper-proliferative disease or the subject is or has been characterized by one or more biomarker(s), wherein the biomarker(s) comprise(s) the expression of a fusion protein selected from EWSR1-ERG, EWSR1-FLI1, SS18-SSX1 and/or SS18-SSX2.

In another embodiment of the present invention the subject or the hyper-proliferative disease is or has been characterized by one or more biomarker(s), wherein the biomarker(s) comprise(s) one or more deleterious mutation(s) in TP53 gene/protein and one or more deleterious mutation(s) in one or more gene(s)/protein(s) selected from RBBP8, CLSPN, ERCC1, HUS1, MAD2L2, POLD1, RAD1, TIMELESS and/or TIPIN.

In another embodiment of the present invention the subject or the hyper-proliferative disease is or has been characterized by one or more biomarker(s), wherein the biomarker(s) comprise(s) one or more deleterious mutation(s) in TP53 gene/protein and one or more deleterious mutation(s) in RBBP8 gene/protein.

In another embodiment of the present invention the subject or the hyper-proliferative disease is or has been characterized by one or more biomarker(s) comprising one or more functional mutation(s) of the gene(s)/protein(s), particularly deleterious and/or activating mutations, as described in Table 1 and/or in Table 2 infra.

TABLE 1

Deleterious mutations-examples

| Gene | Short insertions/ deletions (INDELs) | Substitution- Nonsense | Copy Number Variant (CNV) |
|---|---|---|---|
| RBBP8 | | | decrease of the gene copy number |
| ERCC1 | | | decrease of the gene copy number |
| HUS1 | | | decrease of the gene copy number |
| POLD1 | c337delG, p.P116fs*53 | c.733G>T, p.E245* | decrease of the gene copy number |

TABLE 2

Activating mutations-examples

| Gene | Alteration |
|---|---|
| APOBEC3A | Increase of gene copy number/upregulation of gene/ protein expression |
| APOBEC3B | Increase of gene copy number/upregulation of gene/ protein expression |
| PGBD5 | Increase of gene copy number/upregulation of gene/ protein expression |

Further examples of deleterious/activating mutations of the gene(s) mentioned herein are described in publically available databases, such as e.g. ClinVar (Landrum M J, Lee J M, Riley G R, et al., "ClinVar: public archive of relationships among sequence variation and human phenotype", Nucleic Acids Res. 2014; 42:D980-5; https://www.ncbi.nlm.nih.gov/clinvar), HGMD (the Human Gene Mutation Database, http://www.hgmd.cf.ac.uk/ac/index.php; Stenson P D, Mort M, Ball E V, et al., "The human gene mutation database: 2008 update.", Genome Med. 2009; 1:13) or in "The Human Variome Project" (http://www.humanvariomeproject.org; Timothy D Smith and Mauno Vihinen, "Standard development at the Human Variome Project", Database 2015, 2015), which has curated a gene-/disease-specific databases to collect the sequence variants and genes associated with diseases.

Further examples of deleterious/activating mutations of the gene(s), which may be used in context with the method(s)/use(s)/kit(s)/pharmaceutical composition(s) of the present invention, are described in COSMIC database (www.cancer.sanger.ac.uk; "COSMIC: exploring the world's knowledge of somatic mutations in human cancer", Forbes et al., Nucleic Acids Res. 2015, January; 43 (Database issue):D805-11. doi: 10.1093/nar/gku1075. Epub 2014 Oct. 29), particularly in release 79 of COSMIC (COSMIC v79), which was released on 14 Nov. 2016.

Examples of EWSR1-ERG fusion gene/protein, which may be used as biomarkers in context with the method(s)/use(s)/kit(s)/pharmaceutical composition(s) of the present invention, are described for example in Sorensen et al. (Nature Genetics 6(2), (1994), 146-151), Dockhorn-Dworniczak et al. (Klinische Padiatrie 209(4), (1997), 156-164), Giovannini et al. (The Journal of Clinical Investigation 94(2), 489-496), Peter et al. (International Journal of Cancer 67(3), (1996), 339-342) and Bielack et al. (The New England Journal of Medicine 350(13), (2004), 1364-1365).

Examples of EWSR1-FLI1 fusion gene/protein, which may be used as biomarkers in context with the method(s)/use(s)/kit(s)/pharmaceutical composition(s) of the present invention, are described for example in Delattre et al. (Nature 359, (1992), 162-165), Zucman et al. (The EMBO Journal 12(12), (1993), 4481-4487), Giovannini et al. (The Journal of Clinical Investigation 94(2), 489-496), Dockhorn-Dworniczak et al. (Klinische Padiatrie 209(4), (1997), 156-164), Zoubek et al. (British Journal of Cancer 70(5), (1994), 908-913), de Alava et al. (Journal of Clinical Oncology 16(4), (1998), 1248-1255) and van Doorninc et al. (Journal of Clinical Oncology 28(12), (2010), 1989-1994).

Examples of SS18-SSX1 fusion gene/protein, which may be used as biomarkers in context with the method(s)/use(s)/kit(s)/pharmaceutical composition(s) of the present invention, are described for example in Nilsson et al. (Cancer research; 59(13); 1999; 3180-4), Amary et al. (Histopathology; 51(4); 2007; 559-61), O'Sullivan et al. (The Journal of molecular diagnostics: JMD; 4(3); 2002; 178-80), Wei Y et al. (Oncogene; 22(14); 2003; 2215-22), Crew et al. (The EMBO journal; 14(10); 1995; 2333-40), Safar et al. (Diagnostic molecular pathology: the American journal of surgical pathology, part B; 7(5); 1998; 283-7), Sanders et al. (Molecular diagnosis: a journal devoted to the understanding of human disease through the clinical application of molecular biology; 4(1); 1999; 65-70), Panagopoulos et al. (Genes, chromosomes & cancer; 31(4); 2001; 362-72) and de Leeuw et al. (Human molecular genetics; 4(6); 1995; 1097-9).

Examples of SS18-SSX2 fusion gene/protein, which may be used as biomarkers in context with the method(s)/use(s)/kit(s)/pharmaceutical composition(s) of the present invention, are described for example in Nilsson et al. (Cancer research; 59(13); 1999; 3180-4), Wei et al. (Oncogene; 22(14); 2003; 2215-22), Crew et al. (The EMBO journal; 14(10); 1995; 2333-40), Otsuka et al. (Cancer genetics and cytogenetics; 167(1); 2006; 82-8), Fligman et al. (The American journal of pathology; 147(6); 1995; 1592-9) and Panagopoulos et al. (Genes, chromosomes & cancer; 31(4); 2001; 362-72).

In another embodiment of the present invention the subject or the hyper-proliferative disease is characterized by one or more biomarker(s) comprising the expression of a fusion gene encoding a fusion protein selected from EWSR1-ERG, EWSR-FLI1, SS18-SSX1 and/or SS18-SSX2 fusion gene/protein, particularly fusion genes and their corresponding fusion proteins described in Table 3 infra.

TABLE 3

Fusion genes encoding fusion proteins - examples

| | 5' Partner Gene | | | | 3' Partner Gene | | |
|---|---|---|---|---|---|---|---|
| Gene Name | Last Observed Exon | Inferred Breakpoint | Inserted Sequence | Gene Name | First Observed Exon | Inferred Breakpoint | Inserted Sequence |
| EWSR1 | 7 | 1112 | — | ERG | 8 | 967 | — |
| EWSR1 | 7 | 1112 | — | ERG | 11 | 1141 | — |
| EWSR1 | 7 | 1112 | — | ERG | 9 | 1036 | — |
| EWSR1 | 10 | 1364 | — | ERG | 8 | 967 | — |
| EWSR1 | 7 | 1112 | — | ERG | 10 | 1093 | — |
| EWSR1 | 7 | 1112 | — | FLI1 | 6 | 920 | — |
| EWSR1 | 7 | 1112 | — | FLI1 | 5 | 854 | — |
| EWSR1 | 10 | 1364 | — | FLI1 | 6 | 920 | — |
| EWSR1 | 10 | 1364 | — | FLI1 | 5 | 854 | — |
| EWSR1 | 7 | 1112 | — | FLI1 | 8 | 1046 | — |
| EWSR1 | 7 | 1112 | — | FLI1 | 7 | 986 | — |
| EWSR1 | 10 | 1364 | — | FLI1 | 8 | 1046 | — |
| EWSR1 | 9 | 1331 | — | FLI1 | 4 | 650 | — |
| EWSR1 | 9 | 1331 | — | FLI1 | 7 | 986 | — |
| EWSR1 | 7 | 1112 | — | FLI1 | 9 | 1094 | — |
| EWSR1 | 10 | 1364 | — | FLI1 | 7 | 986 | — |
| EWSR1 | 8 | 1293 | — | FLI1 | 7 | 986 | — |
| EWSR1 | 8 | 1293 | — | FLI1 | 6 | 920 | — |
| SS18 | 10 | 1286 | — | SSX1 | 6 | 467 | — |
| SS18 | 10 | 1286 | — | SSX1 | 5 | 417 | — |
| SS18 | 10 | 1286 | — | SSX1 | 6 | 467-103 | — |
| SS18 | 10 | 1286 + 8793 | — | SSX1 | 6 | 467-? | — |
| SS18 | 9 | 1152 | — | SSX1 | 4 | 321 | — |
| SS18 | 10 | 1286 + 1941 | — | SSX1 | 6 | 467-1313 | — |
| SSX1 | 5 | 466 + 575 | — | SS18 | 11 | 1287-12019 | — |
| SS18 | 9 | 1152 | — | SSX1 | 5 | 417 | — |
| SS18 | 10 | 1286 | 6 bp insertion (Sanders et al., (1999), supra) | SSX1 | 4 | 321 | — |

In another embodiment of the present invention the subject or the hyper-proliferative disease is or has been characterized by one or more biomarker(s) selected from one or more functional mutation(s) of the gene(s)/protein(s) which are described in the Experimental Section infra.

In another embodiment the subject or the hyper-proliferative disease is or has been characterized by one or more biomarker(s), wherein the biomarker comprise(s) one or more functional mutation(s), particularly deleterious mutation(s), of the RBBP8 gene/protein. A reference nucleotide sequence of the cDNA of the wildtype RBBP8 gene (having no deleterious mutation) is described under SEQ ID No. 1. A reference amino acid sequence of the wildtype RBBP8 protein is described under SEQ ID No. 8.

In another embodiment the subject or the hyper-proliferative disease is or has been characterized by one or more biomarker(s), wherein the biomarker comprise(s) one or more functional mutation(s), particularly activating mutation(s), of the APOBEC3A gene/protein. A reference nucleotide sequence of the cDNA of the wildtype APOBEC3A gene (having no activating mutation) is described under SEQ ID No. 2. A reference amino acid sequence of the wildtype APOBEC3A protein is described under SEQ ID No. 9.

In another embodiment the subject or the hyper-proliferative disease is or has been characterized by one or more biomarker(s), wherein the biomarker comprise(s) one or more functional mutation(s), particularly activating mutation(s), of the APOBEC3B gene/protein. A reference nucleotide sequence of the cDNA of the wildtype APOBEC3B gene (having no activating mutation) is described under SEQ ID No. 3. A reference amino acid sequence of the wildtype APOBEC3A protein is described under SEQ ID No. 10.

In another embodiment the subject or the hyper-proliferative disease is or has been characterized by one or more biomarker(s), wherein the biomarker comprise(s) one or more functional mutation(s), particularly deleterious mutation(s), of the CLSPN gene/protein. A reference nucleotide sequence of the cDNA of the wildtype CLSPN gene (having no deleterious mutation) is described under SEQ ID No. 15. A reference amino acid sequence of the wildtype CLSPN protein is described under SEQ ID No. 20.

In another embodiment the subject or the hyper-proliferative disease is or has been characterized by one or more biomarker(s), wherein the biomarker comprise(s) one or more functional mutation(s), particularly deleterious mutation(s), of the ERCC1 gene/protein. A reference nucleotide sequence of the cDNA of the wildtype ERCC1 gene (having no deleterious mutation) is described under SEQ ID No. 4. A reference amino acid sequence of the wildtype wildtype ERCC1 protein is described under SEQ ID No. 11.

In another embodiment the subject or the hyper-proliferative disease is or has been characterized by one or more biomarker(s), wherein the biomarker comprise(s) one or more functional mutation(s), particularly deleterious mutation(s), of the HUS1 gene/protein. A reference nucleotide sequence of the cDNA of the wildtype HUS1 gene (having no deleterious mutation) is described under SEQ ID No. 5. A reference amino acid sequence of the wildtype HUS1 protein is described under SEQ ID No. 12.

In another embodiment the subject or the hyper-proliferative disease is or has been characterized by one or more biomarker(s), wherein the biomarker comprise(s) one or more functional mutation(s), particularly deleterious mutation(s), of the MAD2L2 gene/protein. A reference nucleotide sequence of the cDNA of the wildtype MAD2L2 gene (having no deleterious mutation) is described under SEQ ID No. 16. A reference amino acid sequence of the wildtype MAD2L2 protein is described under SEQ ID No. 21.

In another embodiment the subject or the hyper-proliferative disease is or has been characterized by one or more biomarker(s), wherein the biomarker comprise(s) one or more functional mutation(s), particularly activating mutation(s), of the PGBD5 gene/protein. A reference nucleotide sequence of the cDNA of the wildtype PGBD5 gene (having no activating mutation) is described under SEQ ID No. 6. A reference amino acid sequence of the wildtype PGBD5 protein is described under SEQ ID No. 13.

In another embodiment the subject or the hyper-proliferative disease is or has been characterized by one or more biomarker(s), wherein the biomarker comprise(s) one or more functional mutation(s), particularly deleterious mutation(s), of the POLD1 gene/protein. A reference nucleotide sequence of the cDNA of the wildtype POLD1 gene (having no deleterious mutation) is described under SEQ ID No. 7. A reference amino acid sequence of the wildtype POLD1 protein is described under SEQ ID No. 14.

In another embodiment the subject or the hyper-proliferative disease is or has been characterized by one or more biomarker(s), wherein the biomarker comprise(s) one or more functional mutation(s), particularly deleterious mutation(s), of the RAD1 gene/protein. A reference nucleotide sequence of the cDNA of the wildtype RAD1 gene (having no deleterious mutation) is described under SEQ ID No. 17. A reference amino acid sequence of the wildtype RAD1 protein is described under SEQ ID No. 22.

In another embodiment the subject or the hyper-proliferative disease is or has been characterized by one or more biomarker(s), wherein the biomarker comprise(s) one or more functional mutation(s), particularly deleterious mutation(s), of the TIMELESS gene/protein. A reference nucleotide sequence of the cDNA of the wildtype TIMELESS gene (having no deleterious mutation) is described under SEQ ID No. 18. A reference amino acid sequence of the wildtype TIMELESS protein is described under SEQ ID No. 23.

In another embodiment the subject or the hyper-proliferative disease is or has been characterized by one or more biomarker(s), wherein the biomarker comprise(s) one or more functional mutation(s), particularly deleterious mutation(s), of the TIPIN gene/protein. A reference nucleotide sequence of the cDNA of the wildtype TIPIN gene (having no deleterious mutation) is described under SEQ ID No. 19. A reference amino acid sequence of the wildtype TIPIN protein is described under SEQ ID No. 24.

In another embodiment the subject or the hyper-proliferative disease is or has been characterized by one or more biomarker(s), wherein the biomarker comprise(s) the expression of a EWSR1-ERG fusion gene encoding a EWSR1-ERG fusion protein.

In another embodiment the subject or the hyper-proliferative disease is or has been characterized by one or more biomarker(s), wherein the biomarker comprise(s) the expression of a EWSR1-FLI1 fusion gene encoding a EWSR1-FLI1 fusion protein.

In another embodiment the subject or the hyper-proliferative disease is or has been characterized by one or more biomarker(s), wherein the biomarker comprise(s) the expression of a SS18-SSX1 fusion gene encoding a SS18-SSX1 fusion protein.

In another embodiment the subject or the hyper-proliferative disease is or has been characterized by one or more biomarker(s), wherein the biomarker comprise(s) the expression of a SS18-SSX2 fusion gene encoding a SS18-SSX2 fusion protein.

In another embodiment of the use of the present invention a therapeutically effective amount of an inhibitor of ATR kinase, particularly of Compound A, is administered to the subject.

The present invention also covers an inhibitor of ATR kinase, particularly Compound A, for use in a method of treating a hyper-proliferative disease in a subject, said method comprising the steps:
a) determining or having determined if one or more of the biomarker(s) defined herein are present in a sample, preferably in an in vitro sample, of the subject;
b) administering a therapeutically effective amount of an inhibitor of ATR kinase, particularly Compound A to the subject, if one or more of the biomarker(s) determined by or according to step a) is (are) present in the sample.

The present invention also covers an inhibitor of ATR kinase, particularly Compound A for use in a method of treating a hyper-proliferative disease in a subject said method comprising the steps:
a) determining or having determined if one or more of the biomarker(s) selected from
  (i) one or more functional mutation(s) in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
  (ii) the expression of a fusion gene encoding a fusion protein selected from EWSR1-ERG, EWSR1-FLI1, SS18-SSX1 and/or SS18-SSX2 gene/protein;
  are present in a sample, preferably in an in vitro sample, of the subject;
b) administering a therapeutically effective amount of an inhibitor of ATR kinase, particularly Compound A to the subject, if one or more of the biomarker(s) determined by or according to any one of steps a)(i) and/or a)(ii) is (are) present in the sample.

The present invention also covers an inhibitor of ATR kinase, particularly Compound A, for use in a method of treating a hyper-proliferative disease in a subject said method comprising the steps:
a) determining or having determined if one or more of the biomarker(s) selected from one or more functional mutation(s) in one or more gene(s)/protein(s) selected from RBBP8 is (are) present in a sample, preferably in an in vitro sample, of the subject;
b) administering a therapeutically effective amount of an inhibitor of ATR kinase, particularly of Compound A, to the subject, if one or more of the biomarker(s) determined by or according to step a) is (are) present in the sample.

The present invention also covers an inhibitor of ATR kinase, particularly Compound A, for use in a method of treating a hyper-proliferative disease in a subject said method comprising the steps:
a) determining or having determined if the biomarker(s) comprising one or more deleterious mutation(s) in RBBP8 gene/protein are present in a sample, preferably in an in vitro sample, of the subject;
b) administering a therapeutically effective amount of an inhibitor of ATR kinase, particularly of Compound A, to the subject, if the biomarker(s) determined by or according to step a) is (are) present in the sample.

In another embodiment of the use of an inhibitor of ATR kinase, particularly Compound A, in a method of treating a hyper-proliferative disease in a subject according to the present invention said method comprising the steps:
a) assaying or having assayed a sample, preferably an in vitro sample, from the subject, particularly by one or more of the stratification method(s) described herein;
b) determining or having determined if one or more of the biomarker(s) defined herein are present in the sample;
c) administering a therapeutically effective amount of an inhibitor of ATR kinase, particularly of Compound A, to the subject, if one or more of the biomarker(s) determined by or according to step
b) is (are) present in the sample.

In another embodiment the present invention covers the use of an inhibitor of ATR kinase, particularly Compound A, in a method of treating a hyper-proliferative disease in a subject said method comprising the steps:
a) assaying or having assayed a sample, preferably an in vitro sample, from the subject, particularly by one or more of the stratification method(s) described herein;
b) determining or having determined if one or more of the biomarker(s) defined in (i) and/or (ii) are present in the sample:
 (i) one or more functional mutation(s) in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN gene/protein; and/or
 (ii) the expression of a fusion gene encoding a fusion protein selected from EWSR1-ERG, EWSR1-FLI1, SS18-SSX1 and/or SS18-SSX2 gene/protein;
c) administering a therapeutically effective amount of an inhibitor of ATR kinase, particularly of Compound A, to the subject, if one or more of the biomarker(s) determined by or according to any one of steps (b)(i) and/or (b)(ii) is (are) present in the sample.

In another embodiment the present invention covers an inhibitor of ATR kinase, particularly Compound A for use in a method of treating a hyper-proliferative disease in a subject, wherein said subject is or has been selected by having one or more biomarker(s) defined herein.

In another embodiment the present invention covers an inhibitor of ATR kinase, particularly Compound A, for use in a method of treating a hyper-proliferative disease in a subject, wherein said subject is or has been selected by having one or more of the biomarker(s) selected from
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN and/or
b) the expression of a fusion gene encoding a fusion protein selected from EWSR1-ERG, EWSR1-FLI1, SS18-SSX1 and/or SS18-SSX2 gene/protein.

In another embodiment the present invention covers an inhibitor of ATR kinase, particularly Compound A, for use in a method of treating a hyper-proliferative disease in a subject, wherein said subject is or has been selected by having one or more of the biomarker(s) selected from one or more functional mutations in one or more gene(s)/protein(s) selected from RBBP8.

The present invention also covers an inhibitor of ATR kinase, particularly Compound A, for use in a method of treating a hyper-proliferative disease in a subject, wherein said hyper-proliferative disease is or has been characterized by
a) one or more functional mutation(s) in one or more gene(s)/protein(s) as defined herein; and/or b) the expression of a fusion gene encoding a fusion protein selected from EWSR1-ERG, EWSR1-FLI1, SS18-SSX1 and/or SS18-SSX2 gene/protein.

In another embodiment the present invention also covers an inhibitor of ATR kinase, particularly Compound A, for the use in a method of treating a subject diagnosed with a hyper-proliferative disease, said method comprising the steps:
a) assaying or having assayed a sample, preferably an in vitro sample, from the subject, particularly by one or more of the stratification method(s) described herein;
b) determining or having determined if one or more of the biomarker(s) defined herein are present in the sample;
c) administering a therapeutically effective amount of an inhibitor of ATR kinase, particularly of Compound A, to the subject, if one or more of the biomarker(s) determined by or according to step b) is (are) present in the sample.

In another embodiment the present invention also covers an inhibitor of ATR kinase, particularly Compound A, for the use in a method of treating a subject diagnosed with a hyper-proliferative disease, said method comprising the steps:
a) assaying or having assayed a sample, preferably an in vitro sample, from the subject, particularly by one or more of the stratification method(s) described herein;
b) determining or having determined if one or more biomarker(s) comprising one or more deleterious mutation(s) in RBBP8 gene/protein is (are) present in the sample;
c) administering a therapeutically effective amount of an inhibitor of ATR kinase, particularly of Compound A, to the subject, if one or more of the biomarker(s) determined by or according to step b) is (are) present in the sample.

In another embodiment the present invention covers the use of an inhibitor of ATR kinase, particularly of Compound A, for the preparation of a medicament for treating a hyper-proliferative disease in a subject, wherein said subject or said hyper-proliferative disease is or has been characterized by one or more biomarker(s) defined herein.

In another embodiment the present invention covers the use of an inhibitor of ATR kinase, particularly of Compound A, for the preparation of a medicament for treating a hyper-proliferative disease in a subject, wherein said subject or said hyper-proliferative disease is or has been characterized by one or more biomarker(s) comprising one or more deleterious mutation(s) in RBBP8 gene/protein.

In another embodiment of the use of an inhibitor of ATR kinase, particularly of Compound A, in the manufacture of a medicament for treating a hyper-proliferative disease in a subject according to the invention the one or more functional mutation(s) and/or the expression of a fusion gene is (are) determined or has (have) been determined by one or more of the stratification method(s) described herein.

In another embodiment the present invention covers the use of an inhibitor of ATR kinase, particularly of Compound A, in the manufacture of a medicament for a method of treating a hyper-proliferative disease in a subject, said method comprising the steps:
a) assaying or having assayed a sample from the subject for the presence of the biomarker(s) defined herein, particularly by one or more of the stratification method(s) described herein;
b) determining or having determined if one or more of the biomarker(s) defined herein are present in the sample;
c) administering a therapeutically effective amount of an inhibitor of ATR kinase, particularly of Compound A, to the subject, if one or more of the biomarker(s) determined by or according to step (b) is (are) present in the sample.

In another embodiment the present invention covers the use of an inhibitor of ATR kinase, particularly of Compound A, in the manufacture of a medicament for a method of treating a hyper-proliferative disease in a subject, said method comprising the steps:
a) determining or having determined if one or more of the biomarker(s) defined herein are present in a sample of said subject;
b) administering a therapeutically effective amount of an inhibitor of ATR kinase, particularly of Compound A, to the subject, if one or more of the biomarker(s) determined by or according to step a) is (are) determined positively.

In another embodiment the present invention covers the use of an inhibitor of ATR kinase, particularly of Compound A, in the manufacture of a medicament for a method of treating a hyper-proliferative disease in a subject, said method comprising the steps:
a) determining or having determined if one or more of the biomarker(s) comprising one or more deleterious mutation(s) of the RBBP8 gene/protein are present in a sample of said subject;
b) administering a therapeutically effective amount of an inhibitor of ATR kinase, particularly of Compound A, to the subject, if one or more of the biomarker(s) determined by or according to step a) is (are) present in the sample.

Method(s) of the Present Invention

In another embodiment the present invention covers a method for the treatment of a hyper-proliferative disease in a subject using an effective amount of an inhibitor of ATR kinase, particularly of Compound A, wherein said subject or said hyper-proliferative disease is or has been characterized by one or more biomarker(s) defined herein.

In another embodiment the present invention covers a method for the treatment of a hyper-proliferative disease in a subject using an effective amount of an inhibitor of ATR kinase, particularly of Compound A, wherein said subject is or has been characterized by
a) one or more functional mutation(s) in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

In another embodiment the present invention covers a method for the treatment of a hyper-proliferative disease in a subject using an effective amount of an inhibitor of ATR kinase, particularly of Compound A, wherein said subject is or has been characterized by
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

In another embodiment the present invention covers a method for the treatment of a hyper-proliferative disease in a subject using an effective amount of an inhibitor of ATR kinase, particularly of Compound A, wherein said hyper-proliferative disease or subject is or has been characterized by one or more biomarker(s) comprising one or more deleterious mutation(s) in RBBP8 gene/protein.

In another embodiment of the method for the treatment of a hyper-proliferative disease in a subject using an effective amount of an inhibitor of ATR kinase, particularly of Compound A, the one or more functional mutation(s) and/or the expression of the fusion protein(s) defined herein is (are) or has/have been determined by one or more of the stratification method(s) described herein.

The present invention also covers a method of treatment of a subject diagnosed with a hyper-proliferative disease comprising the steps
a) assaying or having assayed a sample from the subject, preferably an in vitro sample from the subject, particularly by one or more of the stratification method(s) described herein;
b) determining or having determined if one or more of the biomarker(s) defined herein are present in the sample;
c) administering a therapeutically effective amount of an inhibitor of ATR kinase, particularly of Compound A, to the subject, if one or more of the biomarker(s) determined by or according to step b) is (are) present.

The present invention also covers a method of treatment of a subject diagnosed with a hyper-proliferative disease comprising the steps
a) assaying or having assayed a sample from the subject, particularly by one or more of the stratification method(s) described herein;
b) determining or having determined if one or more of the biomarker(s) defined in (i), (ii) and/or (iii) are present in the sample:
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein;
c) administering a therapeutically effective amount of an inhibitor of ATR kinase, particularly of Compound A, to the subject, if one or more of the biomarker(s) determined by or according to any one of steps (b)(i), (b)(ii) and/or (b)(iii) is (are) present in the sample.

The present invention also covers a method of treatment of a hyper-proliferative disease characterized by one or more biomarker(s) in a subject comprising administering a therapeutically effective amount of an inhibitor of ATR kinase, particularly of Compound A, to the subject, wherein the one or more biomarker(s) comprise(s)
a) one or more functional mutation(s) in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

The present invention also covers a method of treatment of a hyper-proliferative disease characterized by one or more biomarker(s) in a subject comprising administering a therapeutically effective amount of an inhibitor of ATR kinase, particularly of Compound A, to the subject, wherein the one or more biomarker(s) comprise(s)

a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

The present invention also covers a method of treatment of a hyper-proliferative disease characterized by one or more biomarker(s) in a subject comprising administering a therapeutically effective amount of an inhibitor of ATR kinase, particularly of Compound A, to the subject, wherein the one or more biomarker(s) comprise(s) one or more deleterious mutation(s) in RBBP8 gene/protein.

The present invention also covers a method of treatment of a hyper-proliferative disease in a subject comprising:
a) determining or having determined that said hyper-proliferative disease of said subject is characterized by one or more biomarker(s), wherein the one or more biomarker(s) comprise(s)
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein; and
b) administering a therapeutically effective amount of an inhibitor of ATR kinase, particularly of Compound A, to said subject.

The present invention also covers a method of treatment of a hyper-proliferative disease in a subject comprising:
a) determining or having determined that said hyper-proliferative disease of said subject is characterized by one or more biomarker(s), wherein the one or more biomarker(s) comprise(s) one or more deleterious mutation(s) in RBBP8 gene/protein; and
b) administering a therapeutically effective amount of an inhibitor of ATR kinase, particularly of Compound A, to said subject.

The present invention also concerns a method for identifying a subject having a hyper-proliferative disease disposed to respond favorably to an inhibitor of ATR kinase, particularly to Compound A, wherein the method comprises the detection of one or more of the biomarker(s) defined herein in a sample of said subject. Preferably the detection of one or more biomarker(s) is performed in vitro, particularly in a sample of tumor cells, tumor tissue or blood.

The present invention also concerns a method for identifying a subject having a hyper-proliferative disease disposed to respond favorably to an inhibitor of ATR kinase, particularly to Compound A, wherein the method comprises the detection of one or more of the biomarker(s) selected from:
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein; in a sample of said subject.

Preferably the detection of one or more biomarker(s) is performed in vitro, particularly in a sample of tumor cells, tumor tissue or blood.

The present invention also concerns a method for identifying a subject having a hyper-proliferative disease disposed to respond favorably to Compound A, wherein the method comprises the detection of one or more of the biomarker(s) comprising one or more deleterious mutation(s) in RBBP8 gene/protein.

In another embodiment the one or biomarker(s) defined herein is (are) or has/have been determined by one or more of the stratification method(s) described herein.

The present invention also concerns a method for identifying a subject with a hyper-proliferative disease who is more likely to respond to a therapy comprising an inhibitor of ATR kinase, particularly Compound A, than other subjects, the method comprising
a) determining or having determined in a sample from said subject one or more of the biomarker(s) defined herein;
b) identifying those subjects for whom in step a) one or more of the biomarker(s) is (are) present in the sample.

The present invention also concerns a method for identifying a subject with a hyper-proliferative disease who is more likely to respond to a therapy comprising an inhibitor of ATR kinase, particularly Compound A, than other subjects, the method comprising
a) determining or having determined in a sample from said subject the biomarker(s) selected from:
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein;
b) identifying those subjects for whom one or more of the biomarker(s) of any one of a)(i), a)(ii) or a)(iii) is (are) present in the sample.

The present invention also concerns a method for identifying a subject with a hyper-proliferative disease who is more likely to respond to a therapy comprising an inhibitor of ATR kinase, particularly Compound A, than other subjects, the method comprising
a) determining or having determined in a sample from said subject one or more of the biomarker(s) comprising one or more deleterious mutation(s) in RBBP8 gene/protein;
b) identifying those subjects for whom in step a) one or more of the biomarker(s) is (are) present in the sample.

Preferably the determination of one or more biomarker(s) is performed in vitro, particularly in a sample of said subject selected from tumor cells, tumor tissue or blood.

The present invention also concerns a method of determining whether a subject having a hyper-proliferative disease will respond to the treatment with an inhibitor of ATR kinase, particularly with Compound A, wherein the method comprises the detection of one or more of the biomarker(s) defined herein in a sample of said subject. Preferably the sample is a sample of tumor cells or of tumor tissue of said subject. Particularly, the biomarker(s) is (are) or has/have been determined by one or more of the stratification method(s) described herein.

The present invention also concerns a method of determining the likelihood that a subject with a hyper-proliferative disease benefits from treatment with an inhibitor of ATR kinase, particularly with Compound A, the method comprising the detection of one or more of the biomarker(s) defined herein in a sample of said subject and identifying the subject being more likely to respond to said treatment with Compound A when the one or more biomarker(s) is (are) present in the sample.

The present invention also covers a method of predicting whether a subject with a hyper-proliferative disease will respond to the treatment with an inhibitor of ATR kinase, particularly with Compound A, wherein the method comprises the detection of one or more of the biomarker(s) defined herein in a sample of said subject.

The present invention also covers a method of predicting whether a subject with a hyper-proliferative disease will respond to the treatment with an inhibitor of ATR kinase, particularly with Compound A, wherein the method comprises the detection of one or more of the biomarker(s) selected from
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein;
in a sample of said subject.

Preferably the detection of one or more biomarker(s) is performed in vitro, particularly in a sample of said subject selected from tumor cells, tumor tissue or blood.

The present invention also covers a method of diagnosing a subject with a hyper-proliferative disease as being disposed to respond favorably to an inhibitor of ATR kinase, particularly to Compound A, comprising:
a) detecting or having detected if one or more of the biomarker(s) defined in (i), (ii) and/or (iii) are present in the sample:
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein; and
b) diagnosing the subject to respond favourably to Compound A when the one or more of the biomarker(s) detected in step a) are present in the sample.

Preferably the measurement of one or more biomarker(s) is performed in vitro, particularly in a sample of said subject selected from tumor cells, tumor tissue or blood.

The present invention also covers a method of treating a subject with a hyper-proliferative disease, wherein the subject is disposed to respond favorably to an inhibitor of ATR kinase, particularly to Compound A, comprising:
a) detecting or having detected if one or more of the biomarker(s) (i), (ii) and/or (iii) are present in the sample:
  (i) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
  (ii) one or more activating mutation(s) in one or more gene(s)/protein(s) selected from APOBEC3A, APOBEC3B and/or PGBD5; and/or
  (iii) the expression of a fusion gene encoding a fusion protein selected from EWSR1-ERG, EWSR1-FLI1, SS18-SSX1 and/or SS18-SSX2 gene/protein;
b) diagnosing or having diagnosed the subject to respond favourably to Compound A when the one or more of the biomarker(s) detected in step a) are present in the sample; and
c) treating the diagnosed subject with 2-[(3R)-3-methylmorpholin-4-yl]-4-(1-methyl-1H-pyrazol-5-yl)-8-(1H-pyrazol-5-yl)-1,7-naphthyridine or a tautomer, an N-oxide, a hydrate, a solvate, or a pharmaceutically acceptable salt thereof.

The present invention also covers the use of one or more of the biomarker(s) defined herein for identifying a subject with a hyper-proliferative disease who is disposed to respond favorably to an inhibitor of ATR kinase, particularly to Compound A.

Kit(s) and Pharmaceutical Composition(s) of the Present Invention

The present invention also covers a kit comprising an inhibitor of ATR kinase, particularly Compound A, together with means, preferably a detecting agent, to detect in a sample from a subject one or more of the biomarker(s) comprising:
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

The present invention also covers a kit comprising an inhibitor of ATR kinase, particularly Compound A, together with means, preferably a detecting agent, to detect, particularly in a sample from a subject, one or more of the biomarker(s) defined herein.

The present invention also covers a kit comprising an inhibitor of ATR kinase, particularly Compound A, together with means, preferably a detecting agent, to detect, particularly in a sample from a subject, one or more of the biomarker(s) comprising one or more deleterious mutation(s) in one or more gene(s)/protein(s) selected from RBBP8, CLSPN, ERCC1, HUS1, MAD2L2, POLD1, RAD1, TIMELESS and/or TIPIN.

The present invention also covers a kit comprising an inhibitor of ATR kinase, particularly Compound A, together with means, preferably a detecting agent, to detect in a sample from a subject one or more of the biomarker(s) comprising one or more deleterious mutation(s) in RBBP8 gene/protein.

The present invention also covers a kit comprising an inhibitor of ATR kinase, particularly Compound A, together with means, preferably a detecting agent, to detect, particularly in a sample from a subject, one or more of the biomarker(s) comprising one or more activating mutation(s) in one or more gene(s)/protein(s) selected from APOBEC3A, APOBEC3B and/or PGBD5.

The present invention further covers the use of pharmaceutical compositions which comprise an inhibitor of ATR kinase, particularly Compound A, together with one or more, preferably inert, nontoxic, pharmaceutically suitable excipients, for use in any of the method(s)/use(s) for treating a hyper-proliferative disease in a subject comprising one or more of the biomarker(s) described herein.

The present invention further covers the use of pharmaceutical compositions which comprise an inhibitor of ATR kinase, particularly Compound A, together with one or more, preferably inert, nontoxic, pharmaceutically suitable excipients, for use in any of the method(s)/use(s) for the treatment of a hyper-proliferative disease in a subject comprising one or more of the biomarker(s) described herein.

Biomarker(s) of the Hyper-Proliferative-Disease or Subject

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s)
a) one or more functional mutations in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein.

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s)
a) one or more deleterious mutation(s) in one or more gene(s)/protein(s) selected from RBBP8, CLSPN, ERCC1, HUS1, MAD2L2, POLD1, RAD1, TIMELESS and/or TIPIN; and/or
b) one or more activating mutation(s) in one or more gene(s)/protein(s) selected from APOBEC3A, APOBEC3B and/or PGBD5; and/or
c) the expression of a fusion gene encoding a fusion protein selected from EWSR1-ERG, EWSR1-FLI1, SS18-SSX1 and/or SS18-SSX2 gene/protein.

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s) one or more deleterious mutation(s) in one or more gene(s)/protein(s) selected from RBBP8, CLSPN, ERCC1, HUS1, MAD2L2, POLD1, RAD1, TIMELESS and/or TIPIN.

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s) one or more activating mutation(s) in one or more gene(s)/protein(s) selected from APOBEC3A, APOBEC3B and PGBD5.

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s) the expression of a fusion gene encoding a fusion protein selected from EWSR1-ERG, EWSR1-FLI1, SS18-SSX1 and/or SS18-SSX2 gene/protein.

In another embodiment of the use(s)/method(s)/pharmaceutical composition(s)/kit(s) of the invention described herein the hyper-proliferative disease or the subject is or has been characterized by one or more biomarker(s), wherein the biomarker(s) comprise(s) one or more deleterious mutation(s) in RBBP8 gene/protein.

In another embodiment of the use/method/pharmaceutical composition/kit of the invention described herein the hyper-proliferative disease or the subject is or has been characterized by one or more biomarker(s), wherein the biomarker(s) comprise(s) one or more deleterious mutation(s) in TP53 gene/protein and one or more deleterious mutation(s) in one or more gene(s)/protein(s) selected from RBBP8, CLSPN, ERCC1, HUS1, MAD2L2, POLD1, RAD1, TIMELESS and/or TIPIN.

In another embodiment of the use/method/pharmaceutical composition/kit of the invention described herein the hyper-proliferative disease or the subject is or has been characterized by one or more biomarker(s), wherein the biomarker(s) comprise(s) one or more deleterious mutation(s) in TP53 gene/protein and one or more deleterious mutation(s) in RBBP8 gene/protein.

In another embodiment of the use/method/pharmaceutical composition/kit of the invention described herein the hyper-proliferative disease or the subject is or has been characterized by one or more biomarker(s), wherein the biomarker(s) comprise(s) one or more deleterious mutation(s) in TP53 gene/protein and one or more activating mutation(s) in one or more gene(s)/protein(s) selected from APOBEC3A, APOBEC3B and/or PGBD5.

In another embodiment of the use/method/pharmaceutical composition/kit of the invention described herein the hyper-proliferative disease or the subject is or has been characterized by one or more biomarker(s), wherein the biomarker(s) comprise(s) one or more deleterious mutation(s) in TP53 gene/protein and the expression of a fusion gene encoding a fusion protein selected from EWSR1-ERG, EWSR1-FLI1, SS18-SSX1 and/or SS18-SSX2 gene/protein.

Compound A can act systemically and/or locally. For this purpose, it can be administered in a suitable manner, for example by the oral, parenteral, pulmonal, nasal, sublingual, lingual, buccal, rectal, dermal, transdermal, conjunctival, otic route, or as an implant or stent. Compound A can be administered in administration forms suitable for these administration routes.

Suitable administration forms for oral administration are those which deliver Compound A in a rapid and/or modified manner, and contain Compound A in crystalline and/or amorphous and/or dissolved form, for example tablets (uncoated or coated tablets, for example with enteric or retarded-dissolution or insoluble coatings which control the release of Compound A, tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardial, intraspinal or intralumbal route) or with inclusion of an absorption (for example by an intramuscular, subcutaneous, intracutaneous, percutaneous or intraperitoneal route). Suitable administration forms for parenteral administration include injection and infusion formulations in the form of solutions, suspensions, emulsions, lyophilizates or sterile powders.

For the other administration routes, suitable examples are pharmaceutical forms for inhalation or inhalation medicaments (including powder inhalers, nebulizers), nasal drops, solutions or sprays; tablets, films/wafers or capsules for lingual, sublingual or buccal administration, films/wafers or capsules, suppositories, ear or eye preparations (for example eye baths, ocular insert, ear drops, ear powders, ear-rinses, ear tampons), vaginal capsules, aqueous suspensions (lotions, shaking mixtures), lipophilic suspensions, ointments, creams, transdermal therapeutic systems (for example patches), milk, pastes, foams, dusting powders, implants, intrauterine coils, vaginal rings or stents.

Compound A can be converted to the administration forms mentioned. This can be done in a manner known per se, by mixing with pharmaceutically suitable excipients.

These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

Pharmaceutically acceptable excipients are non-toxic, preferably they are non-toxic and inert.

Pharmaceutically acceptable excipients include, inter alia: fillers and excipients (for example cellulose, microcrystalline cellulose, such as, for example, Avicel®, lactose, mannitol, starch, calcium phosphate such as, for example, DiCafos®),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat)
- solvents (for example water, ethanol, Isopropanol, glycerol, propylene glycol, medium chain-length triglycerides fatty oils, liquid polyethylene glycols, paraffins),
- surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxyethylene fatty acid esters, polyoxyethylene fatty alcohol ethers, glycerol fatty acid esters, poloxamers such as, for example, Pluronic®),
- buffers and also acids and bases (for example phosphates, carbonates, citric acid, acetic acid, hydrochloric acid, sodium hydroxide solution, ammonium carbonate, trometamol, triethanolamine)
- isotonicity agents (for example glucose, sodium chloride),
- adsorbents (for example highly-disperse silicas)
- viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine),
- disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®),
- flow regulators, lubricants, glidant and mould release agents (for example magnesium stearate, stearic acid, talc, highly-disperse silicas such as, for example, Aerosil®),
- coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®),
- capsule materials (for example gelatine, hydroxypropylmethylcellulose),
- synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and block copolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

Based upon standard laboratory techniques known to evaluate compounds useful for the treatment of hyperproliferative diseases by standard toxicity tests and by standard pharmacological assays for the determination of treatment of the conditions identified above in mammals, and by comparison of these results with the results of known active ingredients or medicaments that are used to treat these conditions, the effective dosage of the compounds of this invention can be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 50 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

In spite of this, it may be necessary to deviate from the amounts specified, specifically depending on body weight, administration route, individual behaviour towards the active ingredient, type of formulation, and time or interval of administration. For instance, less than the aforementioned minimum amount may be sufficient in some cases, while the upper limit mentioned has to be exceeded in other cases. In the case of administration of greater amounts, it may be advisable to divide them into several individual doses over the day.

For example, an inhibitor of ATR kinase, particularly Compound A, may be combined with known antihyperproliferative, cytostatic or cytotoxic substances for treatment of cancers. Examples of suitable antihyperproliferative, cytostatic or cytotoxic combination active ingredients include:

131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab axitinib, azacitidine, basiliximab, belotecan, bendamustine, besilesomab, belinostat, bevacizumab, bexarotene, bicalutamide, bisantrene, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, itraconazole, ixabepilone, ixazomib, lanreotide, lansoprazole, lapatinib, Iasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumabpentetreotide, nilotinib, nilutamide, nimorazole, nimotuzumab, nimustine, nintedanib, nitracrine, nivolumab, obinutuzumab, octreotide, ofatumumab, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Stratification Methods

Various stratification methods can be used in context of the present invention to identify
a) one or more functional mutation(s) in one or more gene(s)/protein(s) selected from RBBP8, APOBEC3A, APOBEC3B, CLSPN, ERCC1, HUS1, MAD2L2, PGBD5, POLD1, RAD1, TIMELESS and/or TIPIN; and/or
b) the expression of a fusion gene encoding a fusion protein selected from EWSR1-ERG, EWSR1-FLI1, SS18-SSX1 and/or SS18-SSX2 gene/protein;
in a sample.

Functional Mutation(s)

The determination of functional mutations, particularly of deleterious and activating mutations, of gene(s)/protein(s) is known to the person skilled in the art. Deleterious mutations and activating mutations can be, for example, determined by one or more of the following stratification methods: Next generation sequencing (NGS) (Metzker M L, "Sequencing technologies—the next generation", Nat Rev Genet. 2010; 11:31-46); Sanger sequencing and other first generation sequencing methods (Lilian T. C. Franca, Emanuel Carrilho and Tarso B. L. Kist, A review of DNA sequencing techniques, Quarterly Reviews of Biophysics 35, 2 (2002), pp. 169-200); PCR, particularly multiplex PCR; Fluorescence in situ hybridization (FISH); array comparative genomic hybridization (array CGH); single nucleotide polymorphism microarray (SNP microarrays), in particular to determine copy number variants (CNVs); or immunohistochemistry (IHC), in particular to determine the loss or overexpression of the respective protein.

The term "NGS" does not denote a single technique; rather, it refers to a diverse collection of post-Sanger sequencing technologies developed in the last decade. These methods include sequencing-by-synthesis (Ronaghi M et al., "A sequencing method based on real-time pyrophosphate", Science. 1998; 281:363-365), sequencing-by-ligation (Shendure J et al., "Accurate multiplex polony sequencing of an evolved bacterial genome", Science. 2005; 309:1728-32.16), ion semiconductor sequencing (Rothberg J M et al., "An integrated semiconductor device enabling non-optical genome sequencing.", Nature. 2011; 475:348-52.17), and others.

Bioinformatics approaches are used for detecting and analyzing the sequence variants from NGS data (Teng S, "NGS for Sequence Variants.", Adv Exp Med Biol. 2016; 939:1-20). NGS variant detection consists of quality control (to remove potential artifacts and bias from data), sequence alignment (reads are mapped to positions on a reference genome), and variant calling (which is performed by comparing the aligned reads with known reference sequences to find which segments are different with the reference genomes).

The sequence variants detected from NGS can be classified to single nucleotide variants (SNVs), small insertions and deletions (INDELs), and large structural variants (SVs) based on their sequences in length. SNVs, the most common type of sequence variants, are single DNA basepair differences in individuals. INDELs are defined as small DNA polymorphisms including both insertions and deletions ranging from 1 to 50 bp in length. SVs are large genomic alterations (>50 bp) including unbalanced variants (deletions, insertions, or duplications) and balanced changes (translocations and inversions). Copy number variants (CNVs), a large category of unbalanced SVs, are DNA alterations that result in the abnormal number of copies of particular DNA segments.

Variant analysis includes variant annotation which can be used to determine the effects of sequence variants on genes and proteins and filter the functional important variants from a background of neutral polymorphisms.

Variant association analyses connects the functional important variants with complex diseases or clinical traits. The disease-related casual variants can be identified by combining these approaches. Results of these variant analysis are stored in public databases, such as for example COSMIC (the Catalogue Of Somatic Mutations In Cancer, www.cancer.sanger.ac.uk), ClinVar (Landrum M J, Lee J M, Riley G R, et al., "ClinVar: public archive of relationships among sequence variation and human phenotype.", Nucleic Acids Res. 2014; 42:D980-5), HGMD (Stenson P D, Mort M, Ball E V, et al., "The human gene mutation database: 2008 update.", Genome Med. 2009; 1:13) or "The Human Variome Project" (http://www.humanvariomeproject.org/), which has curated the gene-/disease-specific databases to collect the sequence variants and genes associated with diseases.

As described above, public data bases, relevant literatures and ongoing evidences associated with the recurrence and function of the gene are used to determine the reportable status of an alteration found from NGS data for the genes of interest. Functional mutations can be classified by any one of the following reportable status: deleterious mutation(s) and activation mutation(s).

Expression of a Fusion Gene Encoding a Fusion Protein
EWSR1-ERG, EWSR1-FLI1, SS18-SSX1 and/or SS18-SSX2 fusion genes and their corresponding fusion proteins can be detected by the methods known to the person skilled in the art, which are for example described in Latysheva and Babu, Nucleic Acid Research 44 (10), (2016), 4487-4503), Davare and Tognon (Biol. Cell 107, (2015), 111-129) and Surace et al. (Lab Invest. 84(9), (2004); 1185-92).

EXPERIMENTAL SECTION

Preparation of Compound A

Compound A was prepared according to the procedure described in example 111 of International Patent Application WO2016020320.

Example 1

Treatment of Isogenic DT40 Chicken Lymphoma Cell Lines with Compound A

DT40 cells from isogenic cell lines (see Table 4: Test systems) were seeded in 40 µl of growth medium (RPMI 1640 medium containing stabilized glutamine (#FG1215, Merck/Biochrom), supplemented with 10% fetal calf serum, 1% chicken serum, 100 U/ml penicillin, 100 g/ml streptomycin, 5E-05M ß-mercaptoethanol) at 200 cells/well in 384-well white microtiter plates ((#6007680; Perkin Elmer Life Sciences) and incubated for 24 h at 37° C. Compound A was added using a digital dispenser (Tecan) to the cells in the test plates and incubated continuously for 3 days at 37° C. To determine cell viability (corresponding to cell number) 10 µl/well of CTG solution (Promega Cell Titer Glo solution, #G755B and G756B) was added. After incubation for further 10 min luminescence was measured using a PHERAstar FSX (BMG Labtech) equipment. All measurements were done in quadruplicates. The percentage change of cell viability was calculated by normalization with respect to the luminescence reading (cell number) at the beginning of treatment of cells (a reference plate was measured at the time point of compound application to the measurement plates) and the luminescence reading (cell number) of the untreated control group. Half-maximal growth inhibition (IC$_{50}$) was determined as compound concentration, which was required to achieve 50% inhibition of cellular growth using a 4-parameter fit.

To evaluate the relative cellular sensitivity of the isogenic DT40 cell lines towards Compound A the mean IC$_{50}$ of each mutant cell line was divided by the mean IC$_{50}$ of wild-type cells, and then the quotient was converted into logarithmic scale (base 2). Log$_2$ ratios of ≤−1 or ≥+1, corresponding to a 2-fold change in sensitivity relative to wild-type cells, were considered as particularly relevant.

Results

The activity of Compound A was tested in an isogenic DT40 cell line deficient in the gene RBBP8 (Table 3) derived from DT40 chicken lymphoma cells, which do not express TP53 (Takao et al., Oncogene 1999; 18: 7002-7009). Relative sensitivities against Compound A were calculated for the mutant DT40 cell line versus the parental wild-type DT40 cell line (Table 5). The results indicate that cells deficient in the gene RBBP8 (copy number reduced from 3 to 1) encoding CtIP protein are more than 2-fold more sensitive towards Compound A as compared to wild-type cells. The result demonstrates that deleterious mutations in the RBBP8 gene sensitize tumor cells to treatment with Compound A.

TABLE 4

DT40 isogenic mutant cell lines.
All cell lines were obtained from Kyoto University, Japan.

| Cell line | Gene | Function of deleted (mutated) gene(s), and annotation | Reference |
|---|---|---|---|
| CtIP+/−/− | RBBP8 | Heterozygous knockout of CtIP gene | 1 |
| CtIPs/−/− | RBBP8 | Removal of Top1cc and Top2cc by its endonuclease activity (S322A mutation) | 1 |

1 Nakamura K, Kogame T, Oshiumi H, Shinohara A, Sumitomo Y, Agama K, et al. Collaborative action of Brca1 and CtIP in elimination of covalent modifications from double-strand breaks to facilitate subsequent break repair. PLoS Genet 2010; 6: e1000828.

TABLE 5

Inhibition of proliferation of isogenic DT40 cells by Compound A and relative sensitivities (log$_2$ ratios).

| Cell line | Gene | IC$_{50}$ (M) | log$_2$ (ratio) |
|---|---|---|---|
| Wild-type | | 1.3E−07 | 0.00 |
| CtIP+/−/− | RBBP8 | 3.4E−08 | −1.93 |
| CtIPs/−/− | RBBP8 | 6.8E−08 | −0.93 |

The invention claimed is:

1. A method of treatment of a hyper-proliferative disease in a subject in need thereof comprising:
   a) determining or having determined that said hyper-proliferative disease of said subject is characterized by one or more biomarkers, wherein the one or more biomarkers comprises one or more deleterious mutations in RBBP8 gene/protein; and
   b) administering a therapeutically effective amount of 2-[(3R)-3-methylmorpholin-4-yl]-4-(1-methyl-1H-pyrazol-5-yl)-8-(1H-pyrazol-5-yl)-1,7-naphthyridine or a tautomer, an N-oxide, a hydrate, a solvate, or a pharmaceutically acceptable salt thereof, to said subject;
   wherein the cancer is selected from the group consisting of ovarian cancer and mantle cell lymphoma.

2. The method of treatment according to claim 1, wherein the cancer is ovarian cancer.

3. The method of treatment according to claim 1, wherein the cancer is mantle cell lymphoma.

* * * * *

SEQUENCE LISTING

```
<160> NUMBER OF SEQ ID NOS: 24

<210> SEQ ID NO 1
<211> LENGTH: 3288
<212> TYPE: DNA
<213> ORGANISM: Homo sapiens
<220> FEATURE:
<221> NAME/KEY: misc_feature
<222> LOCATION: (1)..(3288)
<223> OTHER INFORMATION: RBBP8

<400> SEQUENCE: 1
aagtggaact cccgcgtgac gtcgcgcggg ctcccgggcg gggcgggtcc ggccgcctcc      60
gagcccggcc ggcagccccc ggccttaaag cgcgggctgt ccggaggggt cggctttccc     120
accgaggatt tggcactctg gtgagggaaa agggcgaaag agaaaagcga gcagccgtcc     180
tttcacagcc tcagaaagtg ctcgcttccc ttcgggggct ttcgcgaatc ccgaggcaat     240
ctcggaggcg gtatttgacc tgtccaaaga cgacttgata cctctataat gtaacagaaa     300
aggtcagaaa atattaagca agtagaagtg tggagcatat taagcaagat gaacatctcg     360
ggaagcagct gtggaagccc taactctgca gatacatcta gtgactttaa ggacctttgg     420
acaaaactaa aagaatgtca tgatagagaa gtacaaggtt tacaagtaaa agtaaccaag     480
ctaaaacagg aacgaatctt agatgcacaa agactagaag aattcttcac caaaaatcaa     540
cagctgaggg aacagcagaa agtccttcat gaaaccatta agtttttaga agatcggtta     600
agagcaggct tatgtgatcg ctgtgcagta actgaagaac atatgcggaa aaaacagcaa     660
gagtttgaaa atatccggca gcagaatctt aaacttatta cagaacttat gaatgaaagg     720
aatactctac aggaagaaaa taaaaagctt tctgaacaac tccagcagaa aattgagaat     780
gatcaacagc atcaagcagc tgagcttgaa tgtgaggaag acgttattcc agattcaccg     840
ataacagcct tctcattttc tggcgttaac cggctacgaa gaaaggagaa cccccatgtc     900
```

-continued

```
cgatacatag aacaaacaca tactaaattg gagcactctg tgtgtgcaaa tgaaatgaga    960
aaagtttcca agtcttcaac tcatccacaa cataatccta atgaaaatga aattctagta   1020
gctgacactt atgaccaaag tcaatctcca atggccaaag cacatggaac aagcagctat   1080
accccctgata agtcatcttt taatttagct acagttgttg ctgaaacact tggacttggt   1140
gttcaagaag aatctgaaac tcaaggtccc atgagccccc ttggtgatga gctctaccac   1200
tgtctggaag gaaatcacaa gaaacagcct tttgaggaat ctacaagaaa tactgaagat   1260
agtttaagat tttcagattc tacttcaaag actcctcctc aagaagaatt acctactcga   1320
gtgtcatctc ctgtatttgg agctacctct agtatcaaaa gtggtttaga tttgaataca   1380
agtttgtccc cttctctttt acagcctggg aaaaaaaaac atctgaaaac actccctttt   1440
agcaacactt gtatatctag attagaaaaa actagatcaa atctgaaga tagtgcccctt   1500
ttcacacatc acagtcttgg gtctgaagtg aacaagatca ttatccagtc atctaataaa   1560
cagatactta aaataaaaa tataagtgaa tccctaggtg aacagaatag gactgagtac   1620
ggtaaagatt ctaacactga taaacatttg gagcccctga atcattggg aggccgaaca   1680
tccaaaagga agaaaactga ggaagaaagt gaacatgaag taagctgccc ccaagcttct   1740
tttgataaag aaaatgcttt cccttttcca atggataatc agttttccat gaatggagac   1800
tgtgtgatgg ataaacctct ggatctgtct gatcgatttt cagctattca gcgtcaagag   1860
aaaagccaag gaagtgagac ttctaaaaac aaatttaggc aagtgactct ttatgaggct   1920
ttgaagacca ttccaaaggg cttttcctca agccgtaagg cctcagatgg caactgcacg   1980
ttgcccaaag attccccagg ggagccctgt tcacaggaat gcatcatcct tcagcccttg   2040
aataaatgct ctccagacaa taaaccatca ttacaaataa aagaagaaaa tgctgtcttt   2100
aaaattcctc tacgtccacg tgaaagtttg gagactgaga atgttttaga tgacataaag   2160
agtgctggtt ctcatgagcc aataaaaata caaaccaggt cagaccatgg aggatgtgaa   2220
cttgcatcag ttcttcagtt aaatccatgt agaactggta aaataaagtc tctacaaaac   2280
aaccaagatg tatcctttga aaatatccag tggagtatag atccgggagc agacctttct   2340
cagtataaaa tggatgttac tgtaatagat acaaaggatg gcagtcagtc aaaattagga   2400
ggagagacag tggacatgga ctgtacattg gttagtgaaa ccgttctctt aaaaatgaag   2460
aagcaagagc agaagggaga aaaaagttca aatgaagaaa gaaaaatgaa tgatagcttg   2520
gaagatatgt ttgatcggac aacacatgaa gagtatgaat cctgtttggc agacagtttc   2580
tcccaagcag cagatgaaga ggaggaattg tctactgcca caaagaaact acacactcat   2640
ggtgataaac aagacaaagt caagcagaaa gcgtttgtgg agccgtattt taaaggtgat   2700
gaaagagaga ctagcttgca aaattttcct catattgagg tggttcggaa aaaagaggag   2760
agaagaaaac tgcttgggca cacgtgtaag aatgtgaaa tttattatgc agatatgcca   2820
gcagaagaaa gagaaaagaa attggcttcc tgctcaagac accgattccg ctacattcca   2880
cccaacacac cagagaattt tgggaagtt ggttttcctt ccactcagac ttgtatggaa   2940
agaggttata ttaaggaaga tcttgatcct tgtcctcgtc aaaaagacg tcagccttac   3000
aacgcaatat tttctccaaa aggcaaggag cagaagacat agacgttgaa acagaaacag   3060
aaggatgaag gacagttttt tccttcttag ttatttatag ttaaagttgg tactaaacat   3120
tgattttttt gatcttctgt aaatggattt ataaatcagt tttctattga aaatgtttgt   3180
gatattttgc ttttgcacct ttaaaacaat aaggcgcttt cattttgcac tctaacttaa   3240
```
gagtttttac tttatgtagt gatacctaat acaattttga aaatacaa         3288

<210> SEQ ID NO 2
<211> LENGTH: 1444
<212> TYPE: DNA
<213> ORGANISM: Homo sapiens
<220> FEATURE:
<221> NAME/KEY: misc_feature
<222> LOCATION: (1)..(1444)
<223> OTHER INFORMATION: APOBEC3A

<400> SEQUENCE: 2

| | | | | | |
|---|---|---|---|---|---|
| ggagaagggg | tggggcaggg | tatcgctgac | tcagcagctt | ccaggttgct | ctgatgatat | 60 |
| attaaggctc | ctgaatccta | agagaatgtt | ggtgaagatc | ttaacaccac | gccttgagca | 120 |
| agtcgcaaga | gcgggaggac | acagaccagg | aaccgagaag | ggacaagcac | atggaagcca | 180 |
| gcccagcatc | cgggcccaga | cacttgatgg | atccacacat | attcacttcc | aactttaaca | 240 |
| atggcattgg | aaggcataag | acctaccgt | gctacgaagt | ggagcgcctg | acaatggca | 300 |
| cctcggtcaa | gatggaccag | cacaggggct | ttctacacaa | ccaggctaag | aatcttctct | 360 |
| gtggctttta | cggccgccat | gcggagctgc | gcttcttgga | cctggttcct | tctttgcagt | 420 |
| tggacccggc | ccagatctac | agggtcactt | ggttcatctc | ctggagcccc | tgcttctcct | 480 |
| ggggctgtgc | cggggaagtg | cgtgcgttcc | ttcaggagaa | cacacacgtg | agactgcgta | 540 |
| tcttcgctgc | ccgcatctat | gattacgacc | ccctatataa | ggaggcactg | caaatgctgc | 600 |
| gggatgctgg | ggcccaagtc | tccatcatga | cctacgatga | atttaagcac | tgctgggaca | 660 |
| cctttgtgga | ccaccaggga | tgtccctcc | agccctggga | tggactagat | gagcacagcc | 720 |
| aagccctgag | tgggaggctg | cgggccattc | tccagaatca | gggaaactga | aggatgggcc | 780 |
| tcagtctcta | aggaaggcag | agacctgggt | tgagcagcag | aataaaagat | cttcttccaa | 840 |
| gaaatgcaaa | cagaccgttc | accaccatct | ccagctgctc | acagacgcca | gcaaagcagt | 900 |
| atgctcccga | tcaagtagat | tttaaaaaa | tcagagtggg | ccgggcgcgg | tggctcacgc | 960 |
| ctgtaatccc | agcactttgg | aggccaaggc | gggtggatca | cgaggtcagg | agatcgagac | 1020 |
| catcctggct | aacacggtga | aaccctgtct | ctactaaaaa | tacaaaaaat | tagccaggcg | 1080 |
| tggtggcggg | cgcctgtagt | cccagctact | ctggaggctg | aggcaggaga | gtagcgtgaa | 1140 |
| cccgggaggc | agagcttgcg | gtgagccgag | attgcgctac | tgcactccag | cctgggcgac | 1200 |
| agtaccagac | tccatctcaa | aaaaaaaaa | accagactga | attaatttta | actgaaaatt | 1260 |
| tctcttatgt | tccaagtaca | caatagtaag | attatgctca | atattctcag | aataattttc | 1320 |
| aatgtattaa | tgaaatgaaa | tgataatttg | gcttcatatc | tagactaaca | caaaattaag | 1380 |
| aatcttccat | aattgctttt | gctcagtaac | tgtgtcatga | attgcaagag | tttccacaaa | 1440 |
| cact | | | | | | 1444 |

<210> SEQ ID NO 3
<211> LENGTH: 1533
<212> TYPE: DNA
<213> ORGANISM: Homo sapiens
<220> FEATURE:
<221> NAME/KEY: misc_feature
<222> LOCATION: (1)..(1533)
<223> OTHER INFORMATION: APOBEC3B

<400> SEQUENCE: 3

| | | | | | |
|---|---|---|---|---|---|
| caaaaaaaga | gcgggacagg | gacaagcgta | tctaagaggc | tgaacatgaa | tccacagatc | 60 |
| agaaatccga | tggagcggat | gtatcgagac | acattctacg | acaactttga | aaacgaaccc | 120 |

| | | | |
|---|---|---|---|
| atcctctatg | gtcggagcta | cacttggctg tgctatgaag tgaaaataaa gaggggccgc | 180 |
| tcaaatctcc | tttgggacac | aggggtctttc gaggccagg tgtatttcaa gcctcagtac | 240 |
| cacgcagaaa | tgtgcttcct | ctcttggttc tgtggcaacc agctgcctgc ttacaagtgt | 300 |
| ttccagatca | cctggtttgt | atcctggacc ccctgcccgg actgtgtggc gaagctggcc | 360 |
| gaattcctgt | ctgagcaccc | caatgtcacc ctgaccatct ctgccgcccg cctctactac | 420 |
| tactgggaaa | gagattaccg | aagggcgctc tgcaggctga gtcaggcagg agcccgcgtg | 480 |
| acgatcatgg | actatgaaga | atttgcatac tgctgggaaa actttgtgta caatgaaggt | 540 |
| cagcaattca | tgccttggta | caaattcgat gaaaattatg cattcctgca ccgcacgcta | 600 |
| aaggagattc | tcagatacct | gatggatcca gacacattca ctttcaactt taataatgac | 660 |
| cctttggtcc | ttcgacggcg | ccagacctac ttgtgctatg aggtggagcg cctggacaat | 720 |
| ggcacctggg | tcctgatgga | ccagcacatg gctttctat gcaacgaggc taagaatctt | 780 |
| ctctgtggct | tttacggccg | ccatgcgag ctgcgcttct tggacctggt tccttctttg | 840 |
| cagttggacc | cggcccagat | ctacagggtc acttggttca tctcctggag cccctgcttc | 900 |
| tcctgggct | gtgccgggga | agtgcgtgcg ttccttcagg agaacacaca cgtgagactg | 960 |
| cgcatcttcg | ctgcccgcat | ctatgattac ddcccctat ataaggaggc gctgcaaatg | 1020 |
| ctgcgggatg | ctggggccca | agtctccatc atgacctacg atgagtttga gtactgctgg | 1080 |
| gacacctttg | tgtaccgcca | gggatgtccc ttccagccct gggatggact agaggagcac | 1140 |
| agccaagccc | tgagtgggag | gctgcgggcc attctccaga atcagggaaa ctgaaggatg | 1200 |
| ggcctcagtc | tctaaggaag | gcagagacct gggttgagca gcagaataaa agatcttctt | 1260 |
| ccaagaaatg | caaacagacc | gttcaccacc atctccagct gctcacagac accagcaaag | 1320 |
| caatgtgctc | ctgatcaagt | agatttttta aaaatcagag tcaattaatt ttaattgaaa | 1380 |
| atttctctta | tgttccaagt | gtacaagagt aagattatgc tcaatattcc cagaatagtt | 1440 |
| ttcaatgtat | taatgaagtg | attaattggc tccatattta gactaataaa acattaagaa | 1500 |
| tcttccataa | ttgtttccac | aaacactagc aaa | 1533 |

<210> SEQ ID NO 4
<211> LENGTH: 1278
<212> TYPE: DNA
<213> ORGANISM: Homo sapiens
<220> FEATURE:
<221> NAME/KEY: misc_feature
<222> LOCATION: (1)..(1278)
<223> OTHER INFORMATION: ERCC1

<400> SEQUENCE: 4

| | | | |
|---|---|---|---|
| gggcgagccg | aaggtggagg | tcaaaggggc gtggcgttac agagcctcta gcgctgggtg | 60 |
| ttggggacct | gacgctatgg | agctctcgga gttttgtggg ggacggctgt gagtgggggg | 120 |
| ttcctgctgc | gggatgagaa | cgtagacgcc agtggctcac tcgctcctgg cacttccct | 180 |
| ttcaggctcc | agatggaccc | tgggaaggac aaagagggg tgccccagcc ctcagggccg | 240 |
| ccagcaagga | agaaatttgt | gatacccctc gacgaggatg aggtccctcc tggagtggcc | 300 |
| aagcccttat | tccgatctac | acagagcctt cccactgtgg acacctcggc ccaggcggcc | 360 |
| cctcagacct | acgccgaata | tgccatctca cagcctctgg aagggctgg ggccacgtgc | 420 |
| cccacagggt | cagagcccct | ggcaggagag acgcccaacc aggccctgaa acccggggca | 480 |
| aaatccaaca | gcatcattgt | gagccctcgg cagaggggca atcccgtact gaagttcgtg | 540 |

| | | |
|---|---|---|
| cgcaatgtgc cctgggaatt tggcgacgta attcccgact atgtgctggg ccagagcacc | 600 | |
| tgtgccctgt tcctcagcct ccgctaccac aacctgcacc cagactacat ccatgggcgg | 660 | |
| ctgcagagcc tggggaagaa cttcgccttg cgggtcctgc ttgtccaggt ggatgtgaaa | 720 | |
| gatccccagc aggccctcaa ggagctggct aagatgtgta tcctggccga ctgcacattg | 780 | |
| atcctcgcct ggagccccga ggaagctggg cggtacctgg agacctacaa ggcctatgag | 840 | |
| cagaaaccag cggacctcct gatggagaag ctagagcagg acttcgtctc ccgggtgact | 900 | |
| gaatgtctga ccaccgtgaa gtcagtcaac aaaacggaca gtcagaccct cctgaccaca | 960 | |
| tttggatctc tggaacagct catcgccgca tcaagagaag atctggcctt atgcccaggc | 1020 | |
| ctgggccctc agaaagtaag agctctggga aagaacccaa ggagttgggg aaggagaga | 1080 | |
| gccccaaata aacacaacct gagacccaa agtttttaagg tgaaaaaaga accaaagacc | 1140 | |
| agacacagtg gcttccgcct gtaatcccaa cattttggga ggccaaggcg ggaggactgc | 1200 | |
| ttgaggccag aagttggaga ccagcctggg caagtggaca cctcattttt actaaaaata | 1260 | |
| aaaaaaacta gctgggca | 1278 | |

<210> SEQ ID NO 5
<211> LENGTH: 2935
<212> TYPE: DNA
<213> ORGANISM: Homo sapiens
<220> FEATURE:
<221> NAME/KEY: misc_feature
<222> LOCATION: (1)..(2935)
<223> OTHER INFORMATION: HUS1

<400> SEQUENCE: 5

| | | |
|---|---|---|
| gccgcggctg cgccatccgc ggccatgaag tttcgggcca agatcgtgga cggggcctgt | 60 | |
| ctgaaccact tcacacgaat cagtaacatg atagccaagc ttgccaaaac ctgcaccctc | 120 | |
| cgcatcagcc ctgataagct taacttcatc ctttgtgaca agctggctaa tggaggagtg | 180 | |
| agcatgtggt gtgagctgga acaggagaac ttcttcaacg aatttcaaat ggagggtgtc | 240 | |
| tctgcagaaa acaatgagat ttatttagag ctaacatcgg aaaacttatc tcgagccttg | 300 | |
| aagactgccc agaatgccag ggcttttgaaa atcaaactga ctaataaaca ctttccctgc | 360 | |
| ctcacggtct ccgtggagct gttatctatg tcaagcagta gccgcattgt gacccatgac | 420 | |
| atccccataa aggtgattcc taggaaattg tggaaggact acaagaaacc ggtggtccca | 480 | |
| gatcctgatg ttagtattta tttaccagtc ttgaagacta tgaagagtgt tgtggaaaaa | 540 | |
| atgaaaaaca tcagcaatca ccttgttatt gaagcaaacc tagatggaga attgaatttg | 600 | |
| aaaatagaaa ctgaattagt atgtgttaca actcatttta aagatcttgg aaatcctcca | 660 | |
| ttagcctctg aaagcaccca tgaggacaga aacgtggaac acatggctga agtgcacata | 720 | |
| gatattagga agctcctaca gtttcttgct ggacaacaag taaatcccac aaaggcctta | 780 | |
| tgcaatattg tgaataacaa gatggtgcat tttgatctgc ttcatgaaga cgtgtccctt | 840 | |
| cagtatttca tccctgcgct gtcctagcac cctgtcgctg gagttggcat gcagagactt | 900 | |
| tgtcaggatg ggagaggccg caggtgttgt gttctgatca ctggtctgtg ccctcacagc | 960 | |
| accgcacatc gacacactgt acttatttgt ccctctctaa cattttaact aaaagttgat | 1020 | |
| tcaacaacac acagttggat aaacatatca cttcatgttg ctcatgtctg ttttgctttg | 1080 | |
| ttttttaagac actgaaaaga aaagctagaa tttatttatt cagactttaa agaacaattt | 1140 | |
| ctcattgatg ttgtgaaaat cgtcatgtat ttagacttgg tgtagtagcc agaattcgta | 1200 | |
| aagctgttgc ctgggagctt ggtactttcc ctccaggcag aggctctagc tcagcacggc | 1260 | |

-continued

```
ctgtagcgca cagtcagtct tgcatttcag tgtgttcacc ccgctgctcc tgccccttgg       1320
agcccagtga cagaaagaac agcctctgtc accccgccgc cactgccttg gttactcaga       1380
gcactgtggg gtgtcacagc tgcagcattt ggagtctctc tcttgctgag gactcaagcc       1440
cacctgagtc cactcccctc ttgatgccta gagagctggc ccagccaaca cagctcttag       1500
ctgggagctc cttctgccat tccaactagt ttcttcctgg ggccagtttt gggtttaggt       1560
tgtaattcct tatatttctt tcttccacag tgtatcggat ctgtcgttct ggaaagaaga       1620
cccttctatt tagagtagaa acaaacgaaa cttctaaggt atcatctgtg ttaagtgatg       1680
agaccatatt tctttgatgt ttctgaacat caaagctgat tcagtactgg tagatgtgct       1740
cattctccct gaaacatacc catcatattt cctattataa ttacatctca ttgtcctgtg       1800
gaggtggaca tgataaacat tatcttttgt tttcttgttt tgttttgttt gagacggtct       1860
cattctgtca cccagactgg agtgcagtgc acaatcatg gctcaccgca ttgacctcct        1920
tggctcaagg catcctccca cctcagcttc tgactagct gggactactg gtgtgcacca        1980
ccacacccag ctaatttttca attttttcata gagacagggt ctcactgtgt tgtccaggct     2040
ggtcttgaac tcctgggctc aagccacccg cccacctggg cctcccaaag tgctgggatt       2100
acaggcatca gccatcacac ccatccataa acattatatt aatgtcacat tacaaaactg       2160
agacctaagt tgcttaggat aaaatgaaat tggaagacta gctaacatga aaatttatat       2220
tttggctttt tcatgttttt tgataaaacc agtgtatttg aatgattctt ttgatgttta       2280
gtaatggttt tttgtttgtt ttttggtttt ttttttttgag acggagtctc actctgtcgc      2340
cagtctggag tgctagtggc gcgatcttgg cttactgcag cctccacttc ccaagttcaa       2400
gcgattctcc tgcctcagcc tcccgagtag ctgggactac aggcgcatgc caccacgccc       2460
ggctaatttt tgtattttta gtagagacgg agtttcactg tgttggccag gatggtctcg       2520
atctcgacct cgtgatcacc caccttggcc tctcaaagtg ctgggattac aggcgtgagc       2580
caccacgcct ggcctatgtt taataatgtt gaaataggat ggaatatttt gttaaattaa       2640
cattttaaaa ttagaagaca ccgttttaat ttttaaaccc ttcctcctct cattgtaacg       2700
aaattaattc cagctgcagt gagaaaactt aaaaatcatg atacaaaatg aaacaatatc       2760
tgaaagtagt tttataaaac tgaaattgct gttaaagaga atgtgttagt gacttaacca       2820
tttgctctat gtgatgttta ttatcaaata catataattt tgaagatttt aatgaatggc       2880
ttaagatttt atctttgtgt agaatgtggc taaagaaacc ttagttgaga ttcaa            2935
```

<210> SEQ ID NO 6
<211> LENGTH: 10961
<212> TYPE: DNA
<213> ORGANISM: Homo sapiens
<220> FEATURE:
<221> NAME/KEY: misc_feature
<222> LOCATION: (1)..(10961)
<223> OTHER INFORMATION: PGBD5

<400> SEQUENCE: 6

```
ggcagggccc gcctctggcg gctcgcgccc gggaaggtcg gcagccgagc gccggaggcc        60
gtggagaggg cgggcaggga ggcggcgggc gccgaggaga cgcagcggcg gcggtggtgg       120
cggtggtggc ggcggtggcg gcggcggcgc ctggtctcgg ccgcagcctc tgcgtcccgc       180
ccgctctggg tcgcccctgc cagccccgcg gcgggctcgc ctcccgccgc ggcccgcagc       240
ctgcggcgcc cgagctccga gggcgcttcc ccgggcgctg ggcccgaggc ggccaagacg       300
```

```
gcgggccggc cgggcacggg gcggcgggcg ctgtgctgcg ggctgcgctg gtggggggcg    360
gcgggccgcg gcgcgggccc agggcccggc gtgtgcggct gggaggcact gtgggggcgg    420
gcgcgcgggc ggcggccggg gccatggccg agggcggcgg gggcgcgcgg aggagggcgc    480
cggcgctgct cgaggctgcc cgcgcgcgct acgagagcct gcacatctcg gacgacgtgt    540
tcggcgagtc cggcccggac agcggcggga accccttcta cagcacctcg gccgcctcgc    600
gctcctcctc ggccgcctcc tcggacgacg agcgcgagcc cccgggaccc ccaggggccg    660
ccccgccacc gccccgcgcc ccggacgcac aggagccgga ggaggacgag gccggcgcgg    720
gctggagcgc agcgctgcgg gaccgccgc ccccgcgctt cgaggatacc ggcggtccca    780
cccgaaagat gcccccagc gccagtgccg tggacttctt ccagctcttt gtcccagaca    840
acgtcctcaa gaacatggtg gtgcagacaa acatgtatgc caagaagttc caggagcggt    900 tgggagcga cggagcctgg gtggaggtga cgctgacgga gatgaaggcg ttcctgggct    960
acatgatctc caccagcatc tcccactgcg agtccgtcct cagcatctgg agcggaggct   1020
tctacagcaa ccgcagcctc gccctcgtca tgagccaggc ccgcttcgag aagatcctca   1080
agtacttcca cgtcgtggcc ttccgctcca gccagaccac gcacgggctc tacaaggtcc   1140
agcccttcct cgactccctg cagaacagct tcgactctgc cttcaggcct tcccaaaccc   1200
aggtgctaca tgaaccctg atcgatgagg atcctgtatt cattgccacg tgcacagagc   1260
gggagctgcg aaagaggaaa aagcggaaat tcagcctctg ggtcagacaa tgttcttcca   1320
ctggcttcat catccagatt tatgtccacc tgaaggaagg tgggggccca gatggcctgg   1380
atgcgctgaa gaataagccc cagctccaca gcatggtggc caggagcctg tgccggaacg   1440
cggcaggcaa gaactacatc attttcacgg ggcccagcat caccagcctg acgctgtttg   1500
aagagtttga gaagcaaggg atttactgct gcggcttgct ccgcgcgcgg aagagtgact   1560
gcaccggcct cccactgtcc atgctgacca acccagccac accccggcc cggggccagt   1620 accaaatcaa gatgaagggg aacatgtcct tgatctgctg gtacaacaaa ggacacttcc   1680
gcttcctgac caacgcctac tccccggtgc agcagggagt catcatcaaa aggaagagtg   1740
gggagatccc atgccccttg gccgtggagg cgtttgccgc tcacctgagc tacatctgca   1800
gatacgatga caaatacagc aagtatttca tttctcataa accaaacaag acctggcagc   1860
aggtgttctg gttcgccatc agcatcgcca tcaacaatgc ctacatcctg tacaaaatgt   1920
cagacgccta ccacgtgaag aggtacagcc gggcgcagtt tggagagaga ctcgtcagag   1980
agctgctggg cttggaggat gcctctccga cccactgatg ctgggggcgc aggactcggt   2040
caagggaggg gcaagaggag gaggagagcc tgccgttcca acttgcccat cagagacccg   2100
gacacggcct ggtgtgtggc ttgctgcctg ggagggatgc acagggcctc tggagggaca   2160
ggatggacct ggtcagagga cggttgctgt cctcatttgc attccaagaa gagcatgtcc   2220
tccctcgaga aacagtgccg ccggtgtgat gagcacttac acccacgttc tcaagggcag   2280
attctctcat gacatccgtg gagcttgcga ggcagcgtgg actggtgact gtgaaggaag   2340
gcccccgtgg tagaatgagc tggagcacgc tctaagagag atgcctgctt cctaaagatc   2400
tacagcaatc tgggacgtgg ttcaagttca agacttgaag gaagcaaaga cgccctgcat   2460
ggttacaatg gctcaggtgt caggggaggc cggagggttt tccagcattt gcctcatgcc   2520
agcacctttg aaccggtctc ttagaagaag acacacatcc tgggtgtaca gtggtgaaat   2580
ggggagtggg tgcccattct gaaaaacgag gcattcctgc tcattccctc tgcttagctg   2640
gtgggcaggg gagagaggga aatgccaaaa acttggagtg aaggatgatg ctatttttta   2700
```

```
tttttaaata tatcttcagg ttattttctt actgttgctt cagatctaat gtaaaaggca    2760
gatgtcccct cctctccacc cccgacgctg accccggcct cagtcacggc tctttgcatg    2820
atcacagttc tgtgttctgg cctgtggcag ggccgggaag ggccgctggc ttccgaacag    2880
acgtggttgc tctccacgag gcgcatgggg agcccgcggg ccctaagctt tgtcgcagat    2940
gtcatcattg gcagaattac ttgtcttgaa aaataagtag cattgctgaa acacacaacc    3000
gaattctcta cgatggccat ttgctcattg tctttcctct gtgtgtagtg agtgaccctg    3060
gcagtgtttg cctgctcaga gtggcccctc agaacaacag ggctggcctt ggaaaaaccc    3120
caaaacagga ctgtggtgac aactctggtc aggtgtgatt tgacatgagg gccggaggcg    3180
gttgctgacg gcaggactgg agaggctgcg tgcccggcac tggcagcgag gctcgtgtgt    3240
cccccaggca gatctgggca ctttcccaac ccaggtttat gcgtctccag ggaagcctcg    3300
gtgccagagt ggtgggcaga tctgaccatc cccacagacc agaaacaagg aatttctggg    3360
attacccagt cccccttcaa cccagttgat gtaaccacct catttttac aaatacagaa    3420 tctattctac tcaggctatg ggcctcgtcc tcactcagtt attgcgagtg ttgctgtccg    3480
catgctccgg gccccacgtg gctcctgtgc tctagatcat ggtgactccc cgcccgtg    3540 gttggaatcg atgccacgga ttgcaggcca aatttcagat cgtgtttcca acacccttg    3600 ctgtgccctt taatgggatt gaaagcactt ttaccacatg gagaaatata ttttaattt    3660 gtgatgcttt tctacaaggt ccactatttc tgagtttaat gtgtttccaa cacttaagga    3720
gactctaatg aaagctgatg aattttcttt tctgtccaaa caagtaaaat aaaaataaaa    3780
gtctatttag atgttgattc tccgttaata cgtgaattcg tttaaaaggt cagggaacag    3840
gcggggtgcg gtggctcatg cctgtaatcc cagcacttt ggaggctgaa gcgggcggat    3900
cgcttgagtc caggagtttg agaccagcat tggcaacatg gcgaaagccc atttctacaa    3960
aaaatacaag aattaggtgt ggtggcacat gcctgcagtc ccagctactt gggaggctga    4020
ggtgggagga tctcttgagc cactgcactc cagcctgggt gacagagcca gaccctgtat    4080
caagaaaaaa aacaaggtga aggaacaaaa atacaggcta ctcttttaaa tacttgattt    4140
tttttgttat ataatctggt gtgtatgata ttaactgttc ttggtgtctc aaaccactga    4200
gcagtttaaa aagaaatgt ttttgagttt ggctaataga aatacctctt gatgttgcag    4260
ttgtatgagt gcagttgtat ttgaggtgcc tgtttcattg aagacactag caggcctgcc    4320
ttccggcctg gtggttttcc ctcttttctt ctagtttgtg tcgtgtgtca ttccagatga    4380
gcaggaagag gtgctgttct gacaggcagt gggtggctgc attccccagt catgagaaa    4440 taattgtaac attgtaacac tctgtttcta aaatggcagc cacctgttgt ctgatacatg    4500
atgggaaaag gcagctgttg agccgggtct aggggaggct tcagtggcca cttcaggtct    4560
ctggaggaat gctgttgact gagaagagtt tctcttctcc atccagaagg acagaatagc    4620
atgtaggacg gactgacaga acctccaggg acctggaccT tgccttagag atgtgattca    4680 aagtggctt ttggagtgac tctagttgaa gtgcatctgg ttccagtatc tccctgggtt    4740
caacagccct caggttgatt cttgattggc tttggagtag ctggccatcc ctggggatga    4800
ggaaagagca tcgtaagtgg tcttatgaca gagggagcca gcatgccct ggctgagtat    4860 atggggctgg caagcaccac tgcacacatg gcaagtgaga gcccattcca ctcagatcca    4920
gccactaagc caagccgatc ccctgaggga tgtctctgct gcaggctctg gaaaaaaag    4980 atggagcaat gagcttccca gccttatgca aaacaaaaca cccacaaaaa cttccaagct    5040
```

```
tctccaaaga gaatctgcat ttccctgcaa ctcacaggga attgaacctg cactgagctt   5100
cacggagttt atgagacctt cccattactg cagttgtgtt gagcgtcccg tgaggtcctt   5160
cttaggcaaa tttaacttca ttgagtgaat gtctgtttct gtttggtgcc tacttgatca   5220
ggttccatat tcgactttca ttgtctttcc ccacactctg ctccctaaag agcctcgatt   5280
ttggccaggt gcggtggctc acacctgtaa tcccagcact ttgggaggcc gaggcaggcg   5340
gatcacaagg ccaggagatt gagaccagcc tggccaatat ggtgaaaccc catctctact   5400
aaaaatacaa aaattagctg ggtgtggtgg tggacacctg tagtcccagc tactcgggag   5460
gctaagcagg agaatatctt gaatccggga agcagaggct gcagtgagcc aagatcgcac   5520
cactgcactc cagcctgggt gacagagcga gactccaacc cccaccccgc cacaaaaaaa   5580
aaaaaaaaaa aaaagcctcg agtttgaaca acgtcttccc gtggtccatg ggacattata   5640
ctagggacat ctttcaaaag tcaggcaagt catatggaaa agtcttggtg gctgggtcat   5700
tctgagcaaa cacatccagt actgactaaa tcagatgagg cttggtcacc aaaattgagt   5760
taactctgct gcgtgcaaga agcaagaaga ttgcaggtcc ccaggacaga gcctggaagg   5820
ttctgaatcc ttcctgtgtg gcccgtgtgt caccatcctc cccagggacc caggctcagc   5880
ccccccaaca gtgaggggggg gtcaccaagc atcaggctga gaggaagcag ggcaaacccg   5940
ggagggccat ggggccttgc aactacgcaa gcctcacaca ttctcctcca gtctgcattc   6000
atggcaaaaa aaaaacattt ccccacttgc ctgggattgg ggcgagaaca agtcaacgac   6060
actgatgggg gagaaaggtg accttgggtg tggtacctcc cagatctgtc tcctgcatcc   6120
tcgcaggtgc tgtgtttgaa aggtatgaca gcggtggcta acaggcaggc cacttccag    6180
gcggcttggg gtggccttc tgccccagag ccttactcct cacagggatc cctgtgggtt    6240
aggcatggac tgtcaccacg cccagatgga gtggtgcaat ggttcgccca ggtaagcaga   6300
cccgggtttg cctgacgcag gaggccgcgt cctaactgct gtgggcactg ctgtcctga    6360
ttcatcacga ggacggggga ttttatccct gacttacctg acaactttgt gggggatttt   6420
ctccttttcca tatccaatcc tctctgctga tccgaatact gaaaacaatc attatgagat   6480
ccgggacatc accctccccc tgggtccttt tcttgtccta gatggagatg ggtgttttgg   6540
agcttaacaa ctactgaagc tgaagttagc ctggtaggga gccactattc tgggggggcat  6600
ttggacaggg caagcccttg gccacaccag accctgagcc agaaagaacc atagcgattt   6660
cctcacccag atggccccag ctcacagtat ggggagagtg ggatggggtg ggggagtgga   6720
gccagctgtg gggtctcatc agagtgccct gggatctagg ccagaggcgc cgtcttcacc   6780
cacatgccag cttttgtggtt ctggtccctc ttccttaagc gagggcttgc caagctttgg  6840
ctgtggaaag ccttagcctt gtgtagtggg agttccaaac gaaagaagtc cccagaagtt   6900
cacaaggtag tggccaggga aagtgtcccc agtgcccct ccccaccggt ggcctctgca    6960
gcttgctttg gaaaacagtt ctgtctgtga agaaatctct cctgttacgg ccctgtgtca   7020
gtcaatgcgg gcttggctgt ctgcccaaat accttccgtt cttatcagga acatgactga   7080
ggcttctcac ttttgactcc atcacttaat ccctttttct ccgtggcttc tgtgtgtctc   7140
atcttcgaga atatttctca gccttctttg caggtatgtt attctctccc aataagaaat   7200
aaagagtatc aggtaccaaa gtggcactta gagctgttgc cataaaatag caccagagag   7260
taagcatgcc ctctggccac gcagctcgct gccatttagc catctctgtg tccctccctc   7320
cctggggtgc ccagtgcgca ccccagttct ccagcagccc aggcacattc tcctagctct   7380
gaccccctgtc tggtgggggc cgggcagcct ctcttgagtg tagggcggtg gtgctggcgc  7440
```

-continued

```
tggtggcagc tctgtgtgaa ctgtgttccg gggagggtgg ggcaccttca cccttccgtg   7500
tatacccatg tatacacggt cgtaatgagg agactcctgc gggagacttg attgtgcgct   7560
ccatgtcact agctactcta caagcagata ctattcttca ggttttttcc ttagttgcct   7620
ggaagcttga ccttgtgtgc atgtatttgg agatgaaaac agaaagggcg gggaggacat   7680
cggcttgtgt gaaagaccta ggaagacgat ggaggagtgt gtgcggcttc cctcacgtgt   7740
caagcctcct ggctccctca ggtggaaggg gcactttatg gccaaggaaa ttcagtgagg   7800
agtgaagggt gaggctgagc ccgccagata aatcagcctc ggccctcccc tccccaaggg   7860
tcagcccccg gcagcgcacc tctgttcttg gtgcgtctcg ctagtctttg attcattctt   7920
ctgccgtctt cacccaagcc tcgctggact aaagagtgac agttaatgca catggagcat   7980
ttctgttcca gcaggtcacg tctccctgta tggttccttt gctgagtcct cagcattgcc   8040
ctgggagctg acaaccatcg gtccccctttt tgtgatggga aagtgacact ctgagagccg   8100
tggtgactct acagggtgtg gagccaggtt gaccctcact ctgtctgctc cagggcttcc   8160
tggttctcag ccactgctgc ttctgaactg ctacaggcca ggcattgtgc taagaactgg   8220
gcacgtgtta ccccaacgtg gtctgtgccc ttgagggtgc catgactgaa acacgttggg   8280
ggcacagagc aggctgattc tccgccgaaa gaaggctcca gccagaggcc gagacccgt   8340 gtgggggagg tggcagtcac cattgctgct ggactcagca accccagac cctccacctt   8400 gcttggcagg catcacatgc acctggctta gcacatccct gcaaacacaa gagtctgagc   8460
ctcctcaaga ggctgcagtc acactgcatt tgaccaggac ttgccaacct gcaacttgcc   8520
ctgagagcca ggtatgcgtg tgtgtatctg gggagcacgc cccaaacatg agcagggacg   8580
gtgttcccag ctatccgaga ggtcatgccc aagccaaaag gaaggctcta gctcttaaac   8640
atgaataagt ttattccttt catttccaca gtgtcttatg cttgcttctg ttttctccaa   8700
ggaagtatgg tgcccaccta ctcctccagc ctgacgatcc atgtgagggt tccttgttcc   8760
cagcccaatt ctcatgtccc acctttctcc actaagaaac agccaaattt tggcaagagt   8820
cgtggtagga aaaaaaaaca ataattgggc agatgaggat ttttcacttt ttgactagtt   8880 cttttctctag actttcctgt ctttttaaaa cttctagttt cccccttgag cgctccctcc   8940
cagtgggtag accacggaag gaatgaacag gggatggaag caggggatgc agtccctatt   9000
atttcaatag attggaaaga tgggcccaga acaattgcgt acggtgttca gtgtaaattg   9060
aagatctgga gttgcaggat tgttgaggca atttttagtt gctttgctcc atctaaacac   9120
aaggccatag gatagtgtga cttttgtagct tcatcaccgt atccacatca gaagtacaat   9180
gtccacttaa tacatatata cacatatgta cgtatacaca tatacacatg tgtacatatg   9240
tatgtataca catgcacatg tgtacgtatg tatgtataca catacatata tgtgtacaca   9300
tatacatatg tatgtataca catagatata tgtgtacaca taaacatatg tatgtataca   9360
cataaacatg tatgtataca catacatata tgtgtacaca tatacttatg tatgtataca   9420
catacatata tgtgtacaca tatacttatg tatgtataca catacatata tgtgtacaca   9480
tatacttatg tatgtataca catacatata tgtgtacaca tatacacata tacatatatg   9540
tgtacacata aatatgtatg tatccatata tgtatatata tacacatgta tacagatatg   9600
catctatatg tatacctcta tatgtatgca catatacata tatgtataca tatatacata   9660
tatgcataca tctataatat atgtatgtgt atatatacac atacagtgtc cacttaatat   9720
atatatctat cttgtgtgta tgtgtgtgta aatatacaca cacatacaca cacgataaaa   9780
```

-continued

| | |
|---|---|
| tacagagtct accacatgat gagcctctgc taggtcctta gcaatcaaac cacatgtcca | 9840 |
| gtcctggccc ccattctaca actaaacaca tgggccagtt tagggtcca ggagggcaag | 9900 |
| aatggtgggt ccacgtagaa accaggtgag ggaggagcag tccacagggc tggggtgatg | 9960 |
| ggctggtgaa gcagtgttcc aggaggggaa ctgctgctca cagggctgtc ctggtcgccc | 10020 |
| tcgggataca gccagacttg atccgagtgg ctcccggggc tgaatgggga ccgccgggtg | 10080 |
| catatcccag gaggcagcct tcagctcagt ggggaaagca gtttccaacc ttagagctgc | 10140 |
| ccaacactag cacagggcac ctgagaaagg aggggcccct ctgcctttac tctgtctccc | 10200 |
| actagaggca gctggttcct tcagggaact ctggtggggg gtgaggggt ggctggttct | 10260 |
| cagtgggcag gggtgaccct actggggtca gtgggctggc aatgctggtc ttcactaaga | 10320 |
| agagttgaaa atagccagga agctaagccc tggctcctgg gctcctgggc agatgcttaa | 10380 |
| ttaggaggaa gaaggaacca aaatcatgaa cacaactggc tctctcaggg ggaggctgtc | 10440 |
| accctccaag ctcttcttcc ccttcctcaa atggagattc acactcatcc ctagttcagg | 10500 |
| agagccgcca ttgatgatga ggaaatccgt gtcaaagaag ctggaaagac tgctattcat | 10560 |
| tgtgagaatt tgtttccac tgctacatta cattgtttct tcttgttttc ccttccaatt | 10620 |
| tccagttaag aatctttcac agaaaatttt taatttatc acaaactgca cagatatcac | 10680 |
| acagctgcac ccccatttgg tgacacaaag catacccttc tgtgaagatt ttcactttac | 10740 |
| gccaaggcat gattgtcact ttcgccaag gcaataaatt tttacaaatt ttgtataaca | 10800 |
| ggagctgaat tctgggttct caaatgtgaa atgtggcaaa aaaaaaaaa aaaaaaaaa | 10860 |
| agatttaatt caagcatttt gtcatgtggt tcttatttct tcaaccaagt ttgtttacag | 10920 |
| tcactgcctt tgaaatacag tcaaatacat ctgtttgctt c | 10961 |

<210> SEQ ID NO 7
<211> LENGTH: 3444
<212> TYPE: DNA
<213> ORGANISM: Homo sapiens
<220> FEATURE:
<221> NAME/KEY: misc_feature
<222> LOCATION: (1)..(3444)
<223> OTHER INFORMATION: POLD1

<400> SEQUENCE: 7

| | |
|---|---|
| agtcaggggt cacggcggcg taggctgtgg cgggaaacgc tgtttgaagc gggatggatg | 60 |
| gcaagcggcg gccaggccca gggcccgggg tgccccaaa gcgggcccgt gggggcctct | 120 |
| gggatgatga tgatgcacct cggccatccc aattcgagga ggacctggca ctgatggagg | 180 |
| agatggaggc agaacacagg ctgcaggagc aggaggagga ggagctgcag tcagtcctgg | 240 |
| aggggggttgc agacgggcag gtcccaccat cagccataga tcctcgctgg cttcggccca | 300 |
| caccaccagc gctggacccc cagacagagc ccctcatctt ccaacagttg gagattgacc | 360 |
| attatgtggg cccagcgcag cctgtgcctg ggggcccccc accatcccgc ggctccgtgc | 420 |
| ctgtgctccg cgccttcggg gtcaccgatg aggggttctc tgtctgctgc cacatccacg | 480 |
| gcttcgctcc ctacttctac acccagcgc cccctggttt cgggcccgag cacatgggtg | 540 |
| acctgcaacg ggagctgaac ttggccatca gccgggacag tcgcgggggg agggagctga | 600 |
| ctgggccggc cgtgctggct gtggaactgt gctcccgaga gagcatgttt gggtaccacg | 660 |
| ggcacgcccc ctcccccgttc ctgcgcatca ccgtggcgct gccgcgcctc gtggcccgg | 720 |
| cccgccgtct cctggaacag ggcatccgtg tggcaggcct gggcacgccc agcttcgcgc | 780 |
| cctacgaggc caacgtcgac tttgagatcc ggttcatggt ggacacggac atcgtcggct | 840 |

```
gcaactggct ggagctccca gctgggaaat acgccctgag gctgaaggag aaggctacgc    900
agtgccagct ggaggcggac gtgctgtggt ctgacgtggt cagtcaccca ccggaagggc    960
catggcagcg cattgcgccc ttgcgcgtgc tcagcttcga tatcgagtgc gccggccgca   1020
aaggcatctt ccctgagcct gagcgggacc ctgtcatcca gatctgctcg ctgggcctgc   1080
gctgggggga gccggagccc ttcctacgcc tggcgctcac cctgcggccc tgtgccccca   1140
tcctgggtgc caaggtgcag agctacgaga aggaggagga cctgctgcag gcctggtcca   1200
ccttcatccg tatcatggac cccgacgtga tcaccggtta caacatccag aacttcgacc   1260
ttccgtacct catctctcgg gcccagaccc tcaaggtaca acattccct ttcctgggcc    1320 gtgtggccgg cctttgctcc aacatccggg actcttcatt ccagtccaag cagacgggcc   1380
ggcgggacac caaggttgtc agcatggtgg ccgcgtgca gatggacatg ctgcaggtgc    1440
tgctgcggga gtacaagctc cgctcctaca cgctcaatgc cgtgagcttc cacttcctgg   1500
gcgagcagaa ggaggacgtg cagcacagca tcatcaccga cctgcagaat gggaacgacc   1560
agacccgccg ccgcctggct gtgtactgcc tgaaggatgc ctacctgcca ctgcggctgc   1620
tggagcggct catggtgctg gtgaacgccg tggagatggc gagggtcact ggcgtgcccc   1680
tcagctacct gctcagtcgt ggccagcagg tcaaggtcgt atcccagctg ttgcggcagg   1740
ccatgcacga ggggctgctg atgcccgtgg tgaagtcaga gggcggcgag gactacacgg   1800
gagccactgt catcgagccc ctcaaagggt actacgacgt cccatcgcc accctggact    1860 tctcctcgct gtacccgtcc atcatgatgg cccacaacct gtgttacacc acgctccttc   1920
ggcccgggac tgcacagaaa ctgggcctga ctgaggatca gttcatcagg acccccaccg   1980
gggacgagtt tgtgaagacc tcagtgcgga aggggctgct gccccagatc ctggagaacc   2040
tgctcagtgc ccggaagagg gccaaggccg agctggccaa ggagacagac cccctccggc   2100
gccaggtcct ggatggacgg cagctggcgc tgaaggtgag cgccaactcc gtatacggct   2160
tcactggcgc ccaggtgggc aagttgccgt gcctggagat ctcacagagc gtcacggggt   2220
tcggacgtca gatgatcgag aaaaccaagc agctggtgga gtctaagtac acagtggaga   2280
atggctacag caccagtgcc aaggtggtgt atggtgacac tgactccgtc atgtgccgat   2340
tcggcgtgtc ctcggtggct gaggcgatgg ccctggggcg ggaggccgcg gactgggtgt   2400
caggtcactt cccgtcgccc atccggctgg agtttgagaa ggtctacttc ccatacctgc   2460
ttatcagcaa gaagcgctac gcgggcctgc tcttctcctc ccggcccgac gcccacgacc   2520
gcatggactg caagggcctg gaggccgtgc cagggacaga ctgcccctc gtggccaacc    2580 tggtcactgc ctcactgcgc cgcctgctca tcgaccgaga ccctgagggc gcggtggctc   2640
acgcacagga cgtcatctcg gacctgctgt gcaaccgcat cgatatctcc cagctggtca   2700
tcaccaagga gctgacccgc gcggcctccg actatgccgg caagcaggcc cacgtggagc   2760
tggccgagag gatgaggaag cgggaccccg ggagtgcgcc cagcctgggc gaccgcgtcc   2820
cctacgtgat catcagtgcc gccaagggtg tggccgccta catgaagtcg gaggacccgc   2880
tgttcgtgct ggagcacagc ctgcccattg acacgcagta ctacctggag cagcagctgg   2940
ccaagcccct cctgcgcatc ttcgagccca tcctgggcga gggccgtgcc gaggctgtgc   3000
tactgcgggg ggaccacacg cgctgcaaga cggtgctcac gggcaaggtg gcggcctcc    3060 tggccttcgc caaacgccgc aactgctgca ttggctgccg cacagtgctc agccaccagg   3120
gagccgtgtg tgagttctgc cagccccggg agtctgagct gtatcagaag gaggtatccc   3180
```

-continued

```
atctgaatgc cctggaggag cgcttctcgc gcctctggac gcagtgccag cgctgccagg       3240
gcagcctgca cgaggacgtc atctgcacca gccgggactg ccccatcttc tacatgcgca       3300
agaaggtgcg gaaggacctg aagaccagg agcagctcct gcggcgcttc ggaccccctg        3360
gacctgaggc ctggtgacct tgcaagcatc ccatggggcg ggggcgggac cagggagaat       3420
taataaagtt ctggactttt gcta                                              3444
```

<210> SEQ ID NO 8
<211> LENGTH: 897
<212> TYPE: PRT
<213> ORGANISM: Homo sapiens
<220> FEATURE:
<221> NAME/KEY: MISC_FEATURE
<222> LOCATION: (1)..(897)
<223> OTHER INFORMATION: RBBP8

<400> SEQUENCE: 8

```
Met Asn Ile Ser Gly Ser Ser Cys Gly Ser Pro Asn Ser Ala Asp Thr
1               5                   10                  15

Ser Ser Asp Phe Lys Asp Leu Trp Thr Lys Leu Lys Glu Cys His Asp
                20                  25                  30

Arg Glu Val Gln Gly Leu Gln Val Lys Val Thr Lys Leu Lys Gln Glu
            35                  40                  45

Arg Ile Leu Asp Ala Gln Arg Leu Glu Glu Phe Phe Thr Lys Asn Gln
        50                  55                  60

Gln Leu Arg Glu Gln Gln Lys Val Leu His Glu Thr Ile Lys Val Leu
65                  70                  75                  80

Glu Asp Arg Leu Arg Ala Gly Leu Cys Asp Arg Cys Ala Val Thr Glu
                85                  90                  95

Glu His Met Arg Lys Lys Gln Gln Glu Phe Glu Asn Ile Arg Gln Gln
            100                 105                 110

Asn Leu Lys Leu Ile Thr Glu Leu Met Asn Glu Arg Asn Thr Leu Gln
        115                 120                 125

Glu Glu Asn Lys Lys Leu Ser Glu Gln Leu Gln Gln Lys Ile Glu Asn
130                 135                 140

Asp Gln Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu
                165                 170                 175

Arg Arg Lys Glu Asn Pro His Val Arg Tyr Ile Glu Gln Thr His Thr
            180                 185                 190

Lys Leu Glu His Ser Val Cys Ala Asn Glu Met Arg Lys Val Ser Lys
        195                 200                 205

Ser Ser Thr His Pro Gln His Asn Pro Asn Glu Asn Glu Ile Leu Val
210                 215                 220

Ala Asp Thr Tyr Asp Gln Ser Gln Ser Pro Met Ala Lys Ala His Gly
225                 230                 235                 240

Thr Ser Ser Tyr Thr Pro Asp Lys Ser Ser Phe Asn Leu Ala Thr Val
                245                 250                 255

Val Ala Glu Thr Leu Gly Leu Gly Val Gln Glu Glu Ser Glu Thr Gln
            260                 265                 270

Gly Pro Met Ser Pro Leu Gly Asp Glu Leu Tyr His Cys Leu Glu Gly
        275                 280                 285

Asn His Lys Lys Gln Pro Phe Glu Glu Ser Thr Arg Asn Thr Glu Asp
    290                 295                 300
```

-continued

Ser Leu Arg Phe Ser Asp Ser Thr Ser Lys Thr Pro Gln Glu Glu
305                 310                 315                 320

Leu Pro Thr Arg Val Ser Ser Pro Val Phe Gly Ala Thr Ser Ser Ile
                325                 330                 335

Lys Ser Gly Leu Asp Leu Asn Thr Ser Leu Ser Pro Ser Leu Leu Gln
            340                 345                 350

Pro Gly Lys Lys Lys His Leu Lys Thr Leu Pro Phe Ser Asn Thr Cys
        355                 360                 365

Ile Ser Arg Leu Glu Lys Thr Arg Ser Lys Ser Glu Asp Ser Ala Leu
370                 375                 380

Phe Thr His His Ser Leu Gly Ser Glu Val Asn Lys Ile Ile Ile Gln
385                 390                 395                 400

Ser Ser Asn Lys Gln Ile Leu Ile Asn Lys Asn Ile Ser Glu Ser Leu
                405                 410                 415

Gly Glu Gln Asn Arg Thr Glu Tyr Gly Lys Asp Ser Asn Thr Asp Lys
            420                 425                 430

His Leu Glu Pro Leu Lys Ser Leu Gly Gly Arg Thr Ser Lys Arg Lys
        435                 440                 445

Lys Thr Glu Glu Glu Ser Glu His Glu Val Ser Cys Pro Gln Ala Ser
    450                 455                 460

Phe Asp Lys Glu Asn Ala Phe Pro Phe Pro Met Asp Asn Gln Phe Ser
465                 470                 475                 480

Met Asn Gly Asp Cys Val Met Asp Lys Pro Leu Asp Leu Ser Asp Arg
                485                 490                 495

Phe Ser Ala Ile Gln Arg Gln Glu Lys Ser Gln Gly Ser Glu Thr Ser
            500                 505                 510

Lys Asn Lys Phe Arg Gln Val Thr Leu Tyr Glu Ala Leu Lys Thr Ile
        515                 520                 525

Pro Lys Gly Phe Ser Ser Arg Lys Ala Ser Asp Gly Asn Cys Thr
530                 535                 540

Leu Pro Lys Asp Ser Pro Gly Glu Pro Cys Ser Gln Glu Cys Ile Ile
545                 550                 555                 560

Leu Gln Pro Leu Asn Lys Cys Ser Pro Asp Asn Lys Pro Ser Leu Gln
                565                 570                 575

Ile Lys Glu Glu Asn Ala Val Phe Lys Ile Pro Leu Arg Pro Arg Glu
            580                 585                 590

Ser Leu Glu Thr Glu Asn Val Leu Asp Asp Ile Lys Ser Ala Gly Ser
        595                 600                 605

His Glu Pro Ile Lys Ile Gln Thr Arg Ser Asp His Gly Gly Cys Glu
610                 615                 620

Leu Ala Ser Val Leu Gln Leu Asn Pro Cys Arg Thr Gly Lys Ile Lys
625                 630                 635                 640

Ser Leu Gln Asn Asn Gln Asp Val Ser Phe Glu Asn Ile Gln Trp Ser
                645                 650                 655

Ile Asp Pro Gly Ala Asp Leu Ser Gln Tyr Lys Met Asp Val Thr Val
            660                 665                 670

Ile Asp Thr Lys Asp Gly Ser Gln Ser Lys Leu Gly Gly Glu Thr Val
        675                 680                 685

Asp Met Asp Cys Thr Leu Val Ser Glu Thr Val Leu Leu Lys Met Lys
    690                 695                 700

Lys Gln Glu Gln Lys Gly Glu Lys Ser Ser Asn Glu Glu Arg Lys Met
705                 710                 715                 720

Asn Asp Ser Leu Glu Asp Met Phe Asp Arg Thr Thr His Glu Glu Tyr

```
            725                 730                 735
Glu Ser Cys Leu Ala Asp Ser Phe Ser Gln Ala Asp Glu Glu Glu
        740                 745                 750

Glu Leu Ser Thr Ala Thr Lys Lys Leu His Thr His Gly Asp Lys Gln
        755                 760                 765

Asp Lys Val Lys Gln Lys Ala Phe Val Glu Pro Tyr Phe Lys Gly Asp
770                 775                 780

Glu Arg Glu Thr Ser Leu Gln Asn Phe Pro His Ile Glu Val Val Arg
785                 790                 795                 800

Lys Lys Glu Glu Arg Arg Lys Leu Leu Gly His Thr Cys Lys Glu Cys
                805                 810                 815

Glu Ile Tyr Tyr Ala Asp Met Pro Ala Glu Arg Glu Lys Lys Leu
                820                 825                 830

Ala Ser Cys Ser Arg His Arg Phe Arg Tyr Ile Pro Pro Asn Thr Pro
                835                 840                 845

Glu Asn Phe Trp Glu Val Gly Phe Pro Ser Thr Gln Thr Cys Met Glu
        850                 855                 860

Arg Gly Tyr Ile Lys Glu Asp Leu Asp Pro Cys Pro Arg Pro Lys Arg
865                 870                 875                 880

Arg Gln Pro Tyr Asn Ala Ile Phe Ser Pro Lys Gly Lys Glu Gln Lys
                885                 890                 895

Thr

<210> SEQ ID NO 9
<211> LENGTH: 199
<212> TYPE: PRT
<213> ORGANISM: Homo sapiens
<220> FEATURE:
<221> NAME/KEY: MISC_FEATURE
<223> OTHER INFORMATION: APOBEC3A

<400> SEQUENCE: 9

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
                20                  25                  30

Leu Cys Tyr Glu Val Glu Arg Leu Asp Asn Gly Thr Ser Val Lys Met
            35                  40                  45

Asp Gln His Arg Gly Phe Leu His Asn Gln Ala Lys Asn Leu Leu Cys
        50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
                100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
```

```
                    180                 185                 190
Ile Leu Gln Asn Gln Gly Asn
        195

<210> SEQ ID NO 10
<211> LENGTH: 382
<212> TYPE: PRT
<213> ORGANISM: Homo sapiens
<220> FEATURE:
<221> NAME/KEY: MISC_FEATURE
<222> LOCATION: (1)..(382)
<223> OTHER INFORMATION: APOBEC3B

<400> SEQUENCE: 10

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
    290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335
```

```
Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu Glu His Ser Gln Ala
            355                 360                 365

Leu Ser Gly Arg Leu Arg Ala Ile Leu Gln Asn Gln Gly Asn
            370                 375                 380

<210> SEQ ID NO 11
<211> LENGTH: 323
<212> TYPE: PRT
<213> ORGANISM: Homo sapiens
<220> FEATURE:
<221> NAME/KEY: MISC_FEATURE
<222> LOCATION: (1)..(323)
<223> OTHER INFORMATION: ERCC1

<400> SEQUENCE: 11

Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
    50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
    130                 135                 140

Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
    210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255

Phe Gly Ser Leu Glu Gln Leu Ile Ala Ala Ser Arg Glu Asp Leu Ala
            260                 265                 270

Leu Cys Pro Gly Leu Gly Pro Gln Lys Val Arg Ala Leu Gly Lys Asn
        275                 280                 285

Pro Arg Ser Trp Gly Lys Glu Arg Ala Pro Asn Lys His Asn Leu Arg
    290                 295                 300
```

```
Pro Gln Ser Phe Lys Val Lys Lys Glu Pro Lys Thr Arg His Ser Gly
305                 310                 315                 320

Phe Arg Leu

<210> SEQ ID NO 12
<211> LENGTH: 280
<212> TYPE: PRT
<213> ORGANISM: Homo sapiens
<220> FEATURE:
<221> NAME/KEY: MISC_FEATURE
<222> LOCATION: (1)..(280)
<223> OTHER INFORMATION: HUS1

<400> SEQUENCE: 12

Met Lys Phe Arg Ala Lys Ile Val Asp Gly Ala Cys Leu Asn His Phe
1               5                   10                  15

Thr Arg Ile Ser Asn Met Ile Ala Lys Leu Ala Lys Thr Cys Thr Leu
            20                  25                  30

Arg Ile Ser Pro Asp Lys Leu Asn Phe Ile Leu Cys Asp Lys Leu Ala
        35                  40                  45

Asn Gly Gly Val Ser Met Trp Cys Glu Leu Glu Gln Glu Asn Phe Phe
50                  55                  60

Asn Glu Phe Gln Met Glu Gly Val Ser Ala Glu Asn Asn Glu Ile Tyr
65                  70                  75                  80

Leu Glu Leu Thr Ser Glu Asn Leu Ser Arg Ala Leu Lys Thr Ala Gln
                85                  90                  95

Asn Ala Arg Ala Leu Lys Ile Lys Leu Thr Asn Lys His Phe Pro Cys
            100                 105                 110

Leu Thr Val Ser Val Glu Leu Leu Ser Met Ser Ser Ser Arg Ile
        115                 120                 125

Val Thr His Asp Ile Pro Ile Lys Val Ile Pro Arg Lys Leu Trp Lys
130                 135                 140

Asp Leu Gln Glu Pro Val Val Pro Asp Pro Asp Val Ser Ile Tyr Leu
145                 150                 155                 160

Pro Val Leu Lys Thr Met Lys Ser Val Val Glu Lys Met Lys Asn Ile
                165                 170                 175

Ser Asn His Leu Val Ile Glu Ala Asn Leu Asp Gly Glu Leu Asn Leu
            180                 185                 190

Lys Ile Glu Thr Glu Leu Val Cys Val Thr Thr His Phe Lys Asp Leu
        195                 200                 205

Gly Asn Pro Pro Leu Ala Ser Glu Ser Thr His Glu Asp Arg Asn Val
210                 215                 220

Glu His Met Ala Glu Val His Ile Asp Ile Arg Lys Leu Leu Gln Phe
225                 230                 235                 240

Leu Ala Gly Gln Gln Val Asn Pro Thr Lys Ala Leu Cys Asn Ile Val
                245                 250                 255

Asn Asn Lys Met Val His Phe Asp Leu Leu His Glu Asp Val Ser Leu
            260                 265                 270

Gln Tyr Phe Ile Pro Ala Leu Ser
        275                 280

<210> SEQ ID NO 13
<211> LENGTH: 524
<212> TYPE: PRT
<213> ORGANISM: Homo sapiens
<220> FEATURE:
<221> NAME/KEY: MISC_FEATURE
<222> LOCATION: (1)..(524)
```

<223> OTHER INFORMATION: PGBD5

<400> SEQUENCE: 13

```
Met Ala Glu Gly Gly Gly Ala Arg Arg Ala Pro Ala Leu Leu
1               5                   10                  15

Glu Ala Ala Arg Ala Arg Tyr Glu Ser Leu His Ile Ser Asp Asp Val
                20                  25                  30

Phe Gly Glu Ser Gly Pro Asp Ser Gly Gly Asn Pro Phe Tyr Ser Thr
            35                  40                  45

Ser Ala Ala Ser Arg Ser Ser Ser Ala Ala Ser Ser Asp Asp Glu Arg
50                  55                  60

Glu Pro Pro Gly Pro Pro Gly Ala Ala Pro Pro Pro Arg Ala Pro
65                  70                  75                  80

Asp Ala Gln Glu Pro Glu Glu Asp Glu Ala Gly Ala Gly Trp Ser Ala
                85                  90                  95

Ala Leu Arg Asp Arg Pro Pro Arg Phe Glu Asp Thr Gly Gly Pro
            100                 105                 110

Thr Arg Lys Met Pro Pro Ser Ala Ser Ala Val Asp Phe Gln Leu
        115                 120                 125

Phe Val Pro Asp Asn Val Leu Lys Asn Met Val Gln Thr Asn Met
130                 135                 140

Tyr Ala Lys Lys Phe Gln Glu Arg Phe Gly Ser Asp Gly Ala Trp Val
145                 150                 155                 160

Glu Val Thr Leu Thr Glu Met Lys Ala Phe Leu Gly Tyr Met Ile Ser
                165                 170                 175

Thr Ser Ile Ser His Cys Glu Ser Val Leu Ser Ile Trp Ser Gly Gly
            180                 185                 190

Phe Tyr Ser Asn Arg Ser Leu Ala Leu Val Met Ser Gln Ala Arg Phe
        195                 200                 205

Glu Lys Ile Leu Lys Tyr Phe His Val Val Ala Phe Arg Ser Ser Gln
    210                 215                 220

Thr Thr His Gly Leu Tyr Lys Val Gln Pro Phe Leu Asp Ser Leu Gln
225                 230                 235                 240

Asn Ser Phe Asp Ser Ala Phe Arg Pro Ser Gln Thr Gln Val Leu His
                245                 250                 255

Glu Pro Leu Ile Asp Glu Asp Pro Val Phe Ile Ala Thr Cys Thr Glu
            260                 265                 270

Arg Glu Leu Arg Lys Arg Lys Lys Arg Lys Phe Ser Leu Trp Val Arg
        275                 280                 285

Gln Cys Ser Ser Thr Gly Phe Ile Ile Gln Ile Tyr Val His Leu Lys
    290                 295                 300

Glu Gly Gly Gly Pro Asp Gly Leu Asp Ala Leu Lys Asn Lys Pro Gln
305                 310                 315                 320

Leu His Ser Met Val Ala Arg Ser Leu Cys Arg Asn Ala Ala Gly Lys
                325                 330                 335

Asn Tyr Ile Ile Phe Thr Gly Pro Ser Ile Thr Ser Leu Thr Leu Phe
            340                 345                 350

Glu Glu Phe Glu Lys Gln Gly Ile Tyr Cys Cys Gly Leu Leu Arg Ala
        355                 360                 365

Arg Lys Ser Asp Cys Thr Gly Leu Pro Leu Ser Met Leu Thr Asn Pro
    370                 375                 380

Ala Thr Pro Pro Ala Arg Gly Gln Tyr Gln Ile Lys Met Lys Gly Asn
385                 390                 395                 400
```

Met Ser Leu Ile Cys Trp Tyr Asn Lys Gly His Phe Arg Phe Leu Thr
            405                 410                 415

Asn Ala Tyr Ser Pro Val Gln Gln Gly Val Ile Ile Lys Arg Lys Ser
                420                 425                 430

Gly Glu Ile Pro Cys Pro Leu Ala Val Glu Ala Phe Ala Ala His Leu
            435                 440                 445

Ser Tyr Ile Cys Arg Tyr Asp Asp Lys Tyr Ser Lys Tyr Phe Ile Ser
        450                 455                 460

His Lys Pro Asn Lys Thr Trp Gln Gln Val Phe Trp Phe Ala Ile Ser
465                 470                 475                 480

Ile Ala Ile Asn Asn Ala Tyr Ile Leu Tyr Lys Met Ser Asp Ala Tyr
                485                 490                 495

His Val Lys Arg Tyr Ser Arg Ala Gln Phe Gly Glu Arg Leu Val Arg
                500                 505                 510

Glu Leu Leu Gly Leu Glu Asp Ala Ser Pro Thr His
            515                 520

<210> SEQ ID NO 14
<211> LENGTH: 1107
<212> TYPE: PRT
<213> ORGANISM: Homo sapiens
<220> FEATURE:
<221> NAME/KEY: MISC_FEATURE
<222> LOCATION: (1)..(1107)
<223> OTHER INFORMATION: POLD1

<400> SEQUENCE: 14

Met Asp Gly Lys Arg Arg Pro Gly Pro Gly Pro Gly Val Pro Pro Lys
1               5                   10                  15

Arg Ala Arg Gly Gly Leu Trp Asp Asp Asp Ala Pro Arg Pro Ser
            20                  25                  30

Gln Phe Glu Glu Asp Leu Ala Leu Met Glu Glu Met Glu Ala Glu His
        35                  40                  45

Arg Leu Gln Glu Gln Glu Glu Glu Leu Gln Ser Val Leu Glu Gly
    50                  55                  60

Val Ala Asp Gly Gln Val Pro Pro Ser Ala Ile Asp Pro Arg Trp Leu
65              70                  75                  80

Arg Pro Thr Pro Pro Ala Leu Asp Pro Gln Thr Glu Pro Leu Ile Phe
            85                  90                  95

Gln Gln Leu Glu Ile Asp His Tyr Val Gly Pro Ala Gln Pro Val Pro
        100                 105                 110

Gly Gly Pro Pro Pro Ser Arg Gly Ser Val Pro Val Leu Arg Ala Phe
    115                 120                 125

Gly Val Thr Asp Glu Gly Phe Ser Val Cys Cys His Ile His Gly Phe
130             135                 140

Ala Pro Tyr Phe Tyr Thr Pro Ala Pro Pro Gly Phe Gly Pro Glu His
145                 150                 155                 160

Met Gly Asp Leu Gln Arg Glu Leu Asn Leu Ala Ile Ser Arg Asp Ser
            165                 170                 175

Arg Gly Gly Arg Glu Leu Thr Gly Pro Ala Val Leu Ala Val Glu Leu
        180                 185                 190

Cys Ser Arg Glu Ser Met Phe Gly Tyr His Gly His Gly Pro Ser Pro
    195                 200                 205

Phe Leu Arg Ile Thr Val Ala Leu Pro Arg Leu Val Ala Pro Ala Arg
210                 215                 220

Arg Leu Leu Glu Gln Gly Ile Arg Val Ala Gly Leu Gly Thr Pro Ser

-continued

```
              225                 230                 235                 240
        Phe Ala Pro Tyr Glu Ala Asn Val Asp Phe Glu Ile Arg Phe Met Val
                        245                 250                 255
        Asp Thr Asp Ile Val Gly Cys Asn Trp Leu Glu Leu Pro Ala Gly Lys
                        260                 265                 270
        Tyr Ala Leu Arg Leu Lys Glu Lys Ala Thr Gln Cys Gln Leu Glu Ala
                        275                 280                 285
        Asp Val Leu Trp Ser Asp Val Ser His Pro Pro Glu Gly Pro Trp
                        290                 295                 300
        Gln Arg Ile Ala Pro Leu Arg Val Leu Ser Phe Asp Ile Glu Cys Ala
        305                 310                 315                 320
        Gly Arg Lys Gly Ile Phe Pro Glu Pro Glu Arg Asp Pro Val Ile Gln
                        325                 330                 335
        Ile Cys Ser Leu Gly Leu Arg Trp Gly Glu Pro Glu Pro Phe Leu Arg
                        340                 345                 350
        Leu Ala Leu Thr Leu Arg Pro Cys Ala Pro Ile Leu Gly Ala Lys Val
                        355                 360                 365
        Gln Ser Tyr Glu Lys Glu Glu Asp Leu Leu Gln Ala Trp Ser Thr Phe
                        370                 375                 380
        Ile Arg Ile Met Asp Pro Asp Val Ile Thr Gly Tyr Asn Ile Gln Asn
        385                 390                 395                 400
        Phe Asp Leu Pro Tyr Leu Ile Ser Arg Ala Gln Thr Leu Lys Val Gln
                        405                 410                 415
        Thr Phe Pro Phe Leu Gly Arg Val Ala Gly Leu Cys Ser Asn Ile Arg
                        420                 425                 430
        Asp Ser Ser Phe Gln Ser Lys Gln Thr Gly Arg Arg Asp Thr Lys Val
                        435                 440                 445
        Val Ser Met Val Gly Arg Val Gln Met Asp Met Leu Gln Val Leu Leu
                        450                 455                 460
        Arg Glu Tyr Lys Leu Arg Ser Tyr Thr Leu Asn Ala Val Ser Phe His
        465                 470                 475                 480
        Phe Leu Gly Glu Gln Lys Glu Asp Val Gln His Ser Ile Ile Thr Asp
                        485                 490                 495
        Leu Gln Asn Gly Asn Asp Gln Thr Arg Arg Arg Leu Ala Val Tyr Cys
                        500                 505                 510
        Leu Lys Asp Ala Tyr Leu Pro Leu Arg Leu Leu Glu Arg Leu Met Val
                        515                 520                 525
        Leu Val Asn Ala Val Glu Met Ala Arg Val Thr Gly Val Pro Leu Ser
                        530                 535                 540
        Tyr Leu Leu Ser Arg Gly Gln Gln Val Lys Val Val Ser Gln Leu Leu
        545                 550                 555                 560
        Arg Gln Ala Met His Glu Gly Leu Leu Met Pro Val Val Lys Ser Glu
                        565                 570                 575
        Gly Gly Glu Asp Tyr Thr Gly Ala Thr Val Ile Glu Pro Leu Lys Gly
                        580                 585                 590
        Tyr Tyr Asp Val Pro Ile Ala Thr Leu Asp Phe Ser Ser Leu Tyr Pro
                        595                 600                 605
        Ser Ile Met Met Ala His Asn Leu Cys Tyr Thr Thr Leu Leu Arg Pro
                        610                 615                 620
        Gly Thr Ala Gln Lys Leu Gly Leu Thr Glu Asp Gln Phe Ile Arg Thr
        625                 630                 635                 640
        Pro Thr Gly Asp Glu Phe Val Lys Thr Ser Val Arg Lys Gly Leu Leu
                        645                 650                 655
```

```
Pro Gln Ile Leu Glu Asn Leu Leu Ser Ala Arg Lys Arg Ala Lys Ala
            660                 665                 670

Glu Leu Ala Lys Glu Thr Asp Pro Leu Arg Arg Gln Val Leu Asp Gly
        675                 680                 685

Arg Gln Leu Ala Leu Lys Val Ser Ala Asn Ser Val Tyr Gly Phe Thr
        690                 695                 700

Gly Ala Gln Val Gly Lys Leu Pro Cys Leu Glu Ile Ser Gln Ser Val
705                 710                 715                 720

Thr Gly Phe Gly Arg Gln Met Ile Glu Lys Thr Lys Gln Leu Val Glu
                725                 730                 735

Ser Lys Tyr Thr Val Glu Asn Gly Tyr Ser Thr Ser Ala Lys Val Val
            740                 745                 750

Tyr Gly Asp Thr Asp Ser Val Met Cys Arg Phe Gly Val Ser Ser Val
        755                 760                 765

Ala Glu Ala Met Ala Leu Gly Arg Glu Ala Ala Asp Trp Val Ser Gly
        770                 775                 780

His Phe Pro Ser Pro Ile Arg Leu Glu Phe Glu Lys Val Tyr Phe Pro
785                 790                 795                 800

Tyr Leu Leu Ile Ser Lys Lys Arg Tyr Ala Gly Leu Leu Phe Ser Ser
                805                 810                 815

Arg Pro Asp Ala His Asp Arg Met Asp Cys Lys Gly Leu Glu Ala Val
            820                 825                 830

Arg Arg Asp Asn Cys Pro Leu Val Ala Asn Leu Val Thr Ala Ser Leu
        835                 840                 845

Arg Arg Leu Leu Ile Asp Arg Asp Pro Glu Gly Ala Val Ala His Ala
        850                 855                 860

Gln Asp Val Ile Ser Asp Leu Leu Cys Asn Arg Ile Asp Ile Ser Gln
865                 870                 875                 880

Leu Val Ile Thr Lys Glu Leu Thr Arg Ala Ala Ser Asp Tyr Ala Gly
                885                 890                 895

Lys Gln Ala His Val Glu Leu Ala Glu Arg Met Arg Lys Arg Asp Pro
            900                 905                 910

Gly Ser Ala Pro Ser Leu Gly Asp Arg Val Pro Tyr Val Ile Ile Ser
        915                 920                 925

Ala Ala Lys Gly Val Ala Ala Tyr Met Lys Ser Glu Asp Pro Leu Phe
        930                 935                 940

Val Leu Glu His Ser Leu Pro Ile Asp Thr Gln Tyr Tyr Leu Glu Gln
945                 950                 955                 960

Gln Leu Ala Lys Pro Leu Leu Arg Ile Phe Glu Pro Ile Leu Gly Glu
            965                 970                 975

Gly Arg Ala Glu Ala Val Leu Leu Arg Gly Asp His Thr Arg Cys Lys
        980                 985                 990

Thr Val Leu Thr Gly Lys Val Gly Gly Leu Leu Ala Phe Ala Lys Arg
        995                 1000                1005

Arg Asn Cys Cys Ile Gly Cys Arg Thr Val Leu Ser His Gln Gly
        1010                1015                1020

Ala Val Cys Glu Phe Cys Gln Pro Arg Glu Ser Glu Leu Tyr Gln
        1025                1030                1035

Lys Glu Val Ser His Leu Asn Ala Leu Glu Glu Arg Phe Ser Arg
        1040                1045                1050

Leu Trp Thr Gln Cys Gln Arg Cys Gln Gly Ser Leu His Glu Asp
        1055                1060                1065
```

```
Val Ile Cys Thr Ser Arg Asp Cys Pro Ile Phe Tyr Met Arg Lys
    1070                1075                1080

Lys Val Arg Lys Asp Leu Glu Asp Gln Glu Gln Leu Leu Arg Arg
    1085                1090                1095

Phe Gly Pro Pro Gly Pro Glu Ala Trp
    1100                1105

<210> SEQ ID NO 15
<211> LENGTH: 33524
<212> TYPE: DNA
<213> ORGANISM: Homo sapiens
<220> FEATURE:
<221> NAME/KEY: misc_feature
<222> LOCATION: (1)..(33524)
<223> OTHER INFORMATION: CLSPN

<400> SEQUENCE: 15
cggctgaggg aatcagagac agctccgtcc ctagtggagc gcaggggagg cagaagtcat      60
gacaggcgag gtgggttctg aggtgagttt atgcacacgc cccccacggg ggcttagaag     120
gccgggcacc gagaggttag gtggggccgg ggtagacccc gctgacccga ggcgcccggg     180
cgggaggact gcggctcccg gcgttcgccg cgccggctcc cgcggcctcg agactcggcc     240
gggatgggtt ccgaccgggc atcccgtccc gccgcgggc ttcccgcgct cgggctccg      300 tggccggaga gctccaggtc tctgcggcgc gcactgccgg cagcccagcc cctcttcagc     360
cggttcctgc cgccagccct ccctttggc gcgtttcctg tcgcggaagc tcctcccctc      420
agggtgctct gaaagccggg aggctctagc cgaacccggc cgcagcggtg cgggggatt      480 ctccgcagag agagggcgag cgagggtgtt agggagttcc acactgggcc tgggaggggc     540
cctggaggtc atcgcgcgca ggcccttttgc gttttccgac cgggcccga gtggggaagt      600 caccgctggg gctcctggct ggtggctggc agctccctgg cgaaattggg catagaaaac     660
agatgtttcc agagctgtgt cctttctggg ccggattcgg gcaaggcact cccgccttag     720
gagcaaaatt taagggcg ccaaaaccct caatcaaact catattttaa tgcaatattt       780
ttaaaaaacc aaaattaatg caaaaacttt ttatgatttg atattgaaca aaatatcaga     840
cgtttaaaca aagacgagat ccgaccagtc atttgcacga ccttgcctca atcacctcac     900
cctaattcca tccctgtttc caataaactt tatttacaaa agcgggcata ttatttacct     960
catgagctgt agattattga tttaattttt taaaaaatat tgcattaatg ttattcattt    1020
tgattactga atttttgag acctcacccc accctgttac tggccctgcc ctttgacgtt     1080
gctgcaaatt gcctagaaga taatcgtcat tcaaagcagc cctattcctt gagctgtctg    1140
gttacctaaa ttcggtttcc acactcacaa acagaagtaa tagttttact gctttggatt    1200
gttgagagga tcatcagtgc atacatatta attctcagca atcccagcac ttcgggaggc    1260
taaggccggc agattgcttg agctcaagag ttcgaaacca gcctgcatag aaaacatggc    1320 aaaacccgc ctctacaaaa aaaaaaaaat tagccgggcg tcgcctgtgg tcccagctac     1380
tcggtcccag ctactcgggt ggctgaggtg agagaatcct ttgggcctgg gaggtcaagg    1440
ctgcagtgag ccatgatcct gccactgcac tccagcctag gtgacagagt gagacactgt    1500
atcaaaaaaa aaaaaattt gtaccttgca ttcaaatcaa tttaataatt tttttttttt     1560
tgagacggag tctcgctctg ttgcccagac tggagtgcag tggcacaatc tcggctcact    1620
gcaacttctg tctcctggat tcaagcgatt cctgccccc agcctcctga gcagctggga    1680
ctacaggcac acaccaccac gcccagctaa tttttgtatt tttagtagat acggggtttt    1740
```

```
actgtattgg ccaggctagt ctcgaactcc tgaccttgtg atccacccac ctcggcctcc    1800
caaagtgctg ggattacagg cgtgagccac catgcctgac caatttaata attttttgag    1860
aaaccactca gctgaggcct tgtgccctgt tacattactg atgttcatat ttctcccttt    1920
attaataagt tgattcagag ccctgagaac actaaggagg tagacttggc atctagggtt    1980
agctttaagg tcactaactg atcaagtcac ctaacacacc cctcctcctt aggtttttat    2040
ttgcgacttt ttaaactgtc ttatttagaa attttcaaac ctatacaacc gtagaaagga    2100
tggtataatg aacccatcac cttacttcaa ctacagtttg aatatctctc gtctgaaatg    2160
cttgggacca gaagcgtttt gaatttcaga ttcattttgg attttggaat attcgcatac    2220
acataatgag atatcttggg ggagggaccc aagtctaaac atgaaattca gttatatttc    2280
atatatacct tacacacata gtctgaaggt aattttatac agcattttaa aataatttcg    2340
tgcatgaagc aaaggtttta ctgcagctca tcatatgagg tcaggtgtgg aattttcatc    2400
tagtggcatc atgtcagtgc tcaaatattt tggaattggg agcatttcag attttcaggt    2460
tagagatgtt caacctgtat tttcaagtca tggccaatct tgttttattc atacagctac    2520
ccatttttcc tctcacagga ttatttggaa gaaaatccaa gatatcatat tatttgaacc    2580
acaaagattt tagtgtgcat atctaacaaa caagagcttt ccaaaaatag atactacgat    2640
attattacca cacctaagaa gtatctagtc agtgttcaga tttctttgac tcagagatat    2700

ttcatttatt tttatatgcc actttagcat aatттaтттac atttttagtt ttttgaatca    2760
tcatccgaag ttggcatttt gtaattgttt atattatata tgtgtatata tgcatatatg    2820
tatgtatttt aagatataca tacatatata aagcatacat ttatgtatat agaaatatac    2880
agggccggtt gtggtggctt acgcttgtaa ttccagcatt ttgggaggct gaggcaggcg    2940
gatcacctga ggtcaaaagt tcgagaccag cctggctaac attgtgaaac cccgtttcta    3000
caaaaaatta gccgggcatg gtggcacgca cctgtaatcc cagctactcg ggaggctgag    3060
gctggagaat cgcttgaacc caggaggcgg aggttgtagg gagccaagat cgtgccattg    3120
cactccagct tgggcaataa gagcgaaact ccgtctcaaa aaagaaaaa aggaaatata    3180 catatagccg ggcgtggtgg ctcacgtctg taatcccacc actttgggag ctgaggcgg    3240 gcggatcacc tgaggtcagg agttggagac cagcctgact aacatggaga accccatct    3300

ctactaaaaa tacaaaatta gccagacgtg gtgacacatg cctgtaatcc cagctactcg    3360
ggaggctgag gcaggagaat cgcttgaacc tgggaggcag aggttgcggt gagccgagat    3420
cgcgccgttg cgctccatcc tgggcgacaa cggcaaaact ccatctcaaa aaaaagaaa    3480

tatacacata gcatatagaa atatacatac atatataaat atatagaaat atacatacgt    3540
acacacatat atacattcac ttatgtgtta actttcttta taggtttctc tccctctctt    3600

ttttttttct ttgcaatata ttgttaaaga accggccgg gtgcagtggc tcatacctgt    3660 aatcccagca тттttgggagg ccgaggtggg cggatcacct gaggtcagga gtttgcaacc    3720
ggcctggcca gcatggtgaa accttgtctc tattaaaata gaaaaaatta gctgggtgtg    3780

ttgatgtgcg cctgtaatcc cagctactca ggaggctgag gcaggagaat cgcttgaacc    3840
caggaggcag aggttgcagt gagccgagat tgcaccactg cactccagcc tgggtgacag    3900
agcgagattc tatctcaaaa aaaaaaaaaa aaagagaga gagagagaaa gaaaccaccc    3960
agtttgactt gтagaaттттc ccacgtctag attgcatatc tgtggtatta ttcaacatgt    4020

tcccctattc cctctatttc ctataacttg ctagttagat ctagagactt gataggattc    4080
aaatttgatt gttctgtcag gaatacttta tggctagtat tgggtacttc tattaggcag    4140
```

```
cacataatgt ctggttgttt ctcttttggt gatgttagca gccattaatg ataattgcct      4200
aggtctgtta tttaattgag ggttgataaa attgtgataa tctaattcta tcatttatta      4260
attcattagg atatttctct aaatagaaac ttcccctcat caattgtatg gatatattgg      4320
ggaacagttc acacagaaaa ggcataataa atgcttgatt cttttcattt ttttttttac      4380
cgttactaaa agagttggtt ctgttagcat ccttcaaagg tgaaaaatga acttttgttt      4440
gtttgttgtc cagtaattct aaatgtcatc ccttcaagga accattgtat ttggttcttt      4500
ccttagttca ggttgatgat cccacgatga tttgtgtgtc attatgtact tggagctttc      4560
ggtcacctgc tggttgatat aaagtatatt gtcattttct aggttcacct agaaatcaat      4620
gacccaaacg tcatttcaca agaggaagca gatagtcctt cagatagtgg acagggcagc      4680
tatgaaacaa ttggacccct gagtgaagga ggtttgtaat agtactttta tttttaggaa      4740
taggttgcgg gagcctcagt tgtaagtaga ttggattgat ttcattattc tcttgattta      4800
ttacattatt aatgccccat ccttattgtt tgttttatta taaagcaaa ataacagtgc       4860 ttgtaccttt ttgaaactat gttatattgt tgaatgtcta atagctacca tattgcctgg      4920
ttaattgcat tcatcctata ataaaaggaa ttttaacacc tgccggaggt tagaacaact      4980
ttacacattg taaatatacg taaaattaca tttcccagta agagacattt tcccaggga       5040 aaatgttttt caaatgtat  ttttagattt gctttgctac aatcagttct taacagtagt      5100
cacgtaattt cacaatgtta tatatcactt gtataaaaat atattttga ggagtagtgg       5160 gactaggagg aagatcaaat gatggtataa ttaaaagaaa attgtttcct ccagattcag      5220
atgaagagat atttgtaagt aagaagttga aaaacaggaa ggttctacaa gacagtgatt      5280
ccgaaacaga ggacacaaat gcctctccag agaaaactac ctatgacagt gccgaggagg      5340 aaataaaga gaatttatat gctgggaaaa atacaaaaat caaaaggatt tacaaaactg       5400
tggcagacag tgatgaaagt tacatggaaa agtctttgta tcaggaaaat cttgaagcgc      5460
aagtgaaacc ttgcttagag ctgagtcttc agtctggaaa ctctacagac tttaccactg      5520
acagaaagag ttccaaaaag cacatacatg ataaagaagg aactcagga aaagcaaaag       5580 taaaatcaaa aagaagactt gagaaagagg agagaaaaat ggaaaaaatt agacagctaa      5640
aaaagaagga aacaaaaaac caggtacatt ttaaagaata atttgctatt gcttgggtag      5700
gttaacattt tagaaaaggt tgctgttagt acttgaggtt gtttctgctc tctgactatt      5760
gctttgaatt gactattttg tgttgagaat tattctcaat aggtatgtga tttaaaacta      5820
actggtcttg gccaggtgca gtggtgcata cgtctaatcc cagcactttg ggaggctgag      5880
gccagagggt cacttaagcc caggagttcg agaacagcct aggcaacaga gtgagatccc      5940
atctctacaa aaaatttaaa aattagttgg gtgtggtggc cgtagtccca gctgtagtcc      6000
caactacttg ggagggtgag gtgggagaat cacttgagcc caggaagtcg aggctgcaat      6060
gaagctgtaa ttgtaccact gcattccagc ctggatgaca gagtgagacc ctgtctcaaa      6120
aaaaaaaaaa acaaaaacca aaaaacaaaa acttattggt cttattctat tttgggtatg      6180
cagaggacat ttccaaataa atgggtttct gattttcttt atgagcacat ggagtaattc      6240
tttgctgtct ctgagctgat gaaaattaac tgaaagaagg cttttttatg catctatcag      6300
tcagtagtct tgtttgctaa ctagaaaaac catcctcaaa tttataaact agttgcttaa      6360
caagtatttt acttcaaaaa aatatttact gtttattaag ttagtttag acagttgcat       6420 aaaatcacaa cttggacttc aaaggataca tgtgagttag aaaccagtaa gaatgttcta      6480
```

```
gattttatat gcttgtctgt tgatgaaaca tgggcttttt ctggcctgat ccaaattgcc      6540
atatgatgtt gtgaaatact ggatttttaa atgattggat tatgcttttt gtttatgtat      6600
tacttaggaa gatgatgtag aacagccatt taatgacagt ggctgtcttc ttgtggataa      6660
agacctrttt gaaactgggt tggaggatga aaataactct ccattggaag atgaagagtc      6720
attagaatca ataagagcag ctgtaaaaaa caaagtaaaa aagcacaagg caagtaaagc      6780
atgattgcaa taagagttaa tcaactgctt ctgacctttg ctatattttt aatttactgt      6840
tggaacctta attttttttt taactgaaga aaaacttgtg tcagttgact taagtgtttc      6900
agctgttaat tttggagact tgcagtacaa gtgatagaca tgctaacttc tttgaaaact      6960
agtgttttgt tattaccctt ttaggaatgc tgaaaaaaaa aaccactaag atatttgatg      7020
gtgtagtaag atgcaggtaa ataataggga agagatgtaa attttgcaat cctatagcct      7080
ttgagaaatg aaccctatag ggtttcagga agggtatcaa agagaggcat cagtcaaaac      7140
attgttgtcc cgagtgtttg gaagcataat ttttcttcct aagatttttt tttagcttcc      7200
tgcgagttat tatccctctt tagggaaga tgtaagcaga ggtaaaagaa ataagggtcc      7260
agactccatc tgaggtatct gttttctaag cataatagga tgctgtgtgt ttaataattt      7320
ctagttgatg attattgatt tattaatgta gcatgatgtg gtgttggact acaaaagtag      7380
tcttcagcta aagcatcctc ttatttgaat ttcgtttttg tcctaatcaa cctgccattt      7440
cttttagaaa aagaaccat cttcggagag tgggtccat tcatttgagg aaggaagtga      7500
gttatcaaaa ggaaccacga ggaaggtgag gtagagccct gtatattagt cacactgatc      7560
tctttacaca ggagattata gatttcttag ggataaatat tttattttgt ctatcatatt      7620
tttctgttac ccatcatatt gctttgtaca tagtaggaac aaaatatgga ttggattgaa      7680
caaattctct gagacttggg aataaatgaa ttccttgagt ttatactgca tttgggctta      7740
ctcatgctta ctatttcctt tcctcttttc ttggagagag caaactcttg agtgatgaat      7800
atctatcttt ctggatattc atataattaa tgtagtctca cттcттgтттт tctttaagga      7860 aagaaaggca gccagattaa gtaaagaagc attaaaacaa ctgcatagtg agactcagcg      7920
ccttattcga ggtaatgcaa cccagtaaac tttgaggcaa aatcacaaca tttctttgta      7980
agctcaactt ggatgttggg gacttttatt ттттттaacac ttctaatgtg aactcaggtt      8040
ataatattaa gttagaatt gatcttggtg aaaggccatt gttctaaagc ccttggaaca      8100
ttagtataaa ctgaagaaat tttcagaact gtagtgcagg taaggaggaa атттттттaaт      8160 ggttgtctat ggactgattg tgtcaggatt ctttggagag gtagtaatcc ctccctattt      8220
gcagttttgg ttacctgtgt cagccatggt ccatggaact taaaaatatc ATCCCTttgt      8280
ccagagtatc acgctgtata cattacctgc ctgttagtcc gttagtagcc ctctcagtta      8340
tcagatcaaa aaaacactgc atggtttagt accatctgca gtttcaggca tccactgcag      8400
gtcttggaat gtgtctgtct ggataagcgg ggactactgt atataatgt ttaggtccca      8460 cagagattct gattcagtag attcgaaatg ggatccaaga atctgtattt ctaaaaaact      8520

tcctggatca тттттgaтттc acatctaggt ttaaaagcca ctggtcttca gggagctttt      8580

ттgтaccттag ctcctctgcc ттттgттaaag gggagttttc tattctagt gatgctttg      8640 gttattatgt ttagttaact gaatatgaag tgacatttca gaatatacag tattatattt      8700

tgcttgtttt attccatttt atagagtctg cactgaacct tccatatcat atgcctgaga      8760
ataaaaccat tcatgatttc ttcaaacgta accccggcc cacttgccac ggaaatgcca      8820

tggcactatt gaagtaagaa ccctctttcc ttattataat tttcatgaac atttagtttt      8880
```

```
gtagcaaaca tctggcataa aaagttcaga tttctcactc ccttaaaact gatttaactg    8940
atatatacta agggatgaga atgtttcaca tttaggataa ttttcaactc cagctcaatt    9000
tctcttctct aggtcatcta aatatcagtc aagccatcac aaagaaatca tagacactgc    9060
aaatactact gaaatgaaca gtgatcacca tagtaaaggt tctgagcaga caacaggtgc    9120
agaaaatgaa gtggaaacta atgcactccc tgtagtttca aggaaaccc agatcattac     9180 tggatcagat gagtcttgca ggaaggattt ggtaaaaaat gaagagctag aaattcagga    9240
gaaacagaag cagagtgaca ttagaccttc acctggggac agctcagtgt tgcaacagga    9300
atccaacttc ctcgggaaca atcacagtga ggaatgtcag gttggagggc ttgtagcatt    9360
tgaacctcat gccctggagg gtgaaggccc ccaaaatcca gaagaaacag atgagaaagt    9420
ggaagagcct gagcagcaaa ataaatcatc agcagttggg ccacctgaaa aagtgagacg    9480
gtttactctg gatagactta agcaactggg agtagatgtt tccattaaac cacggctagg    9540
tgctgatgaa gattcctttg tgatacttga acctgaaacc aacagaggta atcctttaca    9600
ttgtggggag cctccctgga gtgattatcc tggtagcttt tgattattga ctactgtcga    9660
ggacagagaa cacaggagga accaataacc actttgatct tatcctgcag ttgttccaga    9720
tatgggcaga gtctttttta gagaaatttg gcagggtatc agaatgatct aagccatgtt    9780
taaaatggaa gtctgttggc tgggtgcggt ggcttacgcc tgtaatccca gcactttggg    9840
aggccaaggc gggcagatca cgaggtcagg agtttgagac tagcctggcc aatacagtga    9900
aaccccgtct gtactaaaaa tacaaaaatt agccgggcat ggtggcacgc atctgtagtc    9960
ctagctactc gggaggctgg ggcaggagaa ttacttgaac ccagaaggca gaggttgcag    10020
tgagccgaga ctgcaccatt gcactccagc ctgggtgaga gagcgagact ctgtctcaaa    10080
aaaaaaaaaa aaaaaaaaag gttgttgata gttaatataa aaaagaggta cattgctact    10140
gtgttatggt atttaggaat ttattatttc tgcctttcca atctgaaatt aagttttttc    10200
tgtaatcctg agtcaaatct taagacattg atgaaaacat catttagttt tttactgcta    10260
aagagaaaca ttttggttca cttaaattat ctgtgaaacc gaatttcttt tgttttcact    10320
cattcaacaa atattaaagt atctactatg agtaagttgc tgtggggcat accaagataa    10380
atctgacatt taaggtatac ttaagatgct tttactctaa tgggcgagat aagaagtatg    10440
caaataagaa gtacaaagga gaaatggta aatgatgtct ttgataatga atatgtcatt      10500
gataattgga aaataaataa catgaagaaa aaggaaaagt attttcttaa agaacattta    10560
gaataaagta ctgtgggaat tcagagaagc ataaatttct tccaatgaat agttaaagaa    10620
cagcctgaag aataggtgga ttaattactt gttcactgcc ttcccttat actgtgagtt      10680 ggtatcttct gccttgttcc ctactctatc cctagtgctt cctcagtgga cgacacattg    10740
taggcacttg tatttatcaa atgaatgaat gatccctcaa cactgaactc aagtattacc    10800
acattgaata aatttcctga ctcttagata gagctggatg ctccccactc tgccttgagg    10860
cagtatggaa tggtggttaa gagcttagac tttgtagcaa gaccaggatt tgaatctgaa    10920
ctagcatagt aattgtttaa cattgtatac gccatttgac ctcttcaagc atcttttgtt    10980
taaaaaagag aagaaagcca gacacagtgg tgcacacctg tagttccagc tactcgggag    11040
gctgaggcac aagagggtca cttgaaccca ggagtttaag gccatcctgg gcagcatatg    11100
aaatcctgtc tcaaaaaaaa aaaaaagaaa aagaaaaaa gcactatatg acttgtgggc     11160
tatggtgaag atttgttgaa ataatgcatg caaatggata gtataaacaa gcactcaaaa    11220
```

```
agttgttgct gcttctacta ttattagtga aatggttcac atcaagactt ttttttttttg   11280
agacgggctt tcacttgctc ttgccaccta ggctggagtg caatgctgcg atctcggctc   11340
actgcaacct ccgcctcctg ggttcaagca attcttctgc ctcaggctct caagtagctg   11400
ggattacagg tacccgccac cacacccagc taattttgt atttttagta gagacagggt    11460
ttcaccatgt tggccaggct ggtctcaaac tcctgacctt aggtgatctg cctgcctcag   11520
cctcccaaag tgctgggatt acaggtgtga gccactacac tcagccaaga ctctttcatt   11580
aaaccaagca tagtcagtgg cttatgcctg taattctagc actttaggag gctgaggtgg   11640
gaggattgct tgagcccagg aggtcaaagc tgcagtgagt tgtgagctga aattgcactc   11700
ctgcactcca gtctgggaga cagaacgaga ccctgtctca aaaaaaaaa aaaaacacaa    11760
aaaaattatc tttcattaaa catcttattg ttggcaggtg ctatgtcagt gactatatct   11820
ggtgtgtaaa atatgctcag tgagtctgtt aattgaatgg gttgactttg gagatggaga   11880
ggatagaaag agcaccttgt ctcattaaaa caaaagaaa aacaaacac acacaaaaaa    11940
gattctgttt cattaaacag cttattgttg gcaagtgcta tgtcagccac tgtatctggt   12000
gtgtaaaata tgcttagtga gtctgataat tgaatgggtt gactttggag atggagagaa   12060
ggacagaaag aactctgcat ggtggtgcgt attgggaaga tgtgaaagtc actttgacca   12120
gggctggagg ttcaggtggc agagttgtat aacagaacta gcatagctcc attagcaaag   12180
aagcatgaga ataagctgtt gtccggaaca ctgagggaaa gttttgtta tatgggacta    12240
aaagttacct aaacagtcct agactgatag gaaagggaga acatttttt gagtaccaac    12300
tatattagac actggtacat tctttgttag ttgtctttct taattctcac agtgccaggt   12360
attattttgc aaaatgaaga gactgaggct cagagaggtt aggtaatttt tccagcatta   12420
tacttggctt ataaagggac ctacacagtg gctggcatat aatgagcact tattttttaa   12480
cttggaacat gttttccttt agaaataatt gacacgaaat ttgggtttcc agaccagcca   12540
taatatacat gaagttagaa tcaacattca ttcattcatt catgcaataa actttatttt   12600
agcactgtgt tgggtgctgt gtatacacgt aaaacactcc ctgctctcaa agaaattgaa   12660
gtgtaatagg agtgatagac aggcaaacag accattacaa tactgatgg taagtgctgc    12720
gatcaaggta tataattgag ggtgcattgg gaacctagag gaagggtacc ttacttggag   12780
cctagaagtc agggaagttt ctgaaatgag ctcagtagag ataccaaggc agagaggtga   12840
gggagggctt ttttggtgga ggggttggac ctgcagatgt cagagacaat ggaaagcaca   12900
gggtgatctc cctggctgaa gtgaagatag caaggacatt ggtgatcaga gcccagatca   12960
ttcagggttt ttatgccatg ctaggagctt ggactttagc tctttgtaag tagaggacca   13020
ctgaaaggtt ttcagcaaag gaaatgttca atcagatact cactttagga agttaaatct   13080
ggtagctgtt gtggtggatg cattggaagg ggttaagagt aaaaacagtg gaacagctc    13140
agtttcttta cctcatatag aataaggttt ccatgagaaa atgcatgtaa atttaaattt   13200
tgtgatgtca gaaatacatt atttctgttg cttgcaatag catatggaat aatccctgcc   13260
tctaattcct ctactttctg gacaagagca atgtgaatga gaacagttct tatgctgctg   13320
atagagataa gctaggaaag agacttttca cttaagagag gagatgagag gtgatggagg   13380
atgagaggtg atggactaat agagatgaat ggaggtagag gaacttgaac aggggtttta   13440
ggatgaagac agtgatggtt gcatcatgta ataaaggcca agaaagtgg ttgctccaat    13500
gggttggggg aggaagagct ttgaggatcc tagcttctc cagttatgaa tgaagatacc    13560
tcttgcctga ctactatttt aagtcccagg taatcttccc acccaaccat ttctcttacc   13620
```

```
ctagtggcac ccataataac ctgcctattt ctgttccctt ttccctgcta ccacctgttg   13680 cttttcagctt tactgaacca ctgcaaaata ggaggcagac ttacagcttg tctctctact   13740
cttttgtttg caatgtaaac ataccatcct ttagagttgg gttttttgctg ctaataatgt   13800 tggggtttca ggataaaaag atttccttca ttttttctctt tttctagtaa gaccgtctag   13860
aggaaaaaaa cacatctaga tgctagtcac aaaaacaccg aagtatgatt tgagtgcatt   13920
ttagaaaatt agtcaagttt catgcctata gtcccagcac tttgggagac taaggtggga   13980
agttcgcttt gaggccaggt gtttgagacc agcttgggca acatagcgag ttcctgtctt   14040
tacaaaaaat aacaaagcca gatgtggtga catgcacctg tagtcctagc tacttgggag   14100
ggtgaggtag gaggaatgct taaacccagg aggtcaaggt tgcagtgagc tgtgatcgca   14160
ccactgcact ccagcctgag caacagagca agaccctgtc tctaaaaaga caaatgaaaa   14220
gtggctgggc acaatggctc acacctgtaa ccctagcact tgggaggct gaggagggtg   14280 gatcatttca gtccaggagt tcaagaccag cctggacaac atggcaaaac cggtctctac   14340
aaaaaataca aaaatcggcc agtcgcagtg gctcactcct gtaatctcag cactttggga   14400
ggccgaggtg ggtggatcat ctgagatcag gagttcaaga ccagcctggc caacatggtg   14460
aaaccccatc tctactaaaa ataaaaataa aaaattagc tgggtgtggt gacgcatgcc   14520
tgtaatccca gcttctaggg aggctgaggc aggagaattg cttgaaccca ggaggtggag   14580
gttacagtga gccgagatca tgccactgca ctttggcctg gcaacagag tgagactccg   14640 tctcaaaaaa aaaaaaaaaa aattagctgg atatggtggt acatgcctat agtcctggct   14700
atctcaggag gctgaggtga gaggatcacc tctaagcttg gggagattga ggctacagtg   14760
agagccaaga ttgcaccact gcactccagc ctgggcgaca aagcgagact ccatttaaaa   14820
ataaaccatt ttatcatgga cgagaaggcc gcctgaaaat atccagtgtg catcaactcc   14880
aaaggaactt tctccttaaa actgccagct ctcatcacag attccattat gatatgaagt   14940
gttaagcaga gtgagtaggg attggttcca ggtaacagct agctgaggga aaggaaatt   15000 ctaagatatt gcagtgggga agaggggtaa gtttatatca ctattggatt gctgaactta   15060
ctgttcccag tatatatata tttccgtttg tatacaagtt gagcatgtgg tactgggct   15120 gcagtatttt cttctctcatt gtaccaattg tactagtgta acagttttca ccaaaaaact   15180
ttttacagtc ctgctgctta gttatatcac tgactggatt gtcattttat tttcccttct   15240
tgaaaaaaat tgactttgcc tatattagt aagattgcca ataatgaaac attcaaaata   15300
gggaatttga tcccagcact ttgggaggcc aaggtgggct gatcatttga ggtcaggagt   15360
tcgagaccag cctggctaac atggtgaaac cctgtctcta ctaaaaatac aaaaaaatta   15420
gctgggcatg gtggtgctca cctgtaacct cagctactca ggagactgag gcaggagaat   15480
cgcttgaacc ctggagatgg aggttgcagt gagctgagat cacatcactg cactccagcc   15540
tgggcaatag agtgagactg catctcaaaa caaaaacaaa aacagcaat aacaaatagg   15600 gaattttaaa aggagaccaa aacccatgaa aaattaagcc cttgaataga tgagattata   15660 atctttttc ctaccagttt aatacttta aagaatttt aaagaatgtt caaagaatt    15720 gcacatattt agaaatttca ggtataaatt tctgtctgat ttttaaagt ctgattttg    15780 aaacgttgag gaagaacagt tgtggcagtc aattagtttg ggttaagttg tatgaattg    15840 actcaggagt tagtagcaag gggttttggg ttctctgtg tatgtgtggt ttccctcata    15900
attgttgagc taaaaaaaac ttagcttata agtcttaaag gaaagagttt tgagcatggc    15960
```

```
aaactgacac actggttggc gtttgggttt agaactggaa gccttgaagc agcgtttctg    16020
gaagcatgct aatccagcag ccaaacccag ggctggtcag acagtgaatg tgaacgtcat    16080
agtgaaagac atgggcactg atggaaagga agagctaaaa gcagatgtgg tacctgtgac    16140
tttagcacct aagaagttgg atggagcaag ccacacaaaa ccaggtattt gagcccacag    16200
gttttgtttt ttgcttttg ctttgtattc taacagatct tcaaggctat tgaaaacctt     16260
ataatgaaaa gttatagaat cttttcctt ggaggctttg cagagcagta tctctggcat     16320
gattcacgtg tagcacacct agaggtgtgg ggtggacaag ctggctttat tttttttta    16380 gatatcattt gtcttattat aaaaaacccc attatagaca aatatataga ataaatgaaa    16440
aacttaatct tctatcagag acaggttcta taaccatatc gtgtatcctt ttaaactctc    16500
ttctttgcac atatgtatat gtaatttaaa caaaaacagg ctgggtgcag tggcacatgc    16560
ctgtaatcct agcactttgg aaggacaagg caggaggatc tgttgagctc aggagttgga    16620
gaccagcctg gcaacatag tgagccctca tctctaccaa aaaaaaaaaa ttatccaggc     16680
atggtggcct gcacctgtgg ccccagatac ttgggaggct gagacaggag gatcatttga    16740
gccaggaggt tgaggttgta atgagtcatg attgtggcac tgcactccag cctaggcgag    16800
agagtgagac cctgtctcaa aacaaaaaac ccaaaacaaa acaacccacc tataatgtga    16860
tcataacatg cattctgctt tgtgttttag aaatgtatta aggacagctc tcaccctcc     16920 cttgaaatca caagtaatat atcacatgga aaacagtttt aaacactgaa aaaaggtatc    16980
aaatgaaaaa ctagtcttcc caaagataac tattaacaat ttcttgtatg tctttatagg    17040
agtattttta tccatatacc gtattttgtg aatgtgtgtg acattgaaca tttactccct    17100
gtcaggcatt gctctaggtg ctttatatgt tttatctcat ttaatcctta caaccctatg    17160
aggtaaataa cattagtatc cttattttgt atatgaagaa actgatatgc agagcactta    17220
agacacttgc tcaagtttac acagctaata aatggtagga ccagtagtct aatccagacc    17280
acctaactcc agagctcaga tctactttat attgcttttg aggcttttt ttttttttt      17340 ttttttcctc taagacagag tcctgcactg tcaccctggc tggagtgcaa tggcacgatc    17400
ttagctcact gcaacctcta cctcctgggt tcaagtgatt ctcctgcctc agcctcccga    17460
atagctggga ttacaggtgc ctgccaccat gcctggctaa ttttttgtatt tttagtagag    17520 atgaagtttc gctatgttgg ccaggctggt ctcgaactcc tgacctcgtg atctgcccac    17580
cttggccccg caaagtgctg ggattacagg cgtgagtcac tgcgcccggc cttgaggctt    17640
tttttaaaat ggctgcataa tattccattg aatgaataca acatgactca ttaaaccata    17700
ctcgtattga cagatgtctt gtttgttcca gttgttgcta ttgcatacag tgttatatta    17760
tagtgccaga tatatggtgg tatattagat gaaaattcct tacagtggaa ttgtcatgat    17820
atatatcaca ttttgatata tatcatccag ttgtctttca gaatggttgt accactctga    17880
atcacagtgt atgagttcct gtttcctctc aataggtatt atcaaacctt ctaattttg     17940 ccaggctaac atgtcgaaaa tgtatctcgt tattttgatt tgtagctctt caattagaag    18000
tgagattaag cattacttt aatttattaa caatatatgt ttattttcg tgaactgcca      18060 gttcatatca ttagctcatt ttactcgagt cgtttctctt tttctttaat ataggtaaat    18120
ttatcaatgt ttttcttcat ggcttttgag ccacagactt gaagctctac tccctaccca    18180
ccttttctct cttttgaaca attatttat aatccctgag tagtatacta tctagggtgc     18240
agaagttctc tttgatactt caattcataa taatactctt gtgttcaaat aacaaaaaag    18300
cccagaatac tagagtctca gattttcctt ttgggatgtg actagaatat ttctggagtt    18360
```

```
gcctaaaatg catacctaat tattgtatta tgtctaaagc atttctacat atttctgttc   18420
aggtgaaaag cttcaggtgt taaaagctaa actgcaagaa gcaatgaaac tccgaaggtt   18480
tgaggagcgc cagaagcgcc aagcactgtt taaattagat aatgaagatg ggtttgagga   18540
agaggaggag gaagaggaag aaatgacaga tgagtctgag gaagatggag aagagaaggt   18600
agagaaagaa gagaaagagg aagaactaga ggaagaggag gagaaagaag aggaggagga   18660
agaagaagga aatcaggagg tttctggcaa ttacgttgtt ttgttaccttg gtcatggtga   18720 atatgagaga aaaagtcaga cttgaaaaag agtataataa gcatgttcaa ttgtataaga   18780
ggttttaggg gcatgatgag ggtaactacc tcatatatcc ctaaatctta ggaacttcag   18840
ttctgtcagt accactgaat atctgtagat catcattata tatctgaata cagatattca   18900
gtggtactga cagaatacca ttgcctgggc ttccacctgt ttatatattt taatataata   18960
atgctaatat taaaaatggc tttgtattcg taggaaattt tatctttgtt gtttatttag   19020
gtttctctag cagattaaaa agcagtccta accttggcta gattgaggcc tggagtaaat   19080
tcttagggag gtagaggcct ttctgagtta ttttcgttct ttgtagaaga aggcatttgt   19140
agaagggcct cttgcccttg ttccgtagta ctgttttctg cctagggaaa acaggtgatg   19200
atacgattgt taagtattaa aaaactttcc tttttgggcc gggcagggtg gctcatgcct   19260
gtaatcctag cactttggaa ggctgaggta ggtggatcac ctgaggtcag gagtttgaga   19320
acagcctagc caacatcgtg aaaatccatc tctactaaaa atacaaaaat tagctgtgtg   19380
tggtggcaca cacctgtaat cccagctact caggcaggag aattgcttga acttgggcag   19440
tgaaggttgc agtgagccaa gattgtgcca ctatactcta gcctgagcga cagagcaaga   19500
ctgcatctca aaaaagaaa aaaaaaaaaa aactttcctt tttgtatgct gggatcactt   19560 tatttttattt tattttatttt atttatttaa attttttga gatgagggtc tcactatgtt   19620
gaccagactg gtctcgaact cctggcctca agtgatcctc ccatcgttgt ggcctcccaa   19680
agtgctggga ttacaggcat gagccaccat gcccagcaac ttgagttatt atttaatttt   19740
gggtaaagga gaaagaaagc aatggctgag ctatacagcc tgtctcagtc tgtgcttggt   19800
ttgagatcag tagtcagcct gcaatcttag actgattaat taacctctta ctgcctcaat   19860
aaaatgataa tccagtcgtc ctttataatc ttagcaattt cgggagggta gaaggtaaaa   19920
aaaaaaaata gaaaaaagtt ctagaagtgt cagggaaaat tatgttgata atggtcatat   19980
ggaacttcct tcaagtttac cttttttgaat ttaagatgtg atctgtaacc aatcagccat   20040
atttcaggct accagtgtat ttgcttttaa atgttttgac ttgtatttt tgttttgtgg   20100 tggcctgatt ggtaaagact gcagaattcc ttcttagtag tgaagaaata gaaacaaaag   20160
atgaaaaaga aatggataaa gaaaataatg atggcagtag tgaaattggc aaggcagttg   20220
gcttcctctc tgttcccaag tctctctcat cagattctac tttacttctg tttaaggaca   20280
gctcttccaa gatggggtaa gtgattctct ctaagaaaac ttaaaattgc cttggatttg   20340
cccctcctgt aaaaactagg aacagatact gaaccaattt actttcttat tttgcagtta   20400
ctttcctact gaagaaaaat cagaaacaga tgaaaactca gcaagcagc ctagcaaact   20460 gggtaagtag tgattcttgt gcagaactta acatttcttt tgtccctcag ctttgatatt   20520
taaggactgc agtacggtaa gtttccatgt ttttaaatct ggtcacttcc cagtttcata   20580
tgtagctatg aaaagggttt atgaattaga atatttttct tggtctattt tttgcagttt   20640
atttatagta gaccatggta cataatgtcc ttagtgaatg tgtgttgatt gagtgagcaa   20700
```

```
tgaaatgttt ctgtatgtag atcaaaggaa gacgtataat tgattggaca atgaagagtg   20760
tgatcatagg cattaggaag gataagagaa agaagagaac tttcggccag gcgcagtgac   20820
tcacgcctgt aatcccagca ctttgggagg ctgaggcagg cggatcatga ggtcaggaga   20880
tcgagaccag cctggctaac atggtgaaac cctgtctcta ctaaaaatat aaaaaattag   20940
ccaggtgtgg tggcacgcgc ctgtagtccc agctacttgg gagggtgagg caggagaatc   21000
gcttgaacct gggaggcgga ggttgcagtg agccgaattc acgccactac actccagctg   21060
gggtgacaga gcgagactgt ctcaaaaaaa aaaaaaaaa aaaaaaaga actttcaagt    21120 gtcacttagc tcagagtaat aagccctgat tatataatgc tatcttagta ctgtaattta   21180
cctttaactt aatgttttgg aacatataac ttgaggggtt tgcctatgaa ttttatctga   21240
cagtttcatc ctcaactctt tttcctaaac aaatccacct tatttctgta atcatgtgct   21300
taaaaggtgt ttctctttct ttagatgagg atgattcatg ttcattgcta acaaggaga    21360 gcagccacaa tagcagcttt gagctgattg gctccacgat tccatcctat cagccttgca   21420
acagacaaac aggccgtggg accagttttt tccctacagc aggaggattc agatctcctt   21480
cccctgggct atttcgagcc agtttggtca gctcagcttc taaggtaaga tggtaatggt   21540
ttttctaatc tcctcctctc tttgcttccc acattgctaa ataaagtttg tcccagccaa   21600
ccaactccca ccacgttggt actgagctta tgtgtgttca gtttaaaaaa tccacccct    21660 ttgtgtatta aaaacaagct tcatccagta ttcttacttt cttggaggta tttttcttta   21720
tgcttctcat ggctgtgtat tgtccccctc aactacaatt tcctgagagt agcttaaata   21780
ttgcaaatag caacttttgt ggttgtcatg acaatgactg acatttgtaa aatgttttgt   21840
tattgtttgt ttttgtttgt gtgccagagt tcagggaaac tgtctgagcc ttcacttccc   21900
atagaggatt cccaggatct gtataacgcc tccccagagc ctaagacact tttcctagga   21960
gcaggagact tccagttctg tttagaagat gacactcaga gccaactgtt ggatgcagat   22020
gggtaggtag ttttgtgttt ctgtgggcgg aatggtgct gggtactgct taattttgtt    22080
taaaaataag tgagcttctg tcactccatc tgtgctttct cttctgagaa agagaaggtg   22140
tacagaccat tagtattaca ttctataagt ttgaacaaag tctgtccaga aaataaacat   22200
aaatagctct tgctaacatt ctggtccttc aatttctgtc ttatttgaaa tgcatagatc   22260
ttgtattgta aggtcatcaa atttccctgt atccatcctg ctatgttatt attgttgggt   22320
aaggttgaga attcacagac tggtggcaca ttacaggaca taatgccaag ccctgctcta   22380
gcatcatctg aagctaaaag ttatccttta cactttacct tctgagtaac attttattct   22440
ttcacaaaac ttttccctcc ctctttagat taacacaagc ctaaagtttg aatcttttgc   22500
tttctggttt gagattcagc ttttaactgg tgtaggaaat gaattcagag gtttttcacc   22560
ccctactttg ccatttctct gaggaatttt tttttatttt ttttttgag gcagagtctt   22620 gctctgtcgc ccaggctgga gtgcagtggc gcgatctcgg ctcactgcaa gctccacctc   22680
ctgggttcac gccttctcc tgcctcagcc tcccgaatag ctgggactac aggcgcccac    22740
caccacgccc ggctaatttt ttgtattttt agtagagacg gggtttcacc atgttagcca   22800
ggatggtctt gatctcctga cctcgtgatc cgcccgcctc ggcctcccga gtgctggga    22860 ttacaggcgt gagctaccgc acccggccct ctctgaggaa ttttttacac tattcgttgt   22920
gctcattggt tcttaggttc ttaaatgtta gaaaccacag gaatcagtac caagctttga   22980
agcctcgatt gccattggcc agtatggatg agaatgccat ggatgccaac atggatgagc   23040
tgttggattt gtgtactgga aagttcacat ctcaggctga aaaacatcta cccaggaaga   23100
```

```
gtgacaagaa agagaacatg gaggaacttc tgaacctttg ttcaggaaaa ttcacttctc    23160
agggtaaata tccaaccgag agtatcaagc ttaccacacc caagtatcag tgcccttgaa    23220
aagaattccc tgggcgggtg gggtggctca tgcctgtaat cctagaactt gggaggcta     23280 agttggatgg atcgcttgag ctcagaagtt tgagaccagc ctgggcaaca tggcaaatcc    23340
ccatctctac gaaaaaaaaa aaaaaaatta gccaggcatg gtggcacgtg cctgtggtcc    23400
tagctacttg ggaggctgag gtgggaggat ctcttgagcc tgggagatga aggttgcagt    23460
gagctgagat cacaccagtg cactccagcc tgggtggcag agaccctgca taaaaataga    23520 aaaaagaaa gaaagaaaag aagcccctta ccctcaggtg aaaagttcac agaaaacagg     23580
gctgtgatgg aatctgtgta taaactgaat tcactgctta gtgccctgat atttagaact    23640
cttactttct tagagtggta aagtatcaac ttaagactac tttaggccgg gcgcagtggc    23700
tcacgcctgt aatcccagca ctttgggagg ccaaggcggg ggatttcctg agctcaggag    23760
ttcgccacca gctgggcag cacggtgaaa ccccgtctct actaaaatac aaaaaattat     23820
ctgggcatgg tggcccgtgc ctgtaatcgc agctacttgg gaggctgaga caggagaact    23880
gcttgaaccc cggaggtgga ggttgcagtg agccgagatt gtgccactgc actccagcct    23940
gggcaacaga gagagactgt ctcaaaaaaa aagtcttgaa aaaaaaaaag actgctttag    24000
cttgccccat atatcattta tgattaatgt atgtacaaag tttagaacag tgtctgatgt     24060
ataataaatt tcatataaat gttaacttac ttcctgttcc ctgcccccaa tacacacaac    24120
tgctagatcg aacataagct ctatgagacc tgggatagtg gtttgttcat tactgtatcc    24180
ctggtggcct ggcacatatg gcacatagta agcactaaat aaggatttgt tgaatgaata    24240
gatggtaggc tcttcttggc aagcttacct tagaactgta tcgagctggc atgactttag    24300
atggctggga aaagagtata aagctatcat tccttggtga cacatctttt ccttgttgtg    24360
atgtagatgc ctccactcca gcctcatcag agttaaataa acaggagaag gagagcagca    24420
tgggtgatcc aatggaagaa gcacttgctc tttgctcagg ctcttttccc acagacaagt    24480
aagtctcaga ttgctgggaa ttgggaagg cctggccttt tgataaaatc aaaataactg     24540
atcatcttaa gggctttgca ccttttctga gaatcttgca gtggatttga gtctcatata    24600
tgcctagtaa gcaaattata atgctttggt ggagaacagg gtaaaaaagg caagaatatg    24660
aaagctattt aatatcatta atagagaaat gccaatcaaa accatagtga cacccatt     24720 aagatgactt ttatcagaaa aaccccaaga gtgttagtga gaatgtggag aaattggaaa    24780
ccttgtgtac tattggtgag aatgtaaaat agtgcagctg ccagggaaag tatgatggct    24840
cctcaaaaat taaaaataga ggccaggcac ggtggatcat ctgaggtcag gagttcgaga    24900
ccagcctgac caacatggtg aaaccccgtc tctactaaat acaaaaaatt agctgggcat    24960
ggtggcgcat gcctgtaatc ccagctactt gggaggctga ggcaggagaa ttgcttgaac    25020 ccggaggca gaggttgtag tgagccgaga tcatgccatt gcactccaac ctgggcaaca    25080
agaacaaaac tccgtctcaa aataaataaa taaaaataga atgaccatat gatccagcaa    25140
tttcacttct tagtctgtac cccaaaaaag tgaaagcagg acttgaacag atatttgcac    25200
ccccatgttc aaagcagcat tattcacagt aagtagtcaa acatgaaag cgacctatgt     25260 ttattggcaa atgaatgggt aaacaaaatg cggtatatat gcaaaggaat attcaactta    25320
aaatggaaat tctggctggg catggtggct cacacgtgta atcccaacac tttgggtggc    25380
tgaggtgggc gcatcacttg agctcaggag tttgagacca gcctggataa tatggcaaaa    25440
```

```
ccccatccct ataaaaaaaa tactaaaatt agctaggcgt gtgccggcag taccagctat    25500
tcagggggct gaggtgggag aattgcttga gcctgggagg tcaatgctgc attgagccat    25560
gattgtgcca ctgcactctg gcatcagag caagaccctg tctcaaaaaa aaagaagttc     25620
tgacacttgc tacaacatgg atgaaccta gaatgttatg ctaaaagaaa taagccagtc     25680
accaaaagac aaatactgta tgagtccact tacatgagat acttagagta gtcaaatgca    25740
tagagacaga aggtagaatg gtggttgcca gagactgagg ttataaggaa atggagagtg    25800
taatgggtat agagttttag ttttgcaagc tgaaaagagt tctggagatt gcttaacaat    25860
atgaatgtac ttaacactac agaactatag aaagatcgtt aaaaaggcaa attttatatt    25920
atgtgtattt taccacaatt gaaaatttaa aaaattttct tcctgtttat tgaagagatt    25980
attggtgata ataaaagttt taaatttggc tgggcgaggt ggctcatacc tataatccca    26040
gtactttggg agcccaaggc aagcagattg cttgaatcca gaaattcaag atgaacctgg    26100
gcaacatggt gaaatctgtc tctacaaaaa tacaaaaatt agctgaacat ggtggcttgt    26160
atctctagtc ccagctactc aggaggctga tgtgggagga tcacttgagc cctggaggtg    26220
gaggttacag tgagctgaga tggtgccact gtattccagg tggtgtaaga accaagact     26280 gtctcagaga aaaaaaaaaa attaacacac acaaaatttt ttttaattca taacttggct    26340
gactacttgt agtttgcttt caacaactta tttattgatt cattgattta cattttaggg    26400
aagaggaaga cgaggaggag gaatttggag actttcggct tgtttcaaat gataatgagt    26460
ttgatagtga tgaggtgagt atgaagggaa caaagtaatc ataactgagc tccatgtatt    26520
gctgccctca agtgtttttt tcccctcagt tcttgagaat tctaagtttg gcatcttatc    26580
agaaacaatt tcctagaatg aggtatttgg gcagatgttt ataaatcctt ttttcattga    26640
ggacgcattt tattctgctt aatttggata tgatgctgat tttgtaggat gaacacagtg    26700
actctggtaa tgatctggca ctggaagacc atgaagatga tgatgaagaa gaactcctga    26760
agcgatctga gaagttgaaa aggcaaatgt acgtgttatt aatatgtcca ttccttcagg    26820
tgtatttaaa atttggtcac taggccaggc atggtggctt gcgcctgtaa tcccatcatt    26880 tgggaggct gaagcaggcg gatcacctga ggtcaggagt tcaagaccag cctggtcttg     26940
gtgacacagg tcaagagatc gagaccatcc tgacaaacat ggtgaaaccc tgtctctact    27000
aaaaaatata aaaattagcc agatgtgatg acaggtgcct gtagtcccag ctactcagga    27060
agctgaggca gggagaatcg cttgcaccca ggaggtggag gttgcagtga gccgagatcg    27120
caccactgca tttcagcctg ggtgacagag cgagactctg tctcaaaaaa aaaaaaaaa     27180 aaaaagttga tcacttaata tgtcctgtgt gctaataact gtgctttaca ggcattaaca    27240
tattatctta tgccaggcac agtggctcac gcctgtaatc ccagcacttt gggaggccaa    27300
ggcaggcata ttacttgagg tcaggagttt gagaccagcg tgaccaacat ggtgaaaccc    27360
tctctactaa aaatacaaaa tacaaaataa aatacaaaaa ttagccaggc atggttctgg    27420
gcgcctgtag tgccagctac ttgggaggct gaggcaggag aattgcttga atatgggagg    27480
cggaggttgc agtgagccaa gattgcccca ctgcactcca gcctgggtga tagagcaaga    27540
ctccatctca aaaaaattat cttatgagtg ggtactatta ttctcctcat tttacagttg    27600
aaggaactga gcctcagaaa gattaaattt acccaagatc acatagctag aaggcagcag    27660
aggctggatt caacttagat taggtgaaat ctcccctaac agtcagttaa tagtttgcca    27720 cttttttaact taaatcctcc tgcctcagct tcccaagtag ctgggacaac aggcatgtgc    27780
caccacacct ggctaattct ttctattttt tgtagagatg gggccttgct tgttcccag     27840
```

```
gctggtctta aactgttggc ctcaagtgat cctcctgcct ctgcttccca aagtctggga   27900
ttacaggcat gagccaccag gcccagcttt tttttttttt tttttttttt tttttgagac   27960
ggagtctcgc tctgtcgccc aggctggagg gcagtggcat gatctcggct cactgcaacc   28020
tccgcctccc gggttcaaag cgattctcct gcttcagcct cctgagtagc tgggaatata   28080
ggcacgtgcc accacaccca gctaattttt gtatatttag tagagacggg gtttcaccat   28140
gttggtcagg atggtctcga tctcttgacc tcacgatcca cccgccttgg ccttccaaca   28200
tgctgggatt acaggcgtga gccaccccac ctggccggcc caactcattt ttttgatatg   28260
ctgttctggt catgaaagta aaatatttat tttaggatat ttaaaagaat acaaactggg   28320
tgcagtggcc cacgcctata atctcagcac tttgggaagc tgaggcgggt ggatcacctg   28380
aggtcaggag ttcgagacca gcctggccaa catggcgaga ccccgtctct actaaaaata   28440
caaaattagc caagcgtgat ggccagtgcc tgtaatccca gctactcagg aggcaaagct   28500
ggagaatcgc ttgaaccggg aggtggaggg tgcagtgagc tgagattgtg ccattgcatt   28560
ccagcctggg cgacgagaga actccattc tccccgaccc ccgcaaaaaa agaatacaga   28620
aagatataaa taaaaactta tccatgtcca ccatccagga tataaatgaa agttagtttg   28680
ttccccttaa tctttttat gcatatattt ttatatagtt gagatttgta caatctttct   28740
atatgtataa ttttgcatct tttttttct acttagcata tccagaaaca ttttcctatg   28800
atgttaaaaa aagttttata aagataattc taataggtat ttaatattat attgtatgtg   28860
aatgatttgg aattcacata taggacatca tattgatccc tattagattt atatggttgc   28920
ttttatccca tcatttcatt ctattaagat tcactttggg ttctaattta tcacctatca   28980
aattaactct catacagctt taggttatcc atagattttt ctaaggtagt ggttcttctc   29040
tgcagagctc tttgttcaaa taaatctttt taaagaatga cagataaaag ttgaactgtt   29100
caaagatggt aagtgggaag tttgggaaac ttagtgacta gtggcctctg aaggaatttt   29160
ccaggaactc taggatttag aacaacttag ctttaagaaa atacagtata ggctgggcgt   29220
ggtggctcat gcctgtaatc ccagcacttt gggaggctga gatggacaga tcccctgagg   29280
tcaggagttc aagaccaccc tggccaacat ggtgaaaccc tatctctact aaaaaaacaa   29340
aaattagcca ggcatggtgg cacgcacctg taatcccagc tactcgggag gttgaggcat   29400
gagaatcact tgaacccagg aggtggaggt tgcagtgagc cgagatggca tctctgcact   29460
ccagcctagg cgacagagcg acacttcatc tcaaaaaaaa aaaaaagag aaaatacagt   29520 ataggtcttc gataaaaatc agttttcaga aagccaccaa acttctgcca ttttggacca   29580
catgggacca aggtgacttt gaatccaggg tgacaccaga tttattctcc gggggagctg   29640
aagtcataag aagtaactag tcgttttgat taccaggagc tctgagcctt agtcttcctt   29700
ctgatgtggg ggtcaagatt tgttaggctg taagaagatc ccagtttatt acctttctac   29760
accacaccat ctctagtttg tctcttaaag ctggtgtgct caaatgcaaa atgaaatagt   29820
ttgaaccttc cagcaggtat tctaatacat gtaaaagaga ttaagagttt tctggctttc   29880
aaatcaccca atctaagttg aatccaggct ctgctaccttctagctatgt gaccttgggt   29940 aaatgtaatc tttctgaggc tcaattccct caactgtaaa atgaagagaa taatagtacc   30000
cattcctatg ataatatgtt aatgcctgta aagcacagtt attagcacac aagacatatt   30060
aagtgatcaa cttttaaata cagatgctcc acatcttaca atgggactat atcctgatca   30120
atccatcata agttgaaaat gcactttcat attatccaga tataactcca tcgtaaatcg   30180
```

```
agaagcatac taagtgcgta tcacattcat gtcatcgtaa agttgaaaaa tcattaagtc    30240
aaaccatcat aagtggagac tattacaaaa aaatttaaat attatcaaat gtattatgtt    30300
tattattatt agaagtgact ctgttctgct tttctttgct tccatattct gtgagtatat    30360
tcattgttgc attttctaat cctcaaaatt gctttctagg aggttgagga atacctgga     30420 ggatgaggca gaggtgtcag gaagtgatgt gggaagcgaa gatgagtatg atggggaaga    30480
aattgatgaa tatgaagagg acgtaattga tgaagtactt ccttctgatg aggaactgca    30540
gagtcaaatc aagaaaatac acatgtcagt atcccaataa gcccttctga gtaatagggt    30600
acatcttaag acaagccctg taaccagcca gaatggtcct tgttttgaac accttatttc    30660
tcctgttgca ggaaaactat gttggatgat gataagcgac agctacgttt ataccaagag    30720
aggtaccttg ctgatgggga tctgcacagc gatggtcctg ggcgaatgag gaagtttcga    30780
tggaaaaaca taggtatctt ggttgttgtc tttaaaagca atcagttacg ggctgagcat    30840
ggtggctcac gcctgtaatc ccaacacttt gggaggcaga ggcaggtgga tcacaaggtc    30900
aggagttcag gaccagcctg aacaacatgg tgaaaccccg tccctactaa agttcaaaa     30960 attagcaggc tgtgatggca cgcgcctgta atcccagcta ctcaggaggc tgaggcagga    31020
gaattgcgtg aacccgggag acggaggttg cagtgagcag agatcatgcc attgcactcc    31080
agcctgggcg acagagcgag actccatctc aaaaaaaaaa aaaaaaaagc aaacagttac    31140
aatgcatatt tgtcgagttt cagatggcaa atggcaagca aaactataac aggctatgtg    31200
aagacctagt tgtaactgtt ttctgttaat ggatgggaaa agtttacatc attatatagt    31260
aaatgataag ggtttatttt ttgtctgtcc aagcaccctc tcctgtgagg actgccgaat    31320
gctgattacc ttcactcttt gtttagatga tgcttcccag atggacttgt tccacagaga    31380
ctctgatgat gatcagactg aagaacagct tgatgagtca gaagccaggt ggaggaagga    31440
gcgaattgaa cgagagcagt ggcttcggga catggtagga gttcacctac tctgacccta    31500
gtttatgaga ctgtccctta gcttgtcatg atagtttcaa atcttagct tgtcatgata     31560 gtttcaaaat cttaggcaac atattgctat ctcttttaat ccttgagcta tcttttgtgt    31620
tttgagaagg ctataccata gacagttctc ttcatgtttg tctaagatta attttttttt    31680
gtctaaagca gcaaaggctg caaaaaggaa aacaaatacc ccaggaactc tagtttcaca    31740
atccaggcca tgctaactat ttaggaaggt tatagacttt taatgctgta tatatatata    31800
tatatatata tatttttttt ttttttttca ggcacagcag gggaaaatta cagctgaaga    31860
agaagaagaa attggggagg acagtcagtt tatgatactg gccaagaaag ttacagccaa    31920
agcactgcag aagaatggtg agctcttgtt tctccttagg gtctagcccc ctggattgtt    31980
agtggtagag ctttggaggt gactctaacc ttcaggagct gttgcagctt aatcataagc    32040
ttgtgtctaa tactgtctta aagaggcttc acagaggtgg tgggagacag tgtacttaga    32100
tcttagacta ttgggcagta gagactgtat tcatgagtat atgtggctgg ttttactta     32160 tgttctaagg ctcagagtag ttaattctgg ctttctctag ttgcccagga ttgtatacct    32220
aagtgttaga ggtaggattt gaatccagga atatttaact ccagaaatga agctcttcac    32280
tattccctac actgaccact tctgttttc ttaaatgatt actgttcaac ttagttgtgt     32340
ctcttcttgg agccaattat tatagtttga aagtcaccat tatatagaac agagttccca    32400
tggctttagc atattgattt agttacaaga tttcttagct tgtttagatt taaaagtaat    32460
tctaatcagc ttttcccaga ataggcctct ctgtcttttc tttccagcca gtcgccctat    32520
ggttattcag gaatcaaagt ctttgctcag aaatcctttt gaagccatca gaccaggaag    32580
```

| | | | | | |
|---|---|---|---|---|---|
| tgctcaacag | gttggttggg | aaccttgtta | atctgacatc | atagtctaca | ggttataaag | 32640 |
| gcccaggtcc | agcttagaga | atagtctctg | tcattagagg | aaggaggtgg | ctgcagggaa | 32700 |
| aaagttaatg | tcaaaggagt | ctgctatttc | ttttctattt | gaatagggta | ggcatatgta | 32760 |
| ccctcaatat | ctaggggaa | gcagggaggg | aaggactttt | cattctttag | ttggcacttg | 32820 |
| ggatttgata | ccagatgact | cttctttcct | caggtgaaga | caggctcact | gctaaaccag | 32880 |
| cccaaagctg | tgcttcagaa | actggctgct | ctctctgacc | ataaccccag | tgctcctcga | 32940 |
| aattcaagaa | actttgtctt | tcatacactt | tctcctgtca | aggctgaggc | ggcaaaggaa | 33000 |
| tcgtctaagt | ctcaggtatg | gaatttgaga | actaatatgg | tggcttccca | aaccagaatt | 33060 |
| tattcattta | tttaaattta | aaaacaaaaa | ttctggctta | acctctatgc | tgcaatgttg | 33120 |
| aaatcttgca | ctccccgata | aggtacaaga | gaattgctac | cccagtcggt | aatcaacttt | 33180 |
| taaacttgcc | gagaaagttt | atctttcttt | cttttttct | gttgttaatc | atccacaatt | 33240 |
| tatgagttgc | ttgagagcta | attgaaggta | aatacttgta | tgaaggtctt | tagctggccc | 33300 |
| tgactccctc | tctgctctct | aggtaaagaa | aagggtcca | tctttcatga | cttctccttc | 33360 |
| acctaagcac | ctcaaaacag | atgatagcac | ttcaggattg | acgcgaagca | tcttcaaata | 33420 |
| tttggagagc | taacaccatc | aaaggtgcca | aaatctacat | tgagactgct | ttgagaagtt | 33480 |
| tctagcactg | aaagttggaa | ttgacactcc | agccaatgat | cctt | | 33524 |

<210> SEQ ID NO 16
<211> LENGTH: 17171
<212> TYPE: DNA
<213> ORGANISM: Homo sapiens
<220> FEATURE:
<221> NAME/KEY: misc_feature
<222> LOCATION: (1)..(17171)
<223> OTHER INFORMATION: MAD2L2

<400> SEQUENCE: 16

| | | | | | |
|---|---|---|---|---|---|
| gaggaggggc | ggcgggtggc | gggctcgact | gccccagcc | gaggggcagc | ccgggggccg | 60 |
| ggcccggcgc | gcacccggcc | agcgcgcccct | cgccagctgc | gctctgagtt | ctgggccagc | 120 |
| tccccagagg | cctaggcgcc | gccgccgcga | gggcgcgggg | cagacaaagg | aggcagacaa | 180 |
| aggcgggcgc | agcccagcag | ccgtgcgggc | accgggcgag | gcaggcccac | tcctcccggt | 240 |
| gcgtaagagc | cgcctcggcg | cggcccaggg | cgcgtgggac | gggaggggct | ccggcagttg | 300 |
| tggcgcctct | ggagcggccc | cgcgcagggc | gggcgacaaa | gggccgcggc | gggcggtcct | 360 |
| cggtggaccc | caacaatgga | gcgaggctgc | gcgctcagct | gcggccgcgt | ctgtcagggc | 420 |
| aggggcccgg | ggccacaaaa | ggattattcc | gcctagactg | tcaaaaggga | cggaagaaat | 480 |
| gcccagggcg | gggaggcgg | gacggggaac | ggcgggggcct | ttgtagccgc | agaaagtgcg | 540 |
| cagagtgggc | aggcggggtt | ctccgagagg | tcgctcctgg | atgtaggggt | acaaagggtc | 600 |
| ttcaaagtgc | taccagctca | cctggggcgc | tgacggcgca | cctgtgccct | ctttcccggt | 660 |
| agggaaggga | gaaagacaac | cgccccaata | cacacacaca | caaacacaca | cacacacaca | 720 |
| ctcacacgcg | gcgcggctct | cgccacgccc | cgtccaaagc | cggcctgaag | cttctcagac | 780 |
| cggcccaacc | cggacaaagc | cagcgctggg | gccggctcat | ccatcaccgc | gcggggcgcc | 840 |
| gtgtcctgac | gaccctggga | gtctgagaat | gctgggttat | gggtcccgtg | cctcccataa | 900 |
| ctcacgacgg | ggtcggtggg | gccacggacg | ctgcaaagat | caaagagcga | tggggccgga | 960 |
| ctcccatatg | tgggaagcag | cgctcccacc | tggcgccctg | agctcgccag | gtggcttcca | 1020 |

```
tttcgactgt tttctttctc cagcgtgtgg caaattatga ctttgaggtt ttagaacaca    1080
gttctgccgt caggctaaat gtctgtgttc ctcttctgat gccgtcccct atgacctcga    1140
gcaagtcgcc tgacctctga gctcatgatt atacctaaat ttcagtgttc taggcgtgaa    1200
tgcagtgccc tgtgtaagga gataacgttt ctaaggtctg gcccatagga aatgctcctg    1260
taaaattagc tgccattgtt accgtgatat tattagcttg gtgggcacca ggatggattg    1320
atgagaacac tgaactgttt attcactgaa aggtttgagt catccatccc ataaatacct    1380
attgaacacc tactatgtgc cggcaccgga ggtacagtag taaacaacat ggacaagaat    1440
ccctgccccc atggagctca gattctagtg aaggagacag aagataagtg aacaaataaa    1500
tataaatgat gtcaggtggt gattagtgct atgaagaaaa gtaaagcaca ttacagacaa    1560
agcatgaagg gacgaggtgt tgttttacat aaagttatta ggaaaggcct ctttgctggg    1620
gcagttcttt tggcaaagaa aaggaggtaa tgagccacgt ggttgtgggg agaagacttg    1680
caagcagaag agccactgca aaggtcctgg agcgggagtg tgcttggtgt gtttggtgga    1740
gaagagtcag tctggaacag agtgaggtga catcagacag ggagctggga taggaccatg    1800
ttgttacagg aaaggggtcc tgacccagac ctcaggagag ggttcttgga tctcgcacaa    1860
gaaataattc agggcgagtc catagagtaa aaagtttatt aagacagtag aggaataaaa    1920
agaatgacta ctccatagac agcacagcac caagggttgc tggttgccca ttttatggt    1980 tatttcctga tgatgtgcta aacaaagggt ggattattca tgcttctccc ctcccccgc    2040 cttttgtttt tcttttttgag agggagtctt gctctcaccc aggctggagt gcagtggcac    2100
aatctcagct cactgcaacc tccacctccc gggttcaagc aattctcctg cctcagcctc    2160
ccgagtagct gggattacag gtgcacacca ccatgcccgc taactttgtg ttttcagtag    2220
agatggggtt tcaccatgtt ggccaggccg tcttgaact cctgacctca ggtgatccac    2280
ctgtctcagc ctcccaaagt gctgggatta caggctcgag ctacagcacc cagcctttt    2340 tttttttttt ttttttttga cacagagtct cactttgttg cccaggcttg tatagtggca    2400
cagtctcggc tcactgcaac ttctgcctcc caggttcaag cgattcatgc ctcagcctcc    2460
cagttagctg gggttacagg cacacaccgc catgctcagc taattttttg tatttttagt    2520
agagacaggg tttcgccatg ttgcccaggc gggtctcgaa ctcctgaccc caggcaatct    2580
gcctgccttg gcctcccaaa gtgctagggt tacaggggta agccagtgtg cctgcctttt    2640
gcttcccctt tttagaccat atagggtaac gtcctgatgt tgccatggca tttgtaaact    2700
gccatggcac tggtgggagt ggagcagtga ggatgaccag aggttggtct cgtggccatc    2760
ttgcttttgg tgggttttga caggcttcct tactgcaaac tgtttatca gcaaggtctt    2820 tatgacctgt atcttgtgct gatctcctgt ctcatactgt gacttagaat gccttagcca    2880
tctgggaata tggcccagca agtcccaacc ccatttgacc cagcccctac tcaagatggg    2940
gttgctctgg ttcagacacc tctaacaatg tgagcctgca aaggccacag ggaggacttg    3000 agcttttta agggaccatg agcagagcag agacatgatc cgacttaggt ttttagcagg    3060
tttgctgatt gcttttctt ttttttttt gagatgcagt cttgctctgt tgtccaggct    3120
ggagtgcagt ggcgcgatct tggctcactg caacctctgc ctcccaagtt caagcgattc    3180
gcctgcctca gcttcctgag tagctgtgac tacaggcacc tgccaccatg cctggctaat    3240 ttttgtatt tttagtagag acagagtttc cccatgttag ccaggatggt ctcgatatcc    3300
tgacctcagg tgattcgcca gcctcggcct cccaaagttc tgggattaca ggcatgagcc    3360
accgtgcccg gccacgtgtg ctgattccta aggttgggag tagtctgcag tgggacaagg    3420
```

```
gtgaaagcaa gagaccagct aagtactgtg gcagagaaga gatgatggtc acctgggcct    3480
gggagagggg gcagtgtgca gccagcatga tttgcgtcgc caaggataga gctgtgggcc    3540
agtattcatg agccaggaga aaaaccttgg agtctctggt tcaaatgctg ctactgtggc    3600
tgtcccctgg ctgggtgatc ttccgatgtg cttggagctg gggtgacaca atatgaaaag    3660
gtggatgtta ggagaggcct ggactcctat cccatccagt ttatgatgac tttagggcct    3720
cagtttcctt gtctgtaaaa tgaggtactt gaggggccaa agcaggctcc aatattcatc    3780
aactgatgac tggataagca gatgtggtct atccatacac gggagtattt tggttctacg    3840
aaggaatgaa gtatcaatat gtgattcgac ctggatgaat cttgaaaaca ttatgctaag    3900
tggaacaagc cagacataaa agaccatatt ttgtacaatt acttttatat ggaatgttcc    3960
gtattggcaa gtccaggtca ggcgcagtgg ctcatgcctg taatcctagc actttgagag    4020
ggtgaggcag gaggacctct tgaagccagg agttggagac cagcctggca acatagtgag    4080
accccttctc tacagaaaat tttaaaaatt agtctgggcg tggtggctca tgcctgtcat    4140
cccaacactt tgggaggcca aggtaggtgg gtcacctgag gtcaggagtt cgagaccagc    4200
ctggccaata tggcaaaacc tcatgtctac taaaaattta aaaattagcc aagcgtgatg    4260
gaggtcgcct gtagtcccag ctactcggga ggctgaggca ggagaatcgc ttgaatcggg    4320
gaggcagaga tttcattgag ccgagattgc accaccgccc tccagcctgg gtggcagaga    4380
gagactccgt ctcaaaaaag aaataaatga aataaaaatt agctgggtgt gatggtgcac    4440
acctgtagcc ccagctattg gggaggctga ggtgggagga tcgcttgagc ccaggaggtt    4500
gaggcttcag tgagctgtga ttgcgtcact gcactccagc ctagatgaca gagtgagacc    4560
ctgtctccaa aaataaaat aaaaaaataa aaaattgga caatccatag aacagaaagt    4620
agattagtag ttttggaact gatgtacctg gcaacacact ttgggcatga caaccottc    4680 tcaagacatc aggagtgatg aaaatgttcc gaattagaga gtagcgatgt acaacattgt    4740
aactatacta aaaatcactg aattgtaccc agggaaaatg tgaactttat ggtttgtgaa    4800
ttatatctcc acagagaagt ttttttttt ttttttttt tttaaagtgg cagttgagct    4860
ggatcaaaag ttcttacctt gtggcccagg atggcttctg aatatatctg gacactcctg    4920
atgttgtgta aggcatttag tgtctctggg ccgggcgcag tggctcaagc ctgtaatccc    4980
aacactttgg caggtggagg cgggcacatc acttggggtc aggagttcga ggccagcctg    5040
gccaacatgg cgaaaccccg tctgtactaa aagtacaaaa aaattagcta ggcgcggtgg    5100
cttatgccag taatcccaga gctttgggag gctgaagcag gaactctgga ggccaaatgt    5160
tcaagaccag cctgggtaac acagcgagac cctgtctcta tgaaaaaaga gcagatgatc    5220
agtaaggtcc ccctgaccac tgagggtca gcaacactgg gaatcagtag aaccccacgg    5280
agggaatggc aggtgagggc tttgctctgg ctgaagtgtc ggaagccatc tcaggtcagc    5340
agtgaaccct gggatctggg acagctgtcc aggtcaggcc tcacaccaga aggcagatga    5400
gagcggagag gagctgtcag caggaagtcc ttgtctttag gcatcttgtt ccgtgatgat    5460
gcgtgtcctc cctagggcac cttgggagtt gcctgctgcc ttgggaaatg gaaatggagc    5520
tatggggatg ccgctaagga tggtttggat ggggttttga aaagtgtgac agcttgtcca    5580
gagggtttgt tctgggggct taaatagtgt atatagacct taatatcatt gtcataacag    5640
tcattaattg agcattttatg tgccaggcat tgtgcacttt atttatttgt ttattttttg    5700
agacagggtc tcactttata acccaggttg gagtgcagtg gtacaaacat ggctcactgc    5760
```

```
agcgttgatt tcctgggctc aagtgatcct cccacctcag cccctaagt agctgggaat    5820 acaggtgcac gccaccatgc tcagctaatt tttatatttt ttgtagagtt tttgccatgt    5880
tgcccaggct ggtctcgaag tcctgagctc aagtggtccg tccaccttgg cctcccaaaa    5940
agctgggatt ataggcgtga gccaccatgc ctggcattgt gcactttata tttttttataa   6000 acatgaacat ggacataaac atttgctctt tgctcaatcc tatgaaatta gaactaccat    6060
tatgccattt tacagatgag caaactgagg ttcagagaaa gaagggcctc gcagctggtt    6120
aaggggcagt gttggggaga gaagcagcag gttggacaca tgagcaggcc cagtgggtgc    6180 tgggacacc ataggaaca tgccacagcc cttgcttttg tttttgaaaa tagcttttct       6240
ctgcatagtg ccacccatag cccgggcact gaagtcgacg tgttttgctc ctcatccaga    6300
ctcagttggg attcaagtca ggcaagtggt aatgagccac tgtccaccat cacttcattc    6360
ctctgccatt cattctttca ttcactcatt tgacacacat ttgctgagaa cctgaattcg    6420
ggctgggcat ggtggctcaa gcctgtaatc tcagcatttt gcgagggtga gaggcaggag    6480
gatcacttga gcccaggagt tcgagaccag cctaggcaac atgggagac cctgcctctg      6540 caaaaatttt gaaaatcag ccaggtgtgg tggtgcacac ctgtaatcct agctactcaa     6600
gaggctgagg taggaggatc ccttgagccc aggagtttca ggctgcagtg agctatgatt    6660
gccccactgc actctagcct gggtgacaag gagagaccct gtctctggga aaaaaaaaa      6720 aagagagaga gagagagaac ctgaatttgg ccaggcacta tattgaaata atgaatgagg    6780
gctgggtccc tgccccggag cattgcaact ggatgggccc ctgagcgtca ggatatcagg    6840
agattgtcac caggctatgt gtgtctcact ctgtatgtcc cccatacca tgtgattggt      6900 gtcctgggaa ccttaggcag ggtgggagag ctgattcatt ctgccatcag cctggtgggg    6960
atgggagggg tcttggaatc atttctgggg tctggaaact tcattgcccg gttcactcac    7020
tgtgggtttg ttccataaac cccagcagtc ctcctctgcc cgagcaggtc ttcctctttg    7080
ctgggctggt gctcacagct caccttctca gtttccattt cagtgtctct tgggagtgat    7140
tttccctccg tccccatcag agatcctcag ggacctgctc tagttggcaa ataaactctt    7200 gctccccta aacacccatc cttccttccc agccgccctc ctacatattg tcattatggt     7260
gaaaaatatg caaataactt tgaacaacag tctcccagca gacggatgtt caaaaatgta    7320
ataaattaac cccataatgt aatctggatc cacaaccat ccatcatgct gatgcgatta     7380
agatatgcaa aaccagatgc tgaagagcgc atggatggag tgttggcaga gctccccgga    7440
tgggcccatg ctgactcggc ccctgcccc tgccccgcc cccatggaac ctgaggccat       7500
cagaggttta gggaacatct atctggcctg ttcatttcac taatgagact gaagcctttt    7560
aggggtttgg ggtcagatgg gtttgaatcc ctccccatct gcttcctaac ccaccttcct    7620
tctgtttgtg attggatctg aacccaaggc cccaaaccca ctttttttt gttttttga      7680 gatggagttc tcgctcttgt tgcccaggct ggagtgcaat ggtgcgatct tggctcacca    7740
caacctccgc ctcccgggtt caagtgactg tcctgcctca gcctcctgag tagctgggat    7800
tacaggcatg cgccaccaca cctggctaat tttgtatttt tagtagagat ggggtttctc    7860
catgttggtc aggttgatct caaactcctg acctcaggtg atccaccagc ctcagcctcc    7920
caaagtgctg ggattacagg cgtgagccac ccaccgtgcc cagctgacgt ttttttttaa   7980
ttgcaataat ttttggttac atgggtaagt tatttagtgg tgactgctga gattttggtg    8040
catccatcac ctcagcagtg tacactgtac ccagtatgta gtcttttgtc cctcaccttc    8100
ccacccttcc ctcaccttcc caccttcct tcccccgag tccccaaagt ccaatatatc       8160
```

```
attcctatgc ctttgcatcc tcataggtta actcccactt acaagtgaga acatatgata    8220
tttgcaaacc cagatatttt tatccacagg tttctagttg acagggtggg tactccagtg    8280
tcaagagctg ttgggacctc agtttcccca aggaaaaatg acagttgagt ttatgtcctc    8340
caaggttttt ctgacgttct tagctctgtg tgtcaggagt tctacgggtg gctcgtattg    8400
tgttttctca gggcagaggg ctggggctgg gagctcatgg agggagggcc tgacttgagc    8460
cccaatgccc ctcacactgt gtcctgaagg ccatcccaca ggagtcactt ggctctcagt    8520
ttccccaccc caggcccag tctgaagggc tcctttgcaa ggagttgccc cctatgactg      8580
ccactgcctg tcaccaatgc aaaagctgct taagcagcct ccagagaggg aaaggaaaga    8640
cccttgcttt tcccaagttc tgcaatgagt cagtctcaag gagccacgga actctgtgta    8700
taagccagtg agttgcttgg ccagctctgt gtggaaatgg catgatgtgt gcaggatccc    8760
catatcttga gaatggttgc tgtgcccaga atgtgctgcc aagtgcacca gttcctaaaa    8820
caaaatcatc catcccttg gatggatgat tttacatcac aattttacaa aatgcatcgc      8880 attttttacaa aatgaagata ttctctggga acagtccaaa cctctgtggt gattcccaca    8940 cttttgctggg catccgggcc cctggggagc ttgttaaagg gccagtgccc tgctgtgcac    9000
cccacctcga tcaggttgct ctaggcagca gggcagctgt gattaatggg ctcctggggg    9060
attctgatgc agatttccta ggactgcatt tgaagaaatg ttttgctgac attcctagct    9120
taatgggtta cttacaggtt actttttctc tccccattag aagtctggaa atgcaggttt    9180
gaaggcatca gggggcgggg ggagggatcc aggtcttcta taatgagctg taaacgataa    9240
acaagtctgg ctagatctgt gtccaaacag acggatggga ctaacaagct cttacgtccc    9300
tggaggtcac agacaaagtc ctcttggctt ctggtcctga cttgttgccc actaactccg    9360
tagctgcttc tcagatctta gttttctcac ttgtaaaata aggggctgt aaataagtgg      9420 aagccctggt gtcagaagag gcatcagagc tgggtttgta ttcccactgt gtgattttgg    9480
cgaattagag aacgtttctg ggcctgttta accatctgta aagtggggct ataaaatgga    9540
gacttagctg ctagggttaa tgagagaatt aacggaatca gtgtttgaca cataagaagt    9600
gctcgatgtt agtcattatt ttttattatt ttagtaatat catctctgag ggcccttaca    9660
ggacttccag accgagtcca cgcccctggg ggacttggga gcagtaaaat gtagtggcag    9720
gaggcacctc ggccatcgcc cacccccacca gctgggagac tcgggcaggt tattcaccct    9780
tctgcacctc gcttgactta tctgtataaa gagaacagtc acagtaactg cctcatggag    9840
ttactcccag gactgagata atccacggac acacttagcc cagtgcccag cactcggctg    9900
gagctccaaa aaggtcagct attgttatga agcgtagggc ggggagggtt catcctcttg    9960
ggcggtcagg ccaggctgca tttaggtacc cggtgggggc ggagcagggg cgacgccggt    10020
gcacgccctc ttttttttat tttaaaatt tcacccgggc cttgacaacc ggtacaatcc      10080
tgtcctcccc tgttcccgcc cccgagccag aggattcgct tttgcgtggg cagctgcagg    10140
gatggtgact cgggctagct cagatgtggc tgccgttagt cccccagctgc gcgctccccc    10200 gtccctcccc agccctcttc cggcgcctgc taaagcgaga gaaatgccct cggggggaaga   10260 tatgtagcga tccaatggaa cgtggagatc aacgttgtgt tttcttcgcg cccacccgaa    10320
gttgaaggga ggtggcgcgg cgggtctcag cccctcccgg acgccgaggc ccggccccccg   10380 cccctcggag acccgccccc gcatgcgaaa ccgccctctg cgaggccccgg tttgggccgt   10440 gcgggaatgg gcgtggcctg ggcggggcgg gcgctaggac ccaccggagc gccgtgaacg    10500
```

```
tcaccgagcg gcgccgaggc cccgggttga gcgggaggcg cgatcggtcc ggtcggtggc    10560
tccccgcggc ggggccgggc ccgatctcgg gcgggaaccg agcgcagagc cggtactggg    10620
ggagggagag ggggcggga ttcccgccgg gagggatccg gcgtagcagg gggcggagtc     10680
ttattccaac cccgcttcgc tttccgcatg tcccgctttg cgctcccggc cctgggcatc    10740
ccgctgtttc cctctgcgtc cgcggccctg ccttttcgg gggcacagct gtggtctttc     10800
caccccgcga gacagcgggg cgaggggcg cgggcggcca gtggatagag gctgatgccc     10860
ccaagcacgg acgccagcgt gggggtggag gttcttccag ctgccctgag cctgtgcgaa    10920 gcggaggtc cttccccagt tcccacagac tgtggggagg gaagagacg tggaagcgag      10980 cgggttctgg gctcctgggt ctctggaact accctctgcc cttgcccaa cactcaggta     11040 gcggaagga tgaccacgct cacacgacaa gacctcaact ttggccaagg tagggaggct     11100
ggacctgcgg gccggggc ggggcgtct gggccggcgg gcttcctcga gcgcgccacc       11160
ggcttgtgcc cccctgcagt ggtggccgat gtgctctgcg agttcctgga ggtggctgtg    11220
catctcatcc tctacgtgcg cgaggtctac cccgtgggca tcttccagaa acgcaagaag    11280
tacaacgtgc cggtccaggt gaggcacgtc ccagaaccac agagtgggta cagggtggac    11340
ttttaaaaat tctttggtcg ggcgccgtgg ctcacgcctg taatcctagc actttgggag    11400
gccgaggcgg gcggatcacc tgaggtcagg agttcgagac cagcctgaca acatggtga    11460 aaccccgtct ctactaaaaa tacaaaaatt agccgggcgt ggtggccaag gcctgtaatc    11520
ccagctactc aggaggctga ggcaggagaa tcccttgaac ccaggaggcg gaggttgcag    11580
tgagccgaaa ttgtgccact gcattccagc ctgggtgaca agagcgaaac tccgtctcaa    11640 aaaaaaaaa aaaaaaaaa aaaaacctct tccacttcgg gccaagccac ctcattccgc      11700
agggccctgc ccatgccttc caatgccttc cagttccaaa gtggtgatgc ctacccaccc    11760
ctcagaagag agttccccctt gccagaagtt agggaccagg cctgataaga gttaccccgg   11820
gggtggccgg gcatggtggc tcacacctgt aatcccagca cttgggagg ctgaggcggg     11880 cgaatcacaa ggtcaggagt tcaagaaacc agcctgacca acatgatgag atcctgtctc    11940
tactaaaaat acaaaaatta gcctggtgtg gtggtacgcg cctgtaatcc cagttactag    12000
ggaggctgag gcaggagact cgcttgaacc cgggatgcag aggttgaagt aagcccagat    12060
cgtgccactg cactccagcc tgggcgacag agcaagacta tgtctccaaa aaaaaaagtt    12120
accctggggg catggtggca cttttgaagga gctcgtgaag ctggtgaacc ttggtgtgag    12180
gagggtattt ccaaaaacct ccaaatcttc tccctaccat ttatcctaaa ctcaatgggt    12240
taaggctaaa aggcagacaa agcagtgtgc atcgcactgt agctccagtc cctagaagtg    12300
cctgtctctg gaaggcactc aggaaacatg agaataagtg gtagaagctc aaaggacatc    12360
caggtggtcc ccgcttcaag tccccacacc accattgttt tctcacttcc agtatggtat    12420
tcaagacatt acttgaggta gtcagcactt tatttttat tttatatttt attttattttt    12480 attttttgag actgagtctc gctctgtcgc cctggctgga gtgcagtggc gtgatcttgg    12540
ctcactgcaa cctccaccctc ctgggttcaa gtgattctcc tgcctcagcc tcccgagtag    12600
ctgggattac aggcgtgtgc caccacatct ggctaatttt tgtattttta gtagagacaa    12660
ggtttcgccg tgttggccag gctggtctcg atctcctgac ctctggtgat ccacctgcct    12720
tggcctccca agtgctggg attacaggcg tgagcacttt attatgaaac aggttttgtg     12780
ttagataatg ttgcccaact gtgggctaat gtgttttgag tgtgtttagg taggcctggc    12840
taagctatga tgttctgtat gttatgtgta ttaactgcat tttccgctgg cgatatttga    12900
```

```
ttggtttatc caaacataaa cccatagtaa gttgaaggtc acctttagag gggaaaggaa    12960
aaaacaattg acatttactc acttcttctt tatgatgaag tgattgaagc ccagagaagt    13020
taaggaattt gcctgaggcc acacagttcc ttagttctta acttttgaca tctgattaca    13080
ttttcctgga tccttttttct ggaaaaatgc ccaagtgcac aaagatacaa ctttagggat    13140
ttttcagact ctggaggagt ccatggaccc cacattaaga acccctaatg gtatattaaa    13200
tgctcatatt gggattgagt tcttatcttt cttttccttt gagatggagt cttgctttgt    13260
tgcccaagct ggagtgcagt ggcttgatct cagctcactg caacctccgc ctcccaggtt    13320
caagtgattc tcctgcctca gcctcccaag tagctgggat tacaggtgcc acctcacctg    13380
gctaattttt gtattttag tagagatggg gttttgccat tttggccagg ctggtctcaa    13440
actcctgacc tcaggtgatc cacccacctc atcctctcaa agtgctggga ttagaggagt    13500
gagccactgt gcccagcctg agttcttatc ttctaacttc tttctctatg gataagttca    13560
cagttcttag cctctggttt ttttttttttt ttttgagatg gagtctcgct ctgttgccca    13620
tgttgcagtg cagtggcgtg atctcggctc actgcaacct ccgcctcccg ggttcaagcg    13680
attcttttgc cttagcctgc caagtagctg ggactaaggt gcctgccacc atgcccggct    13740 aattttttgta tttttagtag atgggggtt tcaccatatt ggccaggctg gtctcgaata    13800
cctgaccttg tgatccacct gcctcggcct cccaaagtgc tgagattata ggcgtgagcc    13860
accatgcccg gccagttctt agcctcttga gggaaagtgg ggtctcctgg gtagggagcc    13920
ctggagagct gctgggcctc ggaccgaagg cagatgggc cttaggctcc tggttgtgtt    13980
gggtggtttc cccatctgtg ctttgggcct cacgagccgc atggtattgt gtgcagatgt    14040
cctgccaccc ggagctgaat cagtatatcc aggacacgct gcactgcgtc aagccactcc    14100
tggagaaggt gagggtgcac tgggctcccc agccatctca ccccatgctc accccgtcc    14160 ctgtgtgctc acagtccaac tctgggatgg ggtgaagcta ggactctgtg gggtcttcat    14220
ggctccaata cccagaagcc tgttccctgc actctggaga ccatcccaac ccaggggcag    14280
gccccaaggc atgcgggcca tgttcagggt gccttgggcc tgggagcccg ggttggagct    14340
ggctctaagt aggggctgcc ccagagggtt cggggttctt ctcacatccg tcccctgttc    14400
tccacgctaa acgttctgtc tgagctgagc ccctcagggt tcttcccca tctagtcctg    14460 atctcagact tccctgggacc ttccctatgg ggcccggca ttctctcagc ctacaccact    14520
catgctggag ggtgccggct tctcaaactc gctatctggc ctcttgggga ccccagcct    14580 agcagctgag cagggctgtg agtgggccgt ttctcctcct tccttgggca aggggtgga    14640 ggcagggtgg tgtagtcggg gtgggtgcc tggctctgca gtggggttc ctctctttgc    14700 agaatgatgt ggagaaagtg gtggtggtga ttttggataa agagcaccgc ccagtggaga    14760
aattcgtctt tgagatcacc cagcctccac tgctgtccat caggtgggct gcccctgccc    14820
ctcgcccact agctggcatc aggtgtgtct ctggcaacac acccaccct ttaaggcggc    14880 ccttgaatac cttggtaaag gcctgggagg agaaagggca agaagcacca gcatgacaag    14940
gggacagcct gtgagcagct gagatgggtc cagagagatg acatgagcta cccagggtca    15000
cctgggtggg ggcagagccc aggacacaga agcagttttc tgactcccca ggcaagtgtc    15060
cagtcaactc gaagttgacc tctggcacat gcgttagttg gtcaactgca tgcttccaat    15120
ggtgaggtca gggcactgga atctggcacc aacctgtccc cacggcctgt gtggccttag    15180
gcaagccctt tcccctcctg gcttggtgtc ctggttctgg gtcctggctg cacattaaaa    15240
```

| | |
|---|---|
| ccacctaggg aggcctcctc aggctgcccc tacctcccct gtcccctacc ccccgccgaa | 15300 |
| ttctgacttt atctggggtg gggctgggca tttcttttaa actcccttgc tggtttaatt | 15360 |
| gtgtggaccg datagggagc tgggtcctag gcatgcagca ctctcacagg cactggaggg | 15420 |
| ggtcttgtac cccaggtctg catccaggct tgatgcctgt ggtggagggg agggcgccag | 15480 |
| tgtgatggga agacctcctc tcactcccag ctcagactcg ctgttgtctc atgtggagca | 15540 |
| gctgctccgg gccttcatcc tgaagatcag cgtgtgcgat gccgtcctgg accacaaccc | 15600 |
| cccaggtgtg tccactcccc accctctctt cccttggcat ttccatggtt atctcgggtt | 15660 |
| ggtctgtgtt cccaggtcca tgtttggctg ttctgagact catctcttcc taaccctgag | 15720 |
| agtccacctc ctctgggaag cttccctgat tgattctacc tggcttccat ctccctattg | 15780 |
| actgggctt ttcttagcac ttgctttgcc atctgctctg ggggtgctgc tgagccagca | 15840 |
| agggaagtgg gaagaggctg ggcccagtgg ctggcaccag ggcggtgggg gagcctccac | 15900 |
| caacctcttg cctctccagg ctgtaccttc acagtcctgg tgcacacgag agaagccgcc | 15960 |
| actcgcaaca tggagaagat ccaggtcatc aaggtgagat gagatgggtc tgggtctggg | 16020 |
| cgcaggctct agaaacgtga tgtcgcagtt ccaggcgggc aggggcactg cctgtggcca | 16080 |
| gccacccatt acattggtgt ggcagcgcct ggcacccagc aggtcctcag gcctgtccac | 16140 |
| tgctccatct gggcacttgg ggcagtgagg agcccaggtg gagccaccta ctggggcccc | 16200 |
| cagctcatcc tggctcttct gaagtggggg ctctccaggg aggggtccta gcccaccagg | 16260 |
| ttcagcgttg gtgcctggag cctgttcgtc acttgggttc tatggacttg gcctctgtgg | 16320 |
| gggatggggg cggtcctggg gtctgcatca ccaacagctt cctagtgatt ctgaggctca | 16380 |
| ggttggaggc ccctggtctg gagtgggagg gacagcaaag tgagggcagg ccagggccca | 16440 |
| gccccgtcac cccctgacc tttgtctcct ccctaggatt tccctggat cctggcggat | 16500 |
| gagcaggatg tccacatgca tgaccccgg ctgataccac taaaaaccat gacgtcggac | 16560 |
| attttaaagg tgagcttcgt ggggacccgg gaagctttat ttaggggctg cttaacgaag | 16620 |
| tgaggcccgg tgctgaggcc ttactagagg gcttgcggga gagaacgggg gagtgcctgg | 16680 |
| tggagggctc ctcccatctc tactcttctc caccatggct atggccacga ggccccacct | 16740 |
| gtggtggagg tctgcccacc aggggcttct gtgtcctcca gcagggatgc cctggctgtc | 16800 |
| ttgctgactg tggctgtttg cttgtgtccg tcagatgcag cttacgtgg aagagcgcgc | 16860 |
| tcataaaggc agctgagggg gcacctgcca ccccactgat gcccaaactg tcagactttg | 16920 |
| ggggatcccc gcctagggca gtgctgcatg gctgccctga ttccaagtgc tcttatcgcc | 16980 |
| tctgtgtgtg gatcgcccgc cccagcccgg ggccgctcag gtctgcttgg aggatgcctc | 17040 |
| ccccaggagg gcagtgaggg atgccgcaac ctcgacttct cagcctcctg gggttccgcc | 17100 |
| ggccaacact gtctgtctca aatactgtgc tgtgagttgt ttcaataaag gggcccaag | 17160 |
| ggctgggctg a | 17171 |

<210> SEQ ID NO 17
<211> LENGTH: 11503
<212> TYPE: DNA
<213> ORGANISM: Homo sapiens
<220> FEATURE:
<221> NAME/KEY: misc_feature
<222> LOCATION: (1)..(11503)
<223> OTHER INFORMATION: RAD1

<400> SEQUENCE: 17

| | |
|---|---|
| gcttgccatc acaccacacg gggtcattta cttatcacct actccgcgct agagtactat | 60 |

```
gctaagtgcg gaggacgcaa aaattaatgt caaagataat ccttgttcac agtattctgt    120
ctagcttaag aagagttctt agttgaatga aagctaattc taacaacttg tgtgcacttc    180
ttttgaataa aaaccatcaa cttatttgaa ttcttaagtt tcctcctaaa ctccaacatt    240
tcaggaggaa gaggtcacat tctagtcatc tttgcaatct caaacccaaa ggaagcctaa    300
cttggtacag tgcatggcac attcaatgtc tgttgaatac aagtaaagct catactacct    360
agtctatttt tcagtatctc ttgagttaat gacctggtta acaagtcaga gtcacagtcc    420
caagggcaac aacttttaa aggctcccct aacgtacttc aggatccctg actgagagtg     480
gctgactatg gcagtatatg gcatactaa tcactggaga ataatagcg agaaataacc      540 aaggaaaagc actactctcc aaaaacatta aaaaaaaaa acaactgaac aactagtaag     600
aaagaacgct ggatctgagc accctgtaag tcgcttcccc gtgggccggg taaaggtttt    660
aaaacccgcc gcctccagga agacggccac gtgcacaagg attagctgca aactccgtgc    720
ccagtctggc cgggagaatt gctaaaaccg acctaccgtt aacacccggg ctactctgaa    780
attaagcaag gctgtagtca agtaagtaac ccaagaaaag gcgcacagag ccgccgccgc    840
aggtgtagcc cggggacatc ccctcctacc ttgcaaacgg ggcctgggat ccggtccctc    900
tcttcttcct ccacctcctc tgctgtggcg tgccgcttag ctggcggctc cgcatctatt    960
tcgtttcttt ttggcttctt cgcctgaact gcaaagcctc cacgccgttt cctcttggtt   1020
gccgccatct tgcctcgccg cccgcgctct tggcctcctt tccggcgctg ccgctcgctc   1080
ctatttccga tctctatggt tcggcggctc taagcgctca gctccgcggt cgtcctccag   1140
gtctgtgccg cctccttccg gtctcggtgg cgcggcacgc gcggctctct aggcctcctt   1200
cagctctgtg gtgacggtgg ccgaggtgga gggccggtct gaagagtggc gggactggct   1260
tcacttcctc cgcggttcct cggagccgcc tcgctcctct tcagggactt tgctgagaag   1320
ggctctcggg cgtccagacc ccaccgcaaa ggtagggttt ccgcactcgg gaccccgag    1380 actagtaagc gatgctgtcc cgcgggcggg ctggtgaatg gggttgtctg ggactcttgg   1440
aggattatct ggacactccg ggcccgcccc gccatcgcct gttttgttgg aggcggggct   1500
ggtggcgcgg gctgcacaaa accgactccc cgcggatttg tagctcctgt ttggccggga   1560
gataccgtgt cagttgcgtg tcttcattct tcacaacttt tcacgttatt gtcctcttac   1620
ggagacgagg aaaccgtagc ttagataatt ttcctccaga attacaaaga tagttaagtg   1680
acataggtgg ggttcggcct ggtcagccgt gttcagcctc ccagccccctt tccacctctc  1740 agcgcaggtg gagctcgccg gacctcgcca gcactgatgg gagttttact gtctaatccc   1800
ttcaggtgtt tggcgatccg ccgagaagtt gttggcccca ggagcatccc tcggggccga   1860
atgcgcagtg gacgatgccc cttctgaccc aacagatcca agacgaggat gatcagtaca   1920
gccttgtggc cagccttgac aacgttagga atctctccac tatcttgaaa gctattcatt   1980
tccgagaaca tgccacgtgt ttcgcaacta aaaatggtat caaagtaaca gtggaaaatg   2040
caaagtgtgt gcaagcaaat gcttttattc aggtatggaa gtaggcgcct ttaagcctgt   2100
gccatagata ctctaaatgt aatttaatga aatcggaagg tttcagtaga caaaataact   2160
taatagtcat aataacttgt caatagtcat aataaataac ttaataaata aataatagtc   2220
ttaagttaga gaacaaaacg tcattacttg aattttttt ctctcccggt aacaaattct    2280
tttcccatct tgttttacag agataatggt tagtaatgac taaagtttat taaactaggc   2340
tattggctag gctacagtct tcttattgtt taacttattt aatcttaaca atagtcctgt   2400
```

```
aaggtaggtt ctgttattat tcccgttttta tatatgtgga aacgaggcac aattttaagt    2460
gatttgccaa cagtcccaca gctggtaagt ggctgaattg ggataagaac gctgaatatt    2520
tgtttccaga atatatgctc tttttttccac tgcgatatgc tattactaaa gagtattttt    2580
ttcctttact ggttgtaata gaattttttgt tcttccaaag taatatttgt gtggttcaga    2640
taggattgca agttcaacta agcgtttttt aacacgtaag tgcacagcat gatctcaggg    2700
atagagaggt aaataagaca cggttcttgt cctcatgcag gggcatggta tggtggctca    2760
cacctgtatt tccagctgct caggagaccg aggctgaagc acgaagatcg cttgagctca    2820
ggcattaaag accagcctgg gtaatcatag tgagaccccc gtatcaataa aaaatcataa    2880
taaaagttga aactaatgtt gctcatgcat tatcaagtca ttcgtctatt ttccaagtga    2940
ccttagcagt agtgataggc acaaaaacga gacaagggag agtcacagag ggatagtttt    3000
agatccagga atggagataa ggatgcttca aaggatgtct ctaagatgtt ttgattgcta    3060
atcagaaatt attctcatgg gattagcaca gtattgtatt ttttaaacgt ataaagtgaa    3120
atctaggacc ttatattatt agtttttatt cttttatgta acaattttca ttttttactct    3180 tttcataggc tggaatattt caggagttta aagttcagga agagtctgtt acttttcgaa    3240
ttaatttaac tgtccttta gactgtttat ctattttttgg atcaagtcct atgccaggta    3300
aactatgatc agtataaaga cataaaagtg ttatacatag tggtcagaaa aatacaggaa    3360
gttatttgga acataaacat tggttcagaa agctaatgcc aattcatttt tcagtggcca    3420
cagtcatggg ttctaacatt tcacaatgtt aattgcaagt gtgtttataa ttcttttcat    3480
atttgtaaaa gtatttgcat ttttttttta atttacaagg ctttgaggga ttgtaaattc    3540
gaactggcca aaagaatact ttggacatgt cttaaatatt tttagcattg tgaaatgttt    3600
taattgcttc ttttttcctaa cttgtccaga attactccgc tagttagtgg cagagaaaaa    3660
caaaagccag ttctgactcc tagtttacta tgttcaaaat ttgtttcttt taagccatat    3720
tttataagtt atgtctattt tgccaaatga ttttgtggtg ttttttgagac agagtttctc    3780 tcttgttgcc caagctgcag tacaatggca cagtctcagc tcactgcaac ctctgcctcc    3840
cgggttcaag tgattcttct gcctcagcct cccgagtagc tgggattaca ggcacgtgcc    3900
accacgcccg gctaattttt tgtatttta gtagagatgg ggtttcacca tattagccag    3960
gctggtctca aactcctgac ctcaggtgat ctgcccgcct cagtctctct aagttctggg    4020
attacaggca taagccaccg caaccggttg ccgaatgatt ttcttttaaaa tatatatttt    4080 tttatttgtt aagggaattt ttaagaatgg tgaaattgaa ttgctgtggg tataaaacta    4140
aggaatcccc agaagaatga ttttatttca taggaaagca acctggagat tagctaggaa    4200
aaattcaata tagttctcca gaaaaatgta ttttacgttt ccacagacaa ttccactatt    4260
attaattata cattttctaa tacagtgttc tccagctagt ttttcacaga agcatctgtc    4320
atcttccatt cctcactgtg gctctcaatc cagtaaggag aaggagtttg aatatcctgt    4380
catattcctc cttccctcta gtggtttgca gagttaaaat ttacaccacc attaacaacc    4440
ctcttttctt ctcaatttga tttttaaatt cgaggaaata taagaatat ctcccagttg    4500 gaaaagttgg aaggatcctt gtcatagtga gtacactgac gttacagtac agatgacagc    4560
aatccactgt tacacacatt gaaccttcaa ggaatagcat accctgttct gcagcaattt    4620
agttacttgc tgtgttgatc catatagatt ctctaccctg aaattgtaca tatataaaat    4680
caacaagcta tttctgaggt gtgtatgaca acctgaaaat gattccaaag aattatgtta    4740 catttttgttc tggttcccaa ttttcttgta gttttggaat tctctacaca caactgtcat    4800
```

```
cagggaagat gtcatccctt tttatgagga gatacatata tgtgagaaat tgggcggaat    4860
aaattattct tgagaaattt tatgtatcat ttcgaggaga agctgaaccc agaactataa    4920
agctaaggcc aagtatgact tctttccatt gcagggactt taactgcact tcgaatgtgt    4980
taccaaggtt atggttaccc tttgatgctg ttcctggaag aaggaggagt ggtgacagtc    5040
tgcaaaatca atacacagga acctgaggag accctggact tgatttctg cagcaccaat     5100 gttattaata aaattattct gcagtcagag gggctccgtg aagcattttc tgaattggat    5160
atgacgagtg aagtcctaca aattaccatg tctcctgaca agccttattt caggtacttg    5220
agagcagtgc agttatagtt aatgtggtct gtactccatc ttcccactta gacatttgct    5280
taggatgcaa aattttttatt atccacattt ttagagtttt cacaacttta gacagcttgt   5340
actcttacct cataatttta tggatcaaga aacttaagac ccaggaagat taactcacta   5400
tttcatattt aggtggtggt ggcatctaga tgagaagccc agtcctctaa tttataaact   5460
ggtggtgttt tcattgtact actccttact ttcatagatc aggttacatc atgaggaaaa   5520
ttgggtttaa gtgtttggaa agggtgtttg tattatggta tcttttcaa gttagttcag    5580 gatgcagaag aagatgtttt ctacacgtgg ctcattcatt cactaagtat ctgttgatca   5640
cctaccgtgt gcttattcat cttattaagc attgtgggaa gaacagctta aaaccaaggt   5700
gaagccaaga aaatgtgaaa cagcaaacca ttaagtacca agatagcaca cacagatacc   5760
tgggaaatgc tgtataagga tttagggagg attgctcaag gctggcttcc caagggaggg   5820
cagttttcag caggagtaca atgtcaaaaa agctgttctt gatagtttaa cacaagtctc   5880
ttttcaggat tagactcaga gattctagca atttagagag aggatctaaa tattctcttt   5940
ttgaaatatt tcagaatatt aaagccccta atacatatg gaataaaagg aataaggtat    6000 tcttttttgta actactttag aagaattaca ggcccggctg taaaagtgct gtggcagaca   6060
cctgtaatcc cagcactttg ggaggccgaa gtgggcagat cacttgaggt cagggagttca  6120 agaccagcct ggccaatgtg gtgaaaccct gtctctacta aaaatagaaa aattagttgg   6180
gcgtggtggc acgtgcctat aatcccagct acttgggagg ctgaggtggg agaatcactt   6240
gaacccagga agtggaggtt gcggtgagct gagattgcgc cactgcactc cagcctgggg   6300
gacagagtga gaatctgtct caaaaaaaaa aaagaaaag aaaaagaatc acaggccctt    6360
gtcatgactt tggggagtta aaaatttggc tcaaggtctg agaaagttaa ccaaaatgga   6420
aattggaaac cttactttag cagtggaatg aagtaaaaaa ttcaggtact taaaacagta   6480
tttcagggga tctcctcagt gatctctctc agcctgggta acgagatgga ccatggtatc   6540
tttcatctcc aggatgggaa acaatttggt ggtagggagg taggagttga aattttttcc   6600
tggatatgtt aaattttaag tacctgcgac actaggagt ggctggatat gtagttatgg    6660
tgctcaggag atccatttag actggaaatt tagattgggg aaccatcatc atggctgggt   6720
atggatgaga cgggtcagag agagagatta tattagaaga aagaaaagat ggaccccagg   6780
aaaaccacac ctggaagatg ggaggcagaa atggagctta gggaaaaacca acctggatct   6840 tatcgccatg ctcatataat acttagcaac gtgctaatcc tgcagcaaat gttccaggag   6900
ttcttgcaaa ttaaatcagc atgttaacac ttataaattg tctacaaata acttctggta   6960
ttaccaagtg aggaaaacca tgcaatagcc ttaagagcag tctaagatac agaaaagctg   7020
taattcctag gtgtaggatt gggaacagac ctaaggggttg cagtagactt agatcaaggt   7080
cttccatgag tcctcaattc tctcgcctgt tatatatttc tgacttaagg atgaggaaaa   7140
```

```
gtcattttca gagtaggatt agggtaatga aattaaagtg tccectaccc tttteetttt    7200
acaattgatt ttcttcaaac ccattgatta gttgtcctga actccagtgg gagctttatt   7260
atggtacttg ttatcgtgtg ttataagcat tgtgtacat gtctgtttca cccactagta    7320
tgaatttctt aaggaagtgt tttcttatt tggatcctaa tgtggttat ttttggatga     7380
atgaataaat gaggtaatca ttttctatag gttatctact tttggaaatg caggaagttc   7440
ccaccttgac tatcccaaag attctgattt gatggaagca tttcattgta atcagaccca   7500
agtcaacagg tcagttctta atatagaggt tgtcattggt gataaagagg aggttaaata   7560
ccagatttct gttaaataaa aacactttca atctgttaat taaaatgcac agcattttat   7620
aaaaatgaat agtagagtgc tggacttact aggggatgta gggttctaac agtgaatgaa   7680
ttttaaaaca gaaatatta gcaaattgga taagtacttg attttattct tagatttgct    7740
acttttttatc ctttacttgg gagttctgag cagtgttcac tgtgttgata aacagcgtt   7800
ttattttttc ttctacagat acaagatttc cttactgaaa ccctctacaa aggcattagt   7860
cctatcttgt aaggtatcta ttcggacaga taacagaggc ttcctttcat tacagtatat   7920
gattagaaat gaagatggac aaatatgttt tgtggaatat tactgctgcc ctgatgaaga   7980
agttcctgaa tctgagtctt gagtatgaca attcactgat atttatgtgt acatttatga   8040
tagatgaagt tcttattctg agtacagtac tctttgtcat ttcatattgg attttctata   8100
gagaagaagc acaatgggga agataggagc aaggtcatgt accctaatag ttactatgtt   8160
ttgtaaatcc attttgtaga gggcatgtaa ataaatgttt tcctgtagtc atagattatt   8220
caggactgtc ctttagttct gtcttttgaa ctcatgggaa taattgtgag tcagcgtaac   8280
atttcaagag tctaaaggtg gccgggtgtg gtggctttaa tcccagcact ttgggaagcc   8340
gaggtgggcg gatcacctga ggtcaggagt tcgagaccag cctgaccaac gtggagaaac   8400
cccatctcta ctaaaaatac aaaaaattag ccggacgtgg tggcacatgc ctgtaatgcc   8460
agctactcgg gaggctgagg caggagaatt gcttgaaccc gggaggcgga ggttgtggtg   8520
agctgagatg acgccattgc actccagcct aggcaataag agcaaaactc tgcctcaaaa   8580
aaaaaaaaaa aaaagtcta aaggcttaaa gtttgatgca gctacctgaa atgatctttt   8640
atttatttat tattagaaaa agcaaaggca tatgggcatt gcttattagt ttgaattcta   8700
gagactagat cttaaagtag tggttctcaa agtgttgtgc ccgcaccaac atcagaatgg   8760
cctgcaaact tgtagcaaac tctggggagg aggccagcat tctgtatttt aacaagcttc   8820
cctcaggaga ttctgatgcc tgctaaattt tgggaaccac tgttttaaag gaaacttttt   8880
ttttctttaa tagcatttaa ttgtatgaga tgattgcttt tacatgtgat ttccttgcaa   8940
atgttctgaa gttgaggcat caccaaacaa gtctgaacaa ttctttatgt gatttatttt   9000
taaagtagac cttttgaaga gatctatgaa tgggatataa agcaattttc agtgttacag   9060
gttttcttct tcttctcaaa actgtttgct gtaagtaact gcaatcagta cttactactt   9120
tccatttgct tatgagtttc ttgacaaatc aaggtgtaga aaaccagtta ttaagtgatt   9180
ttgtactttc ctggtagttg tcactaaaat aatttttgtg gcatataaat atatttaata   9240
aaatgcaaaa attatcttcc tgtctagtag aaaaaattac atgagtaaag tgaagcttct   9300
gtctttgtta ctgtaccagg tgacaacagc tgagtgtccc tccatggaca gtcactattg   9360
gcctttttgag tgagacagtt ctttaggata aaaacctgtc atcccattgc aggattcatt   9420
tagcctttct ggcccttacc cactgatgct agtcattgtg accaccccac ctcccccaaa   9480
taaaagtgtg ccaaactatt cattgttgag aaccattcaa ttgtattcac caaaattgga   9540
```

```
ggatatattg gaatgcccta ccttaatata ggtcacatag cattagagaa aattggtttg    9600
gagagtatta cagcaaagtg tgctgcaagg aggctactcc agcacaatgg caggcactgc    9660
ttcccaggca tatggacaat tctgggaggt ggccagggtc agcacctgat aactagtaag    9720
tgtctcaatc tcagcataca aaatttagca gtgactacaa aagaagttgg aattttctaa    9780
aatgtttgta ttcaagaagg aaacaaatga atttactaaa tgttgtcaga gtattttttg    9840
tttagataac caccaagaac agaacaaacc taaaagatac ttgggaaaat atctaatcag    9900
tcaacattct aaggactgtt aaatgtgaaa tagcatagtt attttttgtc ttttgttact    9960
agtgtgaaca agaacggcg cctaacatat aatgggcatt tagtaactct gttagatgaa    10020
agactctcca atttcagatt ttcttttagc atcttattag tcactactta attctgatga    10080
tttagctcta aatttatttt gatctcagtt tttttatttt tattttttgga gacaagatct    10140 tgctctgttg cccaggctgg agtacagttg taggattaca gttcactcca gcctcaatct    10200
cctaggctca agcaatcctc ccatctcagc ttcccaaata gctacgacta caggtgcatg    10260
cctccatgcc ctgctaattt ttgtattttt tgtagagatg gggtttact atgttccta     10320 ggctaatctt gaactcctga gctcaagcaa tccacccgcc tcggcctccc aaagggctgg    10380
gattacaggc gtgagctatc atgcctggcc taatgtattt tttaaaagtt gaatctaaaa    10440
agaatttaaa acaaatataa atcagctcag taaggatgga tattttttgta catttaaaac    10500 tattatttta ggccgggagt ggtggctcac acctgtaatc ccagcatttt gggaagccga    10560
ggcaggggga tcatctgagg tcaggaagtt cgagatcagc ctggccaaca tggtgaaacc    10620
cctacctcta ctaaaaatac aaaaattagc tgggtgtggt ggtgggtgtc tgtaatccca    10680
gctacttgag aggctgaggc aagagaatca cttgaaactg gaaggcgggg gttgcagtga    10740
gccgagattg caccattgca ctccagcctg ggtgacagag caagactccg tctcaaaaac    10800
aaaaaaaatt aaaataaaaa ttattgtttt agctgcatgt cttcagctat ttagaattca    10860
aagactaatg aattgtttct aagtcaccct aacatcaagg tacttatttt ataaagaatt    10920
tcctccttat ttgtgttcta attgacccag gaattttac tttaataaaa gtttaacttt    10980
atttcctatg gaaaatcact aggggagtg ctccctcagg cagagcaggc gacactttgg    11040
tgccactaca aattgatgtg tagtatatag aagaatacag tcttatattt aaagactttt    11100
agttctgtct ttttgaagtt tatctctctt tctagtaaaa tggtgcttac tgtgaatgga    11160
taatcttttt tttcatttt catttgttga tttcccattc gatgatgtag tgcttccacc    11220
gagaattgat gaaatgcttc aaaataataa aagtatttgt taaattccac tttaataaaa    11280
ataaggcatg taacacagtc attttaacag gaagccacag ggtttctgtg gtgttaccaa    11340
agtcctagta aaaattaatt aaaattgcta aagggcaga atgtggcact ctcaacagtg    11400
gggtaggcag tccttcagaa catagagact tccttctttc cttccctgtc ttcacattgc    11460 ttgtcccta tccccacctg aaataaaatc tattgggtcc tga                     11503
```

<210> SEQ ID NO 18
<211> LENGTH: 33027
<212> TYPE: DNA
<213> ORGANISM: Homo sapiens
<220> FEATURE:
<221> NAME/KEY: misc_feature
<222> LOCATION: (1)..(33027)
<223> OTHER INFORMATION: TIMELESS

<400> SEQUENCE: 18

```
ggtccagctg agcctggtgg cggaaaggct gcggccccgc gccagagggc cggtggctcc      60
tccgggcttc tgaggacccg cagggagcgg gtgagtgagt gtgtggcgag agggcgctaa     120
gcggacacgg ggatcctttc gaagctatgg gggcattctc gggaaacgct gagtcccttt     180
tcccgccacc cggtttagag ccaggggcg gggctcgtgc tgcaggcgcg cacgcgcaat      240
tctgtactct gctccttagt ctcccgcgcc gcgttccgg gtctcaccgg acgcgggctt      300
agccctacgc tgctccgcac agcttgggtc tcccgcggga tggggttgtg atggaaaggg     360
gcttggaatt cctgaattag aacagaaagt gcctgaggga gttccacttc ggagcttagc     420
atctagttga gacctcctga aaaaaaccgg tgtgtggcct ggcggtcagc agtggtcgga     480
attcacaggc cgctttactt atatcgtggg ttttatggaa cggatttctc actccctccc     540
ttcgttgcct tgttcgggtt tgtcacctgg acctcagccg ctaatgaagc ttttttcctt     600
gagcctctca attctttgcc attcgtgctt cgactagtac tttcaattt ttatttattt      660
tattttattt tgagacggag tctcgttctg tcgcccagga tggagtgcag tggcgccatc     720
tcggctcact gcaacctccg cctcccgggt tcaagcgatt ctcttgcctc agcttcctga     780
gtagctggga ttacaggcgc gcgccaccat gcccggctaa ttttgtatt ttttttagta      840
gagatggggg tttcacctta ttggtcagga tgatctcaaa ctcctgactt cgtgatccgc     900
ccgcctcggc ctcccaaagt gctgggatta taggcgtgag ccaccgcgcc tggcctgttt     960
gtttttttg gttgttttgt tttgttttgt ttttgagatg gagtctggct ctgtcgccca    1020
ggctggagtg cagtggtccg atctcggctc actgcaacct ccgcctcccc agttcaagcg    1080
attctcctgc ctcagcctcc caggagctg ggattacagc tgcccgccac cacgcccggc     1140
taatttttgt attttagta gagatggggt ttcaccatgt tggccaggcc ggtctcgaac     1200
tcctgacctc aaatgatccg cccgcgtcgg cctcccacag tgctgggatt acgggtgtga    1260
gccaccacac ccggccctac tagtactttg tacaaagtaa aggtagatca tctgatgtta    1320
aatttaaaac tcctctttga ccacccacag ttagccttaa atccgtaggt gggtgtctgt    1380
ggcctctcag tctggccctg accctctcaa tctcattttg taaatctctt acgcacctga    1440
ctcctggcca cgtggaaaga ttgtggctgc cctctttcat atctcagtac ttagttcctg    1500
ctgttccttc tgcttggaag atcttgacac tgctctgcca agcgaacttc tctttgaaga    1560
ctgagcttaa ttgtccctct gaaaatcaat gtatccagct tcctatgcca agttagtcac    1620
ttcttcctgt gtgtccctga agtttttac ccccctctat taccaggggc actgatacag     1680
ctcaataaaa gatcaataaa aggttactga gctcctaaca tgtaccatgc actgtgctta    1740
gcgccaggct tacagagatg agtaggatgg agagttcccg acccttaagg aactcaagtc    1800
ctaaggaaaa cacatgtaat tgagtcttct gtggttacag tgaaagggtc atcaagaagt    1860
ccttcctggc ttccttcctc ctctcactgc actcacacca tcttacatcc tgatgcctcc    1920
aaatctttag ctccaaactc ttctccctca tcttccagac ttctctgttt cagttcaatt    1980
tagtaaagca tttattgagc acttacattg tgctgcgtaa tgatgattcc tgatgtgaaa    2040
gagtttacgt tttcgtgcag ttaacatagg atagttagaa tcacctgagg aacattgtca    2100
aaacacttgc ctaagcccca tcgctggaaa ttctgatcct gtagcaaggc tctgaaagtt    2160
caagggtgaa taagaattcc tatctctact aaaaaaaaaa aaaaaaaaa aaaaaaacaa    2220
aaattagctg ggtatggtgg catttttcctg taatcccagc tacttgggag gctgaggcag    2280
gagaatcact tgaacccggg aggcggaggt tgcagtgagc cgagattgca ccattgcatt    2340
ccagcctgag tgacagagtg agactcgtct ccaaaaaaaa aaaaaataaa aagaattcct    2400
```

```
gtcctcaggg aatctaaggc taatggaggg agatagactt tgattttaac tattatatac   2460
aacatgaatt gtaagtacca tgttggaagt ctgaatatgg tacacagtag acattaagga   2520
aaaggaggtc acttctgtat ggagaagtca ggaggaagtc cctttttgggc agtctttttt   2580 tttttttttg agatggagtt ttgctcttat tgtccaggct ggagtgcagt ggcgtggtct   2640
cccaggttca agcgattctc ctggctcagc ctcccaagta gctggaatta caggcaccca   2700
ccaccacacc tggctaattt ttttatttt tagtagagac agggtttcac catgttggcc   2760
aggctggtct tgaagtcctg acctcaggcg atccatccgc ctcagccacc caaagtgctg   2820
ggattacagg catgagccac tgcgcctggc ctgcacagag tcttcagagc taagctgata   2880
tttggatggg aggccattct agatagagta gtggcttgag agagaagcgt gagaggtaaa   2940
caggagagag attcatgaaa gactttgtat tgtaggcact ggaggtcact gaaactttag   3000
ttttgtatag taatgcatgc taatagtaaa gaattcaaat agtaccaaag ggaaagacaa   3060
atatttctcc tatcctagat cccctagttc tcagagacga tcactatgaa gtttcttatg   3120
tatccattga agtgttctaa gcaggattgt tatatgccta aatcaggtaa ccatattgag   3180
gctagattga acaagactgg aggcagctgc attcatgcct gtaatcccag cactttggga   3240
gcccaggtgg gtgggtcgct tgagcccagg agttaaagac cagcccgggc aacatgacaa   3300
aaccttgtct ctagaaaaaa tacaaaaatt agcagggtgt ggtgatgtac cctatagtcc   3360
cagctatttg ggaggctgag gtgggaaagt cacttgagcc tgggaggttg aggctgccgg   3420
gagctgtgat tgcaccactg cactccagtc tgggtgacaa agtgagaccc tctttcaaaa   3480
aagaaaaaaa gtctggaggc agagaaagag gataggaaga ggttgagtaa cctaagcaag   3540
agctactcag gaactgaact aaggcagtag caattgggat agaaggatag acagcaactg   3600
atagaagaac ttaaggaagt taagtgagat ggagctaagg tgactcctag gtttcttttt   3660
tttttttttg agacagagtt tcgctcttgt tgcccaggct ggagtgcagt ggtgcgatct   3720
cagctcactg caacctccgc tcaagcgat tctcctgcct cagcctcctg agtagctggg   3780
attacaggca tgcaccacta cacccagcta atttttgtatt tttagtagag acagggtttc   3840
tccatgttgg tcaggctagt cttgaactcc cgacctcagg tgatccaccc gcctcggcct   3900
cccaaagtgc tgggattaca ggcatgagcc accacatcca gcctcttttt tttttttttt   3960
tttttttttt tttttttgac gtggagtttc gctcttgttt cccaggctgg agtgcaatgg   4020
tgcgatctcg gctcaccgca acctccacct cctgggttca acaattctg cctcagcctc   4080 ccaagtagct gggattacag gcatgcacca ccacacccag ctaattttgt atttttagta   4140
gagatggggt ttctccatgt tggtcaggct ggtctcaaac tcccaacctc aggtgatcca   4200
cccacctcag cctcccaaag tgctgggatt acaggcatga gccactgcgc ctggccctag   4260 gtttcttta ataaggtgaa actcttagcc ttcttcactg aggagatagt gtcagtcctt   4320
gagagagcca aagtggagac agacttggga agatgagttc agctttagac ctattgagtg   4380
taaggtatct ttgagacata aaggtagaga atgctattca gttagtcagt ttaacatacg   4440
agattgtcaa ctcaatagct cagaggggcc agaaatacag atttgctggc ttctggcttg   4500
ggtggtagtt gaagtgcatg ggagagggtg agtttgccca atcaggccgc gtacagtgag   4560 aaggaagaa ggctaaagat gcaggcctaa ggaaaatcag cacttaagta ggaggaggaa   4620
cagccaataa gagatcaaag gggaaagttt tatttttatgt tggattttc ccccttaag   4680 atgagctagg acaggtgtgg gggcacatgc ctgtaatccc agcactttgg gaggctgcgg   4740
```

```
tcggaggata gcttgagcct gggggcttga ggctgcagtg agccgagatc gcaccactgc   4800
acatcactac acttttgaga tactgcctca aagaaaaaa acagatggaa tagccttgag    4860
caactcataa tatatgggga tgggctagt ataaagggaa ggttggaaat aaggaataac    4920
caactaaggg acaggaagtg attaatgagg atcacagagt acttagatta gaagcaaaga   4980
actaagggtg ggtgtttgaa atatgtatgt ttttaggctt gggtggagag agttgagaga   5040
gttcatgtct gataacctca attgttccta acaggaagga agcagataaa ccaggtggga   5100
ggcaaggaag cagtagagtg aaggggcttg aggataatga tgaaagttag gaatagtggt   5160
tctttgggaa gagacaatga aggggaccaa gaatacagaa atgaggctgg gcacggtggc   5220
tcatgcctgt aatcccagca ttttgggagg ccgaggcagg tggatcacga ggtcaggtgt   5280
tccagaccag cctggccaac atggtgaaac catgtctcta ctaaaaatac aaaaattagc   5340
caagcgtggt ggcgggcacc tgtaatccca gctacttggg aagctgaggc aagataatcg   5400
cttgaaccca ggaggcggag atgcagtgag ccgaaatcac gccactgcac tccagcctgt   5460
atgacagagc aagactctgt ctcaaaaaaa aaaaaaaaa agaataccga aatgatttgc    5520
tggaccaggc tgaaggccct gctcaggttg caggctatac atgttatcgg gggaaccagc   5580
ccccaatatt tcaatgtagg ttcttttcta ttttccctaa gtgtcagctg gtctcataaa   5640
taaagagaaa gactacaaag agaagaattt tacagctggg cctctgtggg tgccatcacg   5700
tattggtagg accatgatgg cgacttgagc cgcaaaacca gcaagttttt attagggatt   5760
ttagaagggg aggggggtac gaatagggag tggatcacag agatcacatg cttcaaaggg   5820
caataaaaga tcacaaggca aagggcaga gcaggatcac aaggcaaggg caaaattaga    5880
attactgatg agggtccatg tcccactggg cacacattgt cttgataaac atcttaacag   5940
gaaacagggt ttgagagcag aaaaccagtc tgactagaat tcaccaggct ggaatttccc   6000
aatcctagta agcctgaggg cactgcagga gaccagggca tatttcatcc cttatctcaa   6060
ccgcataaga cagataatcc cagagcagtc gtctataggc ctaccctgg gaatgcattc    6120 cttccccagg gttatcaatt attaatattc cttgctggga aaagaattca gtgatatttc   6180
tcctactcac atgtcgttta taggctccct gcaagaagaa aactatggct ctattctgcc   6240 tgaccccca ggcagtcaga ccttatggta tctttccttg ttccctgaaa atcgctgttg    6300
ttctgttctt tctcagggtg ccctgatttc atattgttca aacacacgtt ttacaaacaa   6360
tttgtacagt taatgcagtg atcacagggt cctgagatga catacattgt cagtttatga   6420
agatgacggg attaagagat taaagacagg cataggaaat tataagagta ttgattgggg   6480
aagtgataaa tgtccatgaa atcttcataa tttatgttca cagattgcag taaagacagg   6540
cgtaataaat tatgaaagta ttaatttggg gaactaataa atgtccatga atcttcaca    6600 atttatgttc ttctgctgtg gcttcagccg gtctctccat tcggggtccc tgacttcccg   6660
caacatcatc tatcttatat cactatagag ggtcgtttgg ttttctccag cacatctggg   6720 cctagattg aattgaagtc taggaagcag atggttgcat tgatctgagg ttatgtatgg    6780
tcttttgcag ggtgagtgca ctgaaaggaa aagagataga ggccacacgg gaaaatggcc   6840
aaactgatgt atatagtgat acagtagtag gatatgtgtg accctggttt gatcattttg   6900
ttttctagct cagaaatctt cagtggctcc ctggcttagg ttctaaatct ttgaactgat   6960
ggacaaagat gaggttttc ccataaagct ggttccagct gcttttccat tgctttcctg    7020
ttggactcat ctattcataa tggctccctc tttggttttg cactggcagt tctctgctta   7080
aatgcccatc ctattcccag ctgccttaat cctatgcagc tttcaaggc ccagttctaa     7140
```

```
tcatgcttcc tcagacaaaa cctccttgac cactttaacc tgaaaagagt actagttttt    7200
tagttttttt cagtatcacg tatttagagc ttgtactgcc ttatctttta cattgtttgt    7260
tctatatttg tggattttat ttctgcaact acatttcttt tttttttttt tttttttgaga    7320 cggagtctca ctctgtcgcc caggctggag tgcagtggca cgatctcaac tcactgtaac    7380
ctccacctcc ctggttcaag tgattctcct gcctcagcct cccgaggagc tgggattaca    7440
ggcacccgcc accacacctg actaattttt tgttagtttt agtagagacg gggtttcatc    7500
atgttggcca gactagtcat gaactcctga ctttgtgatc cacccgcctt ggcttcccaa    7560
agtgctggga ttacaggcgt gagccaccgc gcctggcctc tgcatctaca tttcttaaat    7620
ttctttagcg ctaccattgc acctgcacgc tatcttttgc caggaaggtt ctccctaagc    7680
atttagtaac tgactataga gtctgacaga tggagaggaa attaatattt ggggcggggg    7740
aggggttctg tttgttttgt ttatttgtct tttgagacag ggtctcactc tgttacccag    7800
gctggagtgc agtggcacaa tttcagctcg ttgcaacttc aacctcctgg gctcaagtga    7860
tcctcctgcc ttagcctcct gggtagctgg gactaaaggt gtacatcagc atgcccggct    7920 gattttgtg ttttattttt tgtggagact gggcttcgct atgttcccca ggctggtctc    7980
aaactcctgg actcaagtga tcctcccacc tcaacctccc aaagtattag tattacaggc    8040
gtgagccacc atgtccagcc agggattctt actttgtgct cagcactggg tagagtgctt    8100
aatatcactg cttctcaaac tgtcttggta aaggaccagg tagattttc cctcaagctg    8160 ttgcagatca gtagtgttct aaaagcactt ctgtaaaata aaattactag aaaaataaca    8220
tttaaaaaga catagagaat acaggctttt tattattatc atcattagat tcaacaaaca    8280
ttggctgggt gcagtggctc atgcccgtaa tcccagcact tgggaggcc gaggtgggtg    8340 gatcacttga ggccaggagt tcagcagcct aggcaacatg gcgaaacccc atctcaacta    8400
caaaacacaa aaaaattagc ctggcatggt ggcacaggcc tgtaatccca gctacttggg    8460
aggctgaggc acgataatag tttgaacccg ggaggcagag gttacagtga gccaagatca    8520
cgccactgca ttccagcctg ggtgacagag ggagaccctg tctcaaaaca aaactgtaaa    8580
ctgcctgtca aattgcccta agatgttcta agtgctaatg ctttcttcct gtacttacct    8640
tgatgcagac tgctaatagt ttgtggattg gcagtggtct gaagaccaag gtttgagtag    8700 cattgctta catgatctca tttacacttc cctaatatct tgtgagggtg ggtattatta    8760
ttatttcctc agtatactga taaggaaaga gatttagtta agccacctgc tcaagttcac    8820
cagtttagta ccagacagaa ttggaattca agtgctagat gccattttgt tcatactact    8880
gggtctcaaa gaggatcctt ggagcagagt tggtttgggg caggtagagt gttttgtttc    8940
gtcttcaaaa agtaagttta tttggtcggg cgcagtggct catgcctggt atcccagcac    9000
tttgggaggc ccaggtgggc agatcatgag gtcaggagtt tgagaccagc ctggccaata    9060
tggtgaaacc ccatctctac taaaaataca aaaattagct gggcatggtg gcgcgtgcct    9120
gtagtcccag ctacttggga agctgaggca gaagagttgc ttgaatccag gaggtggcgg    9180
ttgcagtgag ctgagatcgt gccactgcac tccagcctgg gcgacagagc aagactctgt    9240
ctcaaaaaaa aaaaaaaaa aaaaaaggtt aatttgaatt gcaaatacat ttaatatttt    9300
atctgttgtt ttcttttggt tcttgcattt taatgcctcc aagtattgat ttcagatgca    9360
tattgcttca tctgaactgc ttgatactta gttgagtagg aaaagtaact aacatccctt    9420
ttaaatgtcc agttccattg gctctgtggt gtttgacaaa gttctcacct ggtctatgat    9480
```

```
gaaatgtgaa aataaagtca atgtaatgaa ttttttcatg aagtcatatt tattaaattt    9540
gaaggacagt attttatcct gagattttg tctgtagttt ttttggtgtt aaaatggtag     9600
aaacagaatg cgtatagtaa ttgtgtggag tgttgtttat aacggctgtt tgagatataa    9660
ttcatatact gtaaaattca ccctttaaa gtgtacaatt caggctaggt gtggtggttc     9720
acacctgtaa tctcagcact tgggaggcc aaggcaggag gattgcttga ggccagtcag     9780
gagtttgaga ccagtgtggg caacataggg aggtaccagc tctacacaaa tttaaaaatt    9840
agccagatgt ggtattgaat gcctgtggtc ccagctgctt gggaggctga ggtgggagga    9900
ttgcttgggc caaggagttg aggctatagc gagtcatgat tgatctgtac tccaacctgg    9960
gctggtcaac agagtgagac cctgtctcaa aagaaaaaaa aaaaaaaga aaacccctgt    10020
acaattctgt gatttttagt atattcagag agttgtacaa ccatttctgc ccacctcagc   10080
ctcctaaagt gctgggatta caggcgtgag ccactgtgcc catatcagcc tattgcattt   10140
gcctattctg gacatttcat ataaattcca tcatacaata tatgaccttt tgtgtttggc   10200
ttctttttt tttttttt ttttttttt ttgagaagga gttttcactc ttggtgccca      10260
agctggagtg cagtggcacg atttgggctc actgctacct ccacctccag ggctcaagcg   10320
attctcctgc ctcagcctcc cgagtagctg ggattacagg cgcccgccac catgcccagc   10380
taattttttt gtattttag tagagacagg gtttcaccat gttggccagg ctggtctcaa    10440
ctcctgacct cagggtgatc tgcccacctt ggcctccaaa agtgctggga ttacaggtgt   10500
gagccactgc acccggctgt gtttggcttc tttcactgaa catgttttca agtttcatct   10560
acttcatggc atgtatcagt cagtattcca ttccttttt ttttttttt ttttttttt    10620
ttgagacaga gctttgctct gtcatctagg ctggagtgcg gtggcgcaat atcagcccat   10680
tgcagcctcc acctcccagg ctcaagtaat tctcccacct cagcttctct agtagctagg   10740
accacaagca cacaccacca cactcggata atttcatttt ttaaattttt tgtagagacg   10800
aggtctcact atattgccca aactggtctt aaactcctgg gctcaagtga tcctcccgcc   10860
ttggcctccc aaagtactgg gatttcaggc gtgagccact gaacctggct gtgccctttt   10920
taaatataga ctttcaaatt tgagttagca taattaggag gcaggaggat cacttgaagt   10980
caggagttcc agagcagcct gggcaacatg gtgaaaccct gtctctacca gaaataccaa   11040
aaaattagct gggcaagcca ggcacggtgg ctcacgcctg taatccctgc actttgtgag   11100
gccaagacgg gcagatcacc agaggtcggg agtttgtgac cagcctgacc aacatggaga   11160
aacctcgttt ctactaaaaa tacaaaatta gctgggtgtt gtggtgcatg cctgtaatcc   11220
cagctacttg ggacgctgag gcaggagaat cgcttgaacc cgggagggag gcagaggttg   11280
cagtgagcca agatcgtgcc actgcacccc aggctgggtg acagagcgaa actccatctc   11340
agaaaaaaaa aaaatgttt atcaagccca gtattaacac tctcggagcg agagagcaga   11400
ctgacctctg caaatgaga tcagcattag tttggtgtag tttgggtctt tttatgtgtt    11460
ttttggctg cctaatctct agtcagtgtc tgccttttg attgatgggt gtgttgctta    11520
gtgcttgcct gctgcctcca tcccataatt ttaagtacat gcatgatatg cagtccatgt   11580
gcatgagcgt tgatgagttg attatcatac ggggtcatca taaggacact ttttctcttt   11640
gatgcatatg acttgccctg aagagctgcc ccttgctggt ttggtcttga tcctgcgggc   11700
catggggtcc ttgcttgctt ctcttagctt acttttgtt ttggcctgct taacttctgc    11760
cttttatctt gcttcttgct cacctacccc ttcaccttgc ttctgctctc atgttcttac   11820
tcattctgcc ctttatccaa ctttaaattc cctttactat tatcctgcct catttctgt    11880
```

```
attctgcttc ctcagttaca gtgagccgtg attgtaccac tgcactcctg ggtgccagcc   11940
tgggtgcctg agtgagaccc tgtctcaaaa aaaaaaaagc tataaaatca ttttgcaaac   12000
ttgagtgtac taggaaaagg tattactatt tttggttttg tacaaatgat ttcctttctt   12060
ttatgaatta ttttcttcag ttatattttc tgaaatcagt ttactgtttc aaagggtatg   12120
acccaggata atctgttgat tcaaaattcg gcaaatattt attgcatgct tggctgggcg   12180
cagtggctca agcatgtaat cccagcactt tgggaggccg aggtgtgtgg atcacctgag   12240
gtcaggagtt caagacacat ctggccaata tggtaaaacc ccgtctctac taaaaataca   12300
aagttagcct ggtatggtgg cgtgcgcctg taattcaagc tacttgggag gctgaggcaa   12360
agaatcactt aaacctggga ggcacaggtt gcagtgagcc gagatcacgc cactacactc   12420
cagcctgggc aacagagcgt gagactctgt ctcaaaaaaa aaaaaaaat tgcatgctcg   12480
ctatatgcca agctctattc taggcactgg agaatgcagc aatgagcaaa acaaaatgaa   12540
gccctacagc atggagcttt cctttttgttg gactggttta tgattttac tatataaatc   12600
aatgatttct aaatgctaga agaacactaa tatatgatga catttccatc cgtctgaagt   12660
gaaatgagaa aaataaggat aatgtattct tactgaattc tgaccactgt tcggtgttct   12720
aaattccttt ctgaggagcc tggagagagc catgtctgca gcccatccat cttgctaaac   12780
aggtcacttg gacccagtat gttatggctt gctctcataa cttgactctg gcatagcatc   12840
aatcacacga tggttagcag acttccttaa ctaacttacg ctaatattaa acattccttt   12900
ctactgactc caacttttta ttttttattta tttctattta tttttgaga tggagtcttg   12960
ctctgtggcc caggctggag tgtggtggcg tgatctcggc tactgcaac ctctgcctcc   13020
cgggttaaag cgattctcct gcctcagcct cccaagtagc tgggactaca ggtacacacc   13080
accacaccca gctaattttt gtattttag tagagacagt gtttcaccat gttggtcagg   13140
ctggtcttga actcctgacc taaggtgatc cacacacctc ggcctcccaa agtgctgaga   13200
taacaggcat gagttactac gcccagccaa gacttcttaa attagtgttt tcttggactg   13260
cagttactca ttggctaaga ataagtctct ttaaatattt gtcagagttt ggttttttcca   13320
tagacagtat ggagttttc atagtgatta tggattttaa aggacatagc tgagattata   13380
tcatatactg tattctttt cggagtgtta acaagctgt ttctttttt tttttttttt   13440
taagacggag tctcgctctg tcgcccaggc tggagtgcag tggtacaatc tctgctcact   13500
gcaagctcca cctctcgggt tcactccatt ctcctgcctc agcctcctga gtagctggga   13560
ttacaggcgc ccgccatcgc gcctggctaa ttttttgtat ttttggtaga gaggggttt   13620
caccgtgtta gccaggatgg tgtcaatctc ctgacctcat gatccgcccg cctcagcctc   13680
ccaaagtgct gggattacag gcatgagcca ccgtgcccgg ccaacgccca gctaatgttt   13740
gtattttag tagaagatgg ggtttcacca tgttggcaaa gttggtctcg aactcctgac   13800
cttaggtgat ctgcctgcct tggccttcca aagtgctggg atgccaccgc acctggccta   13860
caaaatttt ttaaaaggcc aggcatgatg gcacatgccc agagtcatag ctactcagga   13920
ggctgaggca ggaggactgc ttgagcccag gaatttgagg ttacaatgag ctgtgatcat   13980
gccactgtac tccagcctgg gcaacagagt gaaaccctgt ttctcttttt ttttttttt   14040
taaaagaaga tgattctttg ggagatagtg ataggaatg taccagtttc tattcactcc   14100
atttcctcac ctgttctgtt agatgctgat ttctactgaa attaccaagg tttaagagta   14160
actttggaga ggagagtgaa ggacctttct ctacacattc gcagtgtctc agaagcctca   14220
```

```
gggctcctga gatgtattag atccttggtg gaatcactgt atggccagag ctcggttttt   14280
ttaattcctg tggtacatca gagctgtgtc tgcctggaag agccacagaa agtggagggt   14340
gacagggttg agcaatttat tttttccaga gactctgtag accaggctgg agtgtagtgg   14400
tgcaatcaca gctcactgca acctcaaaca cctaggcgca agtagtcctc tcatctcagc   14460
cggcctcccg agtaggtagg agtgcaggtg tgtgccacaa cggttggctt tttgtacaga   14520
tggggtctca caatgttgcc caggctaatc ttgaacactg gggcaaatga tcatcatgtc   14580
ttggcctcct aaaatgctga gattataggc atgagccact gtgcccagcc agggtctaac   14640
aattttattt atttatttat tttgagacag agtctcgctc tgttgcccag gccagagtgt   14700
ggcggcatga tcttggctca ccacaacctc tgcctcctgg gttcaagcca ctctcctgcc   14760
tcagccttcc gagtagctgg gattataggc atgcgccacc acgcccggct aattttgtat   14820
ttttagtagg gacagggttt ctccatgttg gtcaggctgg tctcgaactc ccaacctcag   14880
gtgatctgcc tgccttggcc tcccaaagtg ctgggattac agacgtgagc caccgcgcct   14940
ggccagggta ggtgcttaat tcataggctg gagcctcttt ggttttgatc aggtagaagc   15000
cattatttaa aacttctct ggggctgaga gcagaacttt tggttgtgac aaaagtcaaa   15060
catttgagga tcttgttcag aatattctga gcattagggc ctcgtcctgt tcctatcttc   15120
ttttcatgga gaggaactta catttttttat ctttctctat ttctccaggc ctcatcattt   15180
ctgtctcctg tttctccact tccttctctg ttggttggtc cactgatgta tggacttgca   15240
catgatgaac tgtgaacttc tagccacatg tagtgccctt gggtacttgg agggagacac   15300
ttaccataag gaaccagatt gcttaggtga gtaccttttt gatgaaacag gaaaaaaatt   15360
ggcttgaatt aaggaggtct gttgaattcc tcaaaccatg ggtgtgaaaa gatgtgggtc   15420
tggatggagc ttcttccaag gttccacatg catgttttgt tctgtctctg aagagagcgt   15480
gaaggatctg atccgctatt tgaggcatga ggatgagaca cgagatgtgc ggcagcagct   15540
gggggcagcc cagatcctac agagcgacct tctgcccatc ctcacccagc accaccagga   15600
caagcctctc tttgatgctg ttatcaggtt gcctccctag cttttaaact tttgccacct   15660
gccaggcttt ggtgtttgag ctgataggtt tggcgtttga gctggtaaag aaacttaaca   15720
acttctccct ccttcattgt ctcccagact gatggtgaac ttgacacaac cagccttgct   15780
ctgttttggc aatctgccta aggagcccag ctttcggcac catttttttgc aggtgctaac   15840
ttatttgcag gcctacaaag aggtgaggat ttcctttgga gtccctgggg tggaatatgg   15900
ggcagtggtg aagaagtgga tgactgctac ttaagatcag gttccctatt tcacaggcct   15960
ttgccagtga gaaggctttt ggagtcctca gtgaaacctt gtatgagctg ctgcagctgg   16020
tgagtgagtc ttcaccttac aggataccat gggacagcat tttgcacctt ctccgggcag   16080
aggaggagat gctgagatat ggtcccagtc cttggggatg tggtagtccg atccatagtc   16140
tctggctgcc tcagtactgt ttgaactctt tcttttttaat cctgcttctc ttctatgcct   16200
gggtcttcca gccagagtac atactgcctg ccttccacag ggagtctctt cctcttactc   16260
tcttctggtt agggctggga ggaacggcag gaggaagaca acttgctgat tgaacggatc   16320
ctactgctgg tcagaaatat tctccatgtc ccagctgacc ttgatcagga gaaggtgagg   16380
gtcttgggtg ttctgtgttc ttgtgcatgg ttaggttgag ctgcctttttt ttttttttt   16440
tttttttgaga cggagtctct ctctgtcgcc aggctggagt gcagtggtgc gatctcagct   16500
cactgcaagc tctgtctcct gggttcacgc cattctcctg cctcagcctc tgcctcctga   16560
gtagctggga ctacaggtgc ccgccaccat gcctggctaa ttttttttttt tgtattttta   16620
```

```
gtagagacag ggtttcacca tgttagctaa gatggcctcg atctcctgac cttgtgatcc   16680
acccactttg gcctcccaaa gtgctgggat tacaggcgtg agccaccgcg cccggccaag   16740
ctgccctttt tgggctattc tgtcctctga caagtctggg agaggaggct tggtcaaaga   16800
atgagttgga gagcttcaag gcagggcagt gggattgaat gagcttcctt tctaccctca   16860
ccactcactg ctcagaagat tgatgatgac gccagtgccc atgaccagct cctctgggcg   16920
attcacctca gcggcctgga tgacctgctc ctctttctgg ccagctcgtc tgctgaggag   16980
caatggagcc tacatgtgct agagattgtc tcccttatgt ttcgtgacca ggtgagaccc   17040
tggcctattg cccgagtccc ctccgcccat gtacttttct gctgtacagc cagaattgct   17100
cttgtgataa tggctgcatt atctggggaa ggcaggcgac agcaggagta gccatgtctt   17160
gagttcagta gtaccccctt attcatggtt ttctttcctt gatttcagtt actcacagtc   17220
aaccatggtc tgaaaatatt aagtggaaaa tttcagaaat aaacatttta gaagttttaa   17280
acttgtacat tgttctgagt agtgtgatga aatcttttgt ccctgtttgt cctaaacaag   17340
atgtgaatca tccctctgcc cagcatatcc acagtgtata cccgcctgtt agtcatgtac   17400
tagccatctt agttatcaaa ttgaaaaaac ataatagaat atgtgtatgt gcgtatatat   17460
atatgtatac atgttctgtt ttctgataac tatatatata gcacatatat acattctata   17520
aaacatagaa cgtacatgtt ctatgtatat gtgtatacac atacaaatat atatatgtat   17580
atatgaatat atacatatat atatttcagt actgtctgca gtttcaggca tccagtgggt   17640
gtcttagaac atttcccct cagataaggg agaacgacag cacaatgccc cattaatggg   17700
gttctatttt gttcactctt tgcatcccca gtaggcgtga actcaggata aggaatgact   17760
gtcctcctga ttcttccctc tttgttccaa tctagaaccc cgagcagctg gcgggagtag   17820
ggcagggacg cttagctcag gagcggagtg cagattttgc agaactggag gtgttgcgcc   17880
agcgagagat ggcagaaaag aagactcgag ccctccagcg aggcaacagg tgagtgacag   17940
agaggcaggt tctttttcct acatcatgga atgctgaggg catagaaggc aaattctaag   18000 gtgggtgat tgaacaacat tttagtgttt tttttttttt ttttgagac agaatttgc    18060 tcttgtcgcc caggctggag tgcactggca cgatctctgc tcactgcaac ctctgtctcc   18120
tgggttcaag cgattctcct gcctcagcct ccccagtagc tgggactaca ggcgcatgcc   18180
accatgccag ctaatttttt gtatttttag tagagacagg gtttcaccat gttggccagg   18240
ctggtctcaa actcccgacc tcaggtgatc cgcctgcctc agcctcccaa agtgctggga   18300
ttataggcgt gagccaccgt gcccgaccaa catttgtag ttttaacttg ctccaatgtg    18360
ccgatgatag agaatggaga taaagtttcc agagaactga aaaatcacct tggacctttt   18420
tgtttctgca ggcattctcg atttgggggc tcctatattg tccaggggtt gaaatccatt   18480
ggggagaggg acctcatctt tcacaaaggc cttcacaacg tgagtattct tacatctgga   18540
gtgggaacat agtggagttg catagcttaa gcagggtaat catcttaaga gttcttggct   18600
gtgcctggtg gctcacactt gtggtcccag cactttggga ggctgaggca ggaggattgc   18660
ttgagcccag aagttcaaga tcagactggg caacatggca agaccctgtc tctaaaaaaa   18720
aaattaaatt aaaggttggg tacaatggct catgcctgta atcttaacac tttgagaagc   18780
taaggaagga gaattgcttg agcccaggag ttcgagacca gcctgggcaa catggcaaaa   18840
ccctgtccct acaacaagtg aaaaatacta actgagcatg gtggcacccg cctgtggtcc   18900
tgactactcg ggaggctgag gtgggaggat tccttgagcc caggagttca aggctccagt   18960
```

```
gtgctatgat tgcatcatta cactccagcc tgggtgacag agcaagttct tgtctcaaaa   19020
gaaaaacaaa aattagtttc ttctgagaaa attgacgaga gctgcaaggg gaaagtggta   19080
tttaggagta attctaatcc cccaaccgac acacccagct acgaaactac agttcagatt   19140
tgggaaagca gccgaaaaag gtgcctaaac gtcgccaggc cgcccgagag ctgtccattc   19200
agcgccgttc tgccctcaat gtgaggctct tcctcagaga cttctgctct gagttcctgg   19260
agaactgtta caaccggctc atgggatcag taaaggtgag aacctgtgaa ggatatggag   19320
ataatcagga atggaataga caggtgatga tgcagctgtt ggtgggtaag aagtggggag   19380
gagctcgggg aggctgcccc tggaatgtgg actcgtaggt gggaaggata tacagttagg   19440
atgtccctga gagatagtga aaatgccagg aacgagtggg ctcctggcat gacaaaagag   19500
gctctggaaa aattgcctca gagggagagg aaagggagaa caggagagag ttggaaattg   19560
tggatcctag agtattatag cggtgtcccg gcgtggtggc tcacacctgt aatcccagcg   19620
ctttgagagg ctgaggcagt ggatcacttg aggtcaggag ttcaagacca acctggccaa   19680
tatggtgaaa ccgtatctct actaaaaaaa aaaatacaaa aaaaaaaaa aattagccgg   19740 catggtggtg tgcatttgta gtcccagtta ctcaggagcc tgaggcagga taatcacttg   19800
aacctgggag gcagaggttg cagtgagccg agatcagacc agtgcactcc agcctcatca   19860
tgacagtgca agactgtcaa aaaaaaaaaa aaaaaaaaaa aagaccaggc gcagtggctc   19920
acgcctgtaa taccagcact tgggagtcc aaggcaggtg gatcacctga ggtcaggagt   19980
ttgagaccag cctgcaacat ggtgaaaccc catctctact gaaaatacaa aaaattaact   20040
gggcgtggtg gcgggcacct ataatcccag ctacccagga ggctgaggca ggagaatcgc   20100
ttgaacccag gaggtggaag ttgcggtgag ccgagatcat gccattgcac tccagcctgg   20160
gcaatagagt gagactccgc ctcaaaaaaa aaaaaattat gacggtgtcc agcatccatt   20220
ccatcatcat aggacaggaa ggaagaagtt ggaagccctg gagtcatggt gatcttttt   20280 tttctttttt aaatgtcagg atcacctgct tcggagaaa gctcagcagc atgatgagac   20340
ctattatatg tgggccttgg cttttcttcat ggccttcaac cgagctgcct ccttccggcc   20400
aggcctggtt tctgagaccc tcagtgtccg taccttccac ttcattgagc agaacctcac   20460
caactactat gagatgatgc tgactgaccg caaggaagct gcctcctggg cacgccggtg   20520
agtgggatgg ttactggaga tacagtgagc tagggatctg aatgcttgaa ttctggctgg   20580 tgctttttc ctgattcagg gttcaggtga tcagtctggg gagcaaggac tggctgggaa   20640
atttagtttg ggtggcacat tttttttttt cgctgtggga agttgctgtt tccatgggcc   20700
attgccctaa gctgtcctcc atttcaccgt ttcccgtcaa ctctcaggat gcacttggct   20760
ctgaaggcct atcaggagct gctggcaaca gtgaatgaga tggacatatc tccagatgag   20820
gctgtgaggg agagcagccg catcatcaag agtgaggccc tggcctggtc cccgatccca   20880
gcctgtccca tctcgtgatg agaatctcat tcttcccagt cccagcttca tccatctctc   20940
cttttcaagc tttccagaat agcccttcca tcccttttctc ttccccattc ctagacaata   21000
ttttctatgt gatggagtac cgagaactat tcctggcact ttttcgaaag tttgatgaga   21060
gatgccagcc ccgctctttc cttcgtgacc tggtggagac cacccacctc ttcctcaaaa   21120
tgttggagcg attctgtcgg agccgtggga acctggtggt gcaggtactg gcagccccca   21180
caatgtagaa agagctgtaa gggagagtca aggaaggggg gctctttctt ctcacagttt   21240
gtacagctta agttcatctg ttaaacgtgc tctgaactac gacagcaaga ggtttgtggg   21300
tgttggccag tgtgagtcta ctacagtttc cttctcccat tagaataatc tctgatctgc   21360
```

```
cataaatatt ttagttcagt caggaaacat ttattgaaca cctaccacat gccaagtaca   21420
aaaaccctgg ggattcataa ttttagagtc taataattat gctatagcat tttctggtta   21480
taccttgaaa gcattgtggt gaggtggaaa gagccttaaa ttgcggccag gcatggtggc   21540
gcacacctgt aatccccgcg cttgaggagg ccaaggtggg cagattactt gaggtcaggg   21600
gttcaagacc agcctggcca acatggtgaa accccgtctc tactaaaaat acaaaaatta   21660
gccaggcgtg ttgatgcaca cctgtaatcc cagctactca gaaggctgag acagaatcgc   21720
ttgaatccag gaggtggaga ttgcagtgag ccaagatcat gtcactgcac tccagactgg   21780
gtgacacagt gagactctgt ctcaacagca acacaaagag agccttaaat tgaactttag   21840
aaagtctgga atctagtcct gtattggtta ttattggaat aagctcaagc tggtcgtgtc   21900
ggtctccaga tccataaagt tgggattgtg acagttgtcc atgaacccaa agtgaaatca   21960
gtgaaaagcc taggacaggc tgggcacagt ggctcatgcc tgtaatccca gcactttggg   22020
aggccacagt gggtggatca tttgaggcca ggagtttgag accagcctgg gcaacatgac   22080
aaaactcctt ctctactaaa aatacaaaaa ttagctgggt gtgatggcac gcacctgtag   22140
tcccagctat ttgggaagct gaggcacgag aattgcttga acccatgagg cagaggttgc   22200
agtaggccaa gatcatgcca ctgcactcca gtctgggcca cagagcaaga ctctgtctca   22260
acaaaaaaca aaaacaattc accagcatgg tggcacatac ctgtagtccc agctgctcag   22320
gaggctgaag cacgaggatc actggaactt aggagtttga ggatgcagtg agctgtgatt   22380
gagacattgc actccagtct gggtgagacc aagaccctat ctctgaaaaa taaaattatt   22440
ggttcacatt aaaataaaaa aaaccctggg acaaaatgca aactccaagg aatttgtatc   22500
ctggaaacac agagactttg ctttgtataa acagattttg gccaggcgc ggtggctcat   22560 gcctgtaatc ccagcacttt gggaggctga ggcgggcaga tcacttgagg tcaggagttc   22620
acgaccagcc tggccaacat ggtgaaaccc tgtctctact aaaaatacaa aaattagcca   22680
ggcatggtca tgcgcacctg taatcccagc ttcttgggag gctgaagtgg gagaatcact   22740
tgaacccggg aggcggaggt tgcagtgagc caagatcatg ccattgcact ccagcctggg   22800
caacagagca agactccgtc tcaaaaaaca aacaaacaaa caaaaattag cctggcgtgg   22860
tggcacacac ctgtaatccc aggtacttgg gaggctgagg caggagaatc gcttgaaccc   22920
aggtggcaga ggttgcagtg agccgagatc acgccattgc actccagcct gggcaacaag   22980
agtgaaattc tgtcttaaaa aaaaaaaaa aaagattttt gtaccagaac cttcctataa   23040
ctctagttgc tacagcttaa aattctgtca taactggact tgaaagatgc agtagtacca   23100
acgagacttt gctaaagggt attttttgcac tcagagctct gtggtattat ctgtaatact   23160
aggtactatc atttattgag catttactgt gtgtcagaca ctgtgctgac gttttcatgt   23220
aatcctcaca gtagcgcatg tgcccaaagt ggttaagcaa cttgtccaaa gtcttgttag   23280
taatactaat tcaatactca aatccagatc tgctggactc catgctccta agttttggtg   23340
tgtttgattg taagttcttt aatggagcat gaccttcagg ggcctctcag ttcatcctgt   23400
ttgacttttc agtacccaca ccaaagactg gttcacagcc ctgacttggg agaagcagga   23460
tttgggtatt gactcactct cctgcttttc tttttttaa ttatttattt atttattat    23520 ttttttaagc agggtctcgc tctgttacct aagctggagt gcagtggctg aatctcagct   23580
cactgcaacc tctccttccc gtgcccaagc gattcttctg cctcggcctc ccaagtagct   23640
gggactacag gtacacacca ccatgcctgg ctaattttg tatttttgt agacacaggg    23700
```

```
tctcgctgtg ttgcccaggc tggtcttgaa ctcctgacct caagcgatcc acctgcctag    23760
gcttcccaaa gtgttgggac tacaggtgtg agccactgcg cctggctgtc ctactttca    23820 ggagaaaaaa ttagaggctt tatttacata gtgctttgca ttttatgaag cttttccatg    23880
tgtcttattt gatcctcata gcatctgctt attctgtaga cctcttgaga tagcactgct    23940
tttggcaaac ctctgaactc aggaaatggg tcaggagttt tgccatgaca tcttatgctc    24000
actcacatta tagcttttat ccacactcta gtgtaattac ctttctactt cctgtctcca    24060
ccactagagt aaaagctcct caaagggaag gaaatatgct gttcactatt gctttctatt    24120
accgatggat agcagataat gggcactctg tgaatgtcca gttaattagt tttgtaatag    24180
aaaagacact gatggggaaa gccctcttta gctctcttga catcctaata caattctttc    24240
cccacagaac aaacaaaaga agagaaggaa gaagaagaag aaggtcctag accaggccat    24300
tgtttctggt aatgtcccat ctagcccaga agaagtggag gctgtgtggc cagccctggc    24360
tgagcagcta cagtgctgtg cccaggtagg tggttacaga aaccctgtct tttttgagaa    24420
tagtgctcag ggtatacaat ctgggttttc cactccctcc gctcccatag ctttatccat    24480
ctctagaatt ctgagctcag catggactcc gtggttccct ttgatgcggc ctcagaggtg    24540
ccagtggagg agcagcgggc agaagctatg gtacggatcc aagactgtct cctggctggc    24600
caggccccac aggccctgac tctcctgagg tctgctcggt aagaaccctg cctgctcatc    24660
ctcttgggct ttgggggaag gaggaggcca tcactgcgt acagtgttct cagtcttcaa    24720
aagagagttg tctcatcaag gctctgggac tgtataccaa ctgactcctg gggcgttttg    24780
attggtttgt tgggttttt tgtttctgaa aaacattaaa aaagcatagt taattgagaa    24840
aaaaataaag aaagcaaatc ctcacttgac atcatcaata gtccttggt  aattgcagct    24900 ttgagtaaaa tgacctacgg catgtttctt ataacgttaa gagaaaaaaa actggttttg    24960
ttatacattg tttcacttaa agtggcagta tccaagaacc tattgaagac attaagggcg    25020
gacttaactt taattctagt agccaaagat atgcatcatt aacatttga  tgagtaacca    25080 tccagaggtt ttttgctcc  gttacatgta aaaatatcgt atataccttg ttttacaaaa    25140
atgaaatact gtacatgctg atttatagta attttcact  tctcagtata ttatgagcat    25200
gatttctcat cagatatatt tctgtaattg ttaatggctt taaaacacca ttgtgtgaat    25260
atgtacattt gttcaaccag gtgtcaaaca tttagattgt ttgcattttg ttcttagctg    25320
gtttttattg aattgtggct tatgaggaaa attttccctg gagtctttgt ttcatttgag    25380
gtaacagttt gcattctgtt tctggccaac aaaagaaata agtctaaatt ccttcttcta    25440
cttcgaatta taaatttaaa gccagatttc ccctgggtaa agccttttt  ctatctgtgc    25500 tccagggagg tgtggcctga aggagatgtg tttggctctc aagacatttc tccagaggaa    25560
gagatccagt tgctgaaaca aatcctctct gctccacttc cccgtgagtc tccacccttc    25620
acatctgtct ccttccagct cttttctagc accaacataa cagagactca gtaatcctcc    25680
ctctgtctat agggcagcag ggcccagagg aacgtggggc agaggaagaa gaagaggagg    25740
aggaggagga agaggaggag ttgcaagtgg tccaggtgtc ggagaaagaa tttaattttc    25800
tggactacct gaaacggtgc gggctgagag gcctgagttg gtcctagagt ggcgattgtg    25860
cggctgtgag gatgagctat gtcttcctta tgctgacatc ctctccctcc ttgttttggt    25920
gcagctttgc atgttcaact gtcgttcgag cctatgtgct gctactaagg agctaccagc    25980
agaatagtgc ccacactaac cattgcattg tgaagatgct gcaccggctg gcccatgacc    26040
tcaaaatgga agccctactt tttcagctgt cagtcttctg cctcttcaat cgtctgctta    26100
```

```
gtgaccctgc tgctggagcc tacaaagtga ggggataaca aggaatgggg ttctggaagg   26160
gtatgggaac cctcaggtaa ataaataatc ttcaggagat agaaggtgct gagaggtgtc   26220
aagggctggg agatgggaaa acaatgagaa agtagacagg caggttgagg gagctgcatg   26280
gagaaggaca gaagagagtg agtgaggagg gggcagctgg gaacagctat agagaaaata   26340
cctagagggc caggttcggg tctgcattgg accagagagg cctcatagta acctccttct   26400
cctacaggag ctagtgactt tgccaaata catcctgggc aaattttttg cactggctgc    26460
agtcaaccaa aaagcctttg tggagctgtt gttctggaag aacacagctg tggttcgaga   26520
gatgactgag ggctatggct ccctggatga caggtgagct tgaagttggc aaagggtggg   26580
tgggggtagg ggaagtttga tgcagagtca cagaatgtca aagctgttaa gagcttgcat   26640
gtcatttagc ccactgtttc tttccctatt atgggtgaga aacaggctc aggaggtgaa    26700 atgctttacc taaagttatc caagagagga gcagggactg gagcctaagt ctagtgtgta   26760
tctagtttcc ttctccatca ccagcctcca tagaggtagt cactgttggg agctgggtgg   26820
ttgcccagag ggagtctgtg tgcgacctct cccaaaatgt gctgggaaac catgaggatt   26880
tgtagaaatg tttgtcctct ttcccttagt atctcagccc ctctcctttc acttagtc     26940 tcttttccc ataatattct cagtccctag agtcagaatg gtcagggttc cattggccca    27000
acctggaaaa tctcttagtt tgacttttag gttcttacgt ggaaggaaag tgaggggaag   27060
gaggcacact gtaggcctct gctggctggc ctctttcagt tacctgcctt gtccttcctg   27120
ttcttttcag aactgatcag agaaggcctt tggtctcctc tttttgggcc aagaacctat   27180
atgctccctt tctcctttca ccattcaggt cttccagtcg cagagcacct acatggagcc   27240
ccgaagaaga ggctcatctt cgggagctgt acctcgccaa taaggacgtg aaggtgaga   27300 ggccttggga tctggagagt ttatgaggag ggcagcttga gctgtgggac cttctttact   27360
gccttagtcc ttccccacgc cagggcagga tgtggtggaa gccatcttgg cccacctgaa   27420
tactgttcct cgaacacgca agcagatcat ccaccatctg gtacagatgg gactggctga   27480
cagtgtcaag gacttccaaa ggtagagagg cacatgctct ggaggctatt gggatgggga   27540
ctcgtgatca cttcctgggc ttcctcttcc actgacacct tcctaatcag gaaaggaacc   27600
catattgtac tgtggacggg ggatcaggag ttggagctgc agcggctttt tgaggaattc   27660
cgggactcag atggtgagta agctggaaac tcagggacc tttgagatga aagccaagct    27720
atccatttat tttggggctg cctttttattc ccaaggaaag attctcccat cccttctgtt   27780
cacttactat atttgtaagt gtcatttttg gatgaattga ggtaccctct ttccagagac   27840
ctctgattta ttttactcat ctctttccct gttacccttg ggtattcaca tgcttgcttt   27900
ttatagatgt cctgggtcat atcatgaaga atatcacagc caaacgctca cgggcccgaa   27960
tagtggataa actcttggct ctggggctgg tggctgagcg gcgggagctg tacaagaaac   28020
ggcagaaaaa gttggcatcc tccatcttgg taacaatctg accctagctc tgctggcatg   28080
ggctcacttc ccttgaagtg gtccttagga gcagtccacc tggattcttc ctgcctgagg   28140
ctgttctgac caggtccttc cgagagagca ggcgcggggg ggtgcggtgg tcaggaacga   28200
ggagactcca ctaagttcct tgtgttgcct tcattttcat tcccccaacc cccaatgaat   28260
tttagccaaa tggagcggag tccctgaaag attttttgcca ggaagatctg gaagaagagg   28320
aaaacctgcc tgaggaagac agcgaagagg aagaagaagg gggctcagaa gcagaacaag   28380
tccagggtag cttagtcctt tcaaatgaaa accttggtca aagcctgcat caggaaggtg   28440
```

| | | | | | |
|---|---|---|---|---|---|
| aggactttgg | ctgggagaga | tgtctcaggt | ggagggcttg | ggagtagggt | caaatgtaag 28500 |
| tttccctcat | ttccttaggc | tttttctatcc | cgctcctatg | gctccagaac | tgcctgatcc 28560 |
| gagcagctga | tgatcgggaa | gaggatggtg | agtggacagg | tgacactttt | aggagaagag 28620 |
| ccctggaggc | tattggagac | ctacctggtc | atgggatgga | gaaccagttc | ttcccttata 28680 |
| tcttcaccat | atgactattg | accctgtctt | aggctgctcc | caggccgttc | cattggtgcc 28740 |
| actcacagag | gaaaatgagg | aagccatgga | aaacgaacag | tttcagcagc | tgttgcgcaa 28800 |
| gctaggggtt | cggccccctg | cctctgggca | ggtaaatatg | tcagttacag | tgtcaaccaa 28860 |
| ggcgtgttag | tcctatttcc | aaatacatct | cctcctcctc | ctcactgtca | tggtggtcct 28920 |
| ccttatcctt | atcgtcatct | tggtccttct | cattgtcttg | tcatctctga | ccaagattcc 28980 |
| tgcagcagcc | attctgctag | tcttcttttc | ctctctctaa | tctcccttc | ccctagatcc 29040 |
| atcttccaga | ctgcctccag | atttatcttt | ttaaaatata | gtcttgatta | cagttgtccc 29100 |
| ttagtgtctg | agaggggatt | ggttccagga | ccccctgcc | cacagatacc | aaaatctata 29160 |
| gatgctgaag | tccctttttg | tagtatttgt | aaataaccta | ggtacaacct | gtatacttcg 29220 |
| tcatttctag | attacatata | atacctatac | aatgtaaatg | ttaggtaaat | aattgttata 29280 |
| ctgtattgta | aatatatata | tatacatttt | atttatatat | atatatatac | acacacacac 29340 |
| acacacacac | atatatatat | atatatatat | tttttttttt | tttttttttt | tttgagacag 29400 |
| agtctcactc | catcacccag | gctggagtgc | agtggctcag | tctcagctca | ctgtcgcctc 29460 |
| aacctcccag | actcaggtga | tcctcccacc | tcagcctcct | gagtagctgg | gactacaggc 29520 |
| ctatattacc | actcccagct | aattttttgt | attttttgta | gagatggggt | tatgccatgt 29580 |
| tgcccaggct | gtgtattatt | gtttaatgtt | gtattgttat | tttttttaa | tattgtcgat 29640 |
| ctacagtggt | ttgaatccac | agactcagaa | cttgtggata | tggagggtca | agtcctctgt 29700 |
| ccagagccat | tgatggttcc | ttactgcttg | caggacagaa | tccacaaact | ccaaatggca 29760 |
| tccccatcct | tggccaacct | ttgcagcctc | acagccacac | cactcacaca | ccgactttac 29820 |
| atcatagtca | ccctggtagg | cttttcatg | cctccaaatg | gttaatcatg | ccagtccctc 29880 |
| tattggaagg | ctgcaaccgt | gcacacaggg | tgacacacac | acacacacac | acacacacac 29940 |
| tccatctgtc | ttactgatgg | acctctaccc | agtcttcaag | agtctgctca | attgtcacct 30000 |
| tgtcagagaa | gcagtccttg | tcattctttc | aaccctgaa | gtaaaaataa | tcacttttgc 30060 |
| agctgtgatt | tgttcatgcc | cctgatgcag | ccttaatcct | gtggaatctg | ctgggtatgg 30120 |
| tggctcacgc | ctgtaacccc | agcactttgg | gaggctgagg | caggcggatc | acctgaggtc 30180 |
| aggagttcaa | gaccagcctg | gccaacatgg | caaaaccctg | tctctactaa | aaatacaaaa 30240 |
| attagcccgg | tgtggtggta | ggcacctgta | gtcccaccta | cttgggaggc | tgaggcagga 30300 |
| gaattgcttg | aacccaggag | ggtgagcctt | tattgctttg | ccacggcact | ctagcctggg 30360 |
| caacagagtg | agactctgcc | tcaaaaagaa | aaaaaaaaa | atcctgtgat | actacagtac 30420 |
| atttgttctt | tttcccattg | gattgtgagt | tatttgatag | caaggatcat | acctgattca 30480 |
| cctttacatc | cccaggattt | atttatttat | ttatttattc | aattgacaac | tatagccagg 30540 |
| tgtagtggct | catgcctgta | atcccagcac | tttgggaggc | tgaggtggga | ggatcgtttg 30600 |
| agactggcct | gggcaacaca | gcaagaccct | gtctctacaa | aaaattttaa | gtagttgggc 30660 |
| atcatggtgg | catgcacccc | tgtggtcctg | gctacttgag | aggctgaggc | aggaggatag 30720 |
| cttgatccca | agagatcgag | actacagtgg | accatgattg | tgccactgca | cttcagcctg 30780 |
| agtgacagag | gcagacccct | tctcatttaa | aaaaaaaaaa | aaaaaagaa | caaccaaaaa 30840 |

```
aacctataac tgggaacctc ctaatgtagc aggcactgtg ctaggcactg ggtatatatt    30900
agatagtaag tattataata aatagagttc acaaccettg tggatcttca ccaatattgg    30960
gtcatatata ttcaatgaat atcatactct gggaaacaaa aagctggtcc tttcccttt     31020 caactttttg gccctgtag gaaaccttct ggcgaattcc agccaagctg agtcctaccc     31080
agctccggag ggcagcagct tctttgagtc aaccagagga ggaacagaag ctgcagccag    31140
agctgcagcc taaagtccct ggagagcaag gctctgatga ggagcactgt aaagagcacc    31200
gagcacaagc cctgagggcc ctcttgctag cccacaagaa gaaagcgggc ctggcatccc    31260
cagagggtaa tagtgcgaca gccatcttct gagtattaac gtgtcagcca tgttggtcta    31320
gagggcagga aaggtgttct gagaatatga ggaccgagtt cctaattttg tgtcatttat    31380
ggtcattgca gaggaagacg ctgttggtaa agagccgctg aaggcagcac caagaaacg     31440 acaattgctg gacagcgacg aggaacagga agaagatgag ggcaggaaca gaggtaggga    31500
atttgatggg accttctttt tcttctctaa tcctgaagac aaactctacc acgtccttac    31560 ccettaacat attagatat tctctctctc tctcaccccc atcgttccca cagcaccaga    31620
gttgggagct ccaggaatcc aaaagaagaa acgataccag attgaggatg atgaggatga    31680
ctgaagagct aagaagccta ggggtagaga tagacacgtt tttagatggt gcattcaagt    31740
cagagttgga agggtcatac aggacccaga agctcctctt actggacaga gcagtagaat    31800
cccaggctct ttcacggatt taggctgaga aacttcagca gcagtattgg acttctctgc    31860
tgtcagtctt tgtttctccc agttttate ggtatgcccc agcagctctc tggagattta    31920
gttctcttct tctaggaacc atttctttg gttattggag ctccttagca aataagagga    31980
gtgagtgaaa tagagaaagc accccggacc cctttattg gtctgttcct ttggcttct     32040 cttggaggtg ggtcgcagca ccagatgggg agctttatga catgacaggc gggagttttg    32100
taccactttt agaagatacc agatgcctct gtcctcattt tgtttcctat gatcatcctc    32160
tagataccag atagaggccc attcctgcat ttgagatagg gttggaatat agtactctag    32220
atgatgaatg tgtttgcttt gtgtttggta ttaaacatgt aagattagaa gttctcatct    32280
cagtctgact tggcgatatg tctaagttcc ccagcccttc ccctgctgtg ctcttgaaag    32340
aagaacttaa caattttagg gtaaaaagag accaacagac cggcacagtg gctcaaacct    32400
gttgtcctag cactttggga ggctgaggcg ggcggatcac ctgaggtcag gagtttgaga    32460
ccggcctgga caatatggcg aaatcccatc tccactaaaa atacaaaaat tagccgggca    32520
tggtggcatg cgcctgtaat cccagccact cgggtggctg aggcaggaga attgcctgaa    32580
cccaggaggc agaggttgca gtgagctaag gtcacgccag tgcatatgcc tgggcgacag    32640
agcaagactc tgtctcaaaa aaaaagaaaa aaaaaaaaga ccaacaacct tccctttct     32700 tccgctttcc ctacagaaga cacagaaaag catttttgcc tctagatcct tttgtctagg    32760
gtaaattctt agggtgacaa gagtatgcgg caggaagaag gaggagccat aaaggaagag    32820
aagccagctt gttggcatgg ggcatagaaa aggacaaaat ctaggcatga aaaggatgga    32880
taaatactgc aaatattatg ttcttaccca ttcttggaaa cgtcagcttt cttgcttcct    32940
gtgcttccag ccgaggtagg gcaaaggtga gattgagaaa atagccattc agctcaggaa    33000
ggcttctaag taaaggatgg atttgga                                        33027
```

<210> SEQ ID NO 19
<211> LENGTH: 20511
<212> TYPE: DNA

<213> ORGANISM: Homo sapiens
<220> FEATURE:
<221> NAME/KEY: misc_feature
<222> LOCATION: (1)..(20511)
<223> OTHER INFORMATION: TIPIN

<400> SEQUENCE: 19

```
ggagttcccg agtatcgcga aagcgcgct tagtctgcac gccgaggtcc gcgctgtgtc      60
ccgtgttttc tgcgtgaggt gagagctggc tggcgggcca atgaagttct tgcggggaga    120
ggggagtcgg actagccagg gagccagatg gaagagccag ggagccagac agactagcgg    180
gaaagcctaa ttgtcgcagg aaggggtca ggaggttggg gggtcgacct gacccggcct    240
ggagaggcgg ggaggtgggc gcgtgtcccg gttgcttagg ttttgggatg cctcttactc    300
tgccaagccg cttagcggga gggaacgtgt tcctgatcat cttaccccca ggcttctgtc    360
cggggcgtgt caatgtagaa atcccccagc gaatgttgga tgaatgaatg aagttgaaga    420
gagggtaggc ggggaacgag gatgaggggg acggctggag aagaggtatg ggaggttcga    480
tgtttcaggg atggcaccca aggggacat cgaggcagca cggtagcact tcctttgcga    540
tgagggggcgt ctctttggac ttcttggaaa agaggtgggc attggaaacc agggtctggg    600
aacaaaccgt ggtttggaca taacatttgt taccttcact cttctgggag ttggagaagt    660
agaggaggaa gttcagacaa tttcataagt gtctaaaaag agacagttat gcgaccattg    720
acgaggagta aaagtcgtct attgagcatc ttattcacta caaatagaag aaagaaatac    780
cagtttcctg acaagcccca ccccatgctt ggccagttcc tgagtacact taatatattt    840
taggtactgt catcaaactc aaagctcgct gtcagcctca aaggtctgaa ccctagtata    900
gattcttgta gcttgcttga agttacagtg ggtcatgatc aggaattgat gctttgtttt    960
tgttttgaaa cggagtctcg ctctttcgct caggctggag tgcagtggcg cggtctcggc   1020
tcactgcaag ctccgcctcc tgggttcaaa tgattctcct gcctcagcct cccgagtagc   1080
tgggactaca ggcgtgtgcc accacgcccc gctaatttt tttgtatttt tagtagagat   1140
ggggtttcac tgtgttggcc aggctggtct cgaactcctg acctcatgat ccgtccgcct   1200
ctgcctccca gtgctggg attaccggcg tgagccaccg cgcccagccg atgctttgct   1260
tttatattta tggtaaccga aatttagaat tagtgagatt ttaaagatcg tctaactcca   1320
atttggggaa actggaattt ttttttgcat tccatcattc atcaaatata tattgagcac   1380
ctggggccgg gcgcgatggc tcacgcctgt aatcccagca ttttaggagg ccgaggcggg   1440
cggatcacga ggtcaggaga tcgagaccat cctggctaac acggtgaaac accgtctcta   1500
tgaaaaatac aaaaaattag ccgggcgtgg tggcaggcgc ctgtagtccc agctattcgg   1560
gaggctgagg caggagaatg gcgagaaccc gggaggcgga gcttgcagtg agcagagatc   1620
gcgccactgc actccagcct gggtgacaga gcccgagact ccttctcaaa aaaaaaaaa   1680
aaaaaaaaag atatatattg agcacttgct gtgtaacagc attggggttc cagctgtgta   1740
acacagagag acttaacctc gttgcccttt ttgagctaca gtctagtttg ggagacgaac   1800
aataaataac tgtataaata aaacctgata ttgaaactgg ataagtgcca tgacacttgt   1860
acttgacact atgaatgctt actaaagaag gatttagaga aattgaggta aacttttgaa   1920
aaggtgatag ttgagatctg gaagatatta ggagtcaagg aatagctttt tcaagacagg   1980
aaatagtatt tgtaaagagc cagtggcctg agggatatag ctctttcaag gaaagaaaaa   2040
gcatagagta gtgtgaagtg agactggtga ggtagtaaga ggctggatca cacagggcct   2100
tgaagttttg tctttatctt aagagcaatc agaaaccatt gaaatactta atccaagtga   2160
```

```
ggtgatcagc tttatatttt cagattcagt ctagatgtaa tagggacaat tgaaggagac    2220
gagtggatga gagtagtgga gtaatgcaag caagaaatgt tgggaagtgg ttatagagat    2280
aaggagaaat agacagattc aagggatatt taggaaataa gatgggcagg atctgtggga    2340
taggggaagg aattgctaaa gatgacttgt aggtttctga attgcatagc tggatagatg    2400
tcatttaatg agttaggaaa atttagaagt ttggttttgt acctgctgag ttacaggtgc    2460
ctttcaggcg tttaggaagt gtaaaatggg aagtagtgat ctggatcgca gagtcaaggc    2520
ctagggtaga gataaaaatc agggagtcat ctataaatca gtacttatta aagctctgtg    2580
cataaatgaa tgaagaagcc ctaggatgga gtcttggata cttaatggcc ggggtagaag    2640
ataaacctgc aaagaaaatc caggaggagt gcccagaaag ggaggaaagc ctcagcctcc    2700
tgagtagctg ggactacagg tgcgtgccac aacacctggc taaatttttt ttatattttt    2760
agtagagacg gggtttcact gtgttggcca ggctggtctc gaactcctga cctcatggtc    2820
cgtctgcctc tgcctcctgc tgggattacc ggcatgtctt agaagttaag gtaaacattt    2880
ttcccagaaa aaaactgacc aaaagtgtca gttgttattg agaagttaag taaggcagta    2940
ctgaaaaaca ttctttcgag ttatcaacct gaggataatt tcccattcag gaaaccttac    3000
ctagaagacc aatatgtaaa cacatttaaa aatttttttt tattttaat ttttgtgggc    3060 acgtagtagg tgtatataaa cagatttttt ttttttttt tgagacagag tgttggtctg    3120
tcgcccaggc tggagtgcag tggcggcatc ttggcttact gcaagctccg cctcctggat    3180
tcacgccatt ctcctgcccc agcctgccga gtggatggga ctacaagcgc ccgccaccac    3240
gcctggataa tttttttgtat ttttagtaga cgggggttt caccgtgtag ccaggatggt    3300
ctcgatctcc tgacctcgtg atccgcccgc ctcggcctcc caaagtgctg ggattacagg    3360
cgtgagccac cgcgcccagc ccagattttt ttttttaag cagctctaat tgaagtgggg    3420
gtgaagtacc tatatcctgc gtatttcata ccctattgga tcacagtttg aaaccctctg    3480
aaaagtcaaa ttcatctttt tatggtaggg gaaactcaat agttgaggta aaaggatttg    3540
ttcaaaatga tatagttatt tagtgttagg gtctacattg gaacttagat ttctaggcta    3600
gtcttttttt tcataattag tatcttctct acttttcatg atgtgtgagt ttgaaatgtg    3660
gtctaactga ttgaaacaca tgaaatggct gcaggtagaa cttgtctata tagtggagac    3720
tattttggat gaatacaaat aactttaatt ttttccccta gaggaaaaga tgctagaacc    3780
acaggagaat ggcgtgattg acctaccaga ttatgagcat gtagaagatg aaacttttcc    3840
tcctttccca cctccagcct ctccagagag acaagatggt gaaggaactg agcctgatga    3900
aggtatgtat agagagtttt aaaaggagg ctgtgaggcc aggcacggtg gctcatgcct    3960
gtaattccag cactttggga tgctgaggcg ggcggatcac aaggtcagga atttgagacc    4020
agcctggcca catggtgaaa atcccgtctc tactaaaaat acaaaaatta gccggggtgt    4080
ggtggctgtg gtaaaaggta tttgaggaga aaaagaaaa aaaaggaggc tgggcacagt    4140
gggtcctgcc tgtaatccca gcactttggg aggccgaggc aggaggatgg cttgagccca    4200
ggagttcaag accagcctgg cgagacctca actctactaa agatttaaaa attagccggg    4260
tgtggtaggc agcacctgta cttccaggta ctcgggatac tgaggcagaa gaatctcttg    4320
agcctaggag tttgaggctg cagtgagcca agatcgcacc actgcactcc agcatgggca    4380
acagagtgag accctgtttc aaaaaaaggt gtcccatgtt tagttatctt atcagcttgg    4440
aaatgataca taataaataa tacaaatcat ttaagtacag taatactgaa tcgtggtttg    4500
```

| | |
|---|---|
| tttcaccaga gtcaggaaat ggagcacctg ttcgtgtacc tccaaagaga acagttaaaa | 4560 |
| gaaatatacc caagctggat gctcagaggt acatttacta tattcttata catttatact | 4620 |
| ttttattttt aatatccatt gttttcttc taatgttata aacttttggt tggtatgatg | 4680 |
| tggagctctt atatttctaa aaactttttt ttagttcagc agaacatatt ttttcttatg | 4740 |
| gtcttgcttt ggaccaaact ctagaaaact tgaaattagg ctgggcgtgg tagctcacgc | 4800 |
| ctataatccc agctctttgg gaggcctacg tgggcggatc acgaggtcag gagattgaga | 4860 |
| ccatcctggc taatacggtg aaaccccgtc tctactaaaa atacaaaaaa ttagctgggt | 4920 |
| gcagtggtgg gtgcctgtag tcccagctac ttgggaggct gaggcaggag aatgacgtga | 4980 |
| acctggggga ggccgagctt gcagtgaccc gagatcgcgc caccgcatcc cagcctgggc | 5040 |
| gacagagtga gactccgtct caaaaaaaaa aaaagaaaa taaaacttga aattaaaaac | 5100 |
| atacttttat tcacagatta atttcagaga gaggacttcc agccttaagg catgtatttg | 5160 |
| ataaggcaaa attcaaaggt aaaggtcatg aggtaagaac tgattttat gttagacctt | 5220 |
| tgttttttaa aatagcaata aaaatgtgga cccattatga tcttggaaat ctcagaatgc | 5280 |
| tttaagatac tatccttagt cgtcgtatgt cttgagaaac agttgtgatg tactagaaag | 5340 |
| ggaactgttt gaagaattag aaagcatgtc ttgtgcagtc tcattttttg ctgcttaaac | 5400 |
| cttggctata ggaaaatcac acctgtgtct gtaaagtctc agttttatt ttataattta | 5460 |
| caggaataaa atttactttg tctacctcaa agttttaaat ttcatgaggg caaggactct | 5520 |
| gcctgtatca gtcacttatg tgtccccaag atgtggcaca gtgcctggtt cataataaat | 5580 |
| gtcagtaaag tgtggttaaa aaatgaatac atttagtaac tgaatcactt tacaaatgca | 5640 |
| cattttgaaa tctatttttg aattatgtag gagtgtaggt ataatttttt gcagatgata | 5700 |
| gtatatttt agagagtttt gtagtttttc aagtgtttct aatatctaat atattctttt | 5760 |
| tttttttttt tttttttaa gacggagtct tgcttgctct gttgcccagg ctggagtgca | 5820 |
| gtggcgcaat ctaggctcac tgccagctcc acctcccagg tttacgccat ctcctgcct | 5880 |
| tagcctcccg agtagctggg actacaggcg cccgccaaca ggcctggcta attttttttt | 5940 |
| tttgtatttt tagtagagac ggggtttcac cgtgttagcc aggatggtct tgatctcctg | 6000 |
| acctcgtgat ccgcccgcct tggcctccca aagtgctggg attacaggcg tgagccactg | 6060 |
| cccggcctac tatctttaa ctttattaag tgtttttttt tttgtttttt tgagatgaag | 6120 |
| ttttgccctt gtcacccagg ctggagtgca atggctcgac cttggctcac tgcaacctcc | 6180 |
| gccgcttggg ttcaagcgat tctactgctt cagcctccca gtagctggga ttgcaagtg | 6240 |
| cccaccacca cgcccaacta attttttgtat ttttggtaga gatggggtat caccatgttg | 6300 |
| gccaagctgg tctggaactc ctgactcagg tcatccaccc gcctcggcct cccacagtgc | 6360 |
| tgggattaca ggcgtgagac actgcgcctg gccaacttta ttaagttttt gtactgggat | 6420 |
| tttttttcat ctaatttta tgaatctgta tccaggcggg gtgctatggc tcatgctgta | 6480 |
| atcccagcac tttgggaggc cagggtgggc ggatcacttg aggccaggag ttcaagacca | 6540 |
| gcctggccaa catggcaaaa cctcctctct actaaaaaat acaaaattta ggccaggtgt | 6600 |
| ggtggcgcac acctctaatc ccagctactt gggaggctga gcatgagaa ttgcttaaac | 6660 |
| ccgggaggct gaggttgtag tgagccaaga ttgcgccctt gcacttcagc ttgggtaaga | 6720 |
| aagcgagaat ctctctgaaa aaaccaaaa aaccaaaaa aacaaaaaaa acccctgtat | 6780 |
| ccagtgctct tttagactgc agtcctctaa gttcttaata atttctctc ttttttttgg | 6840 |
| atataggatc tcgctgtcac ccagtctgga gtgcagtggt gtgaacttgg ctcactgcaa | 6900 |

```
cctctgcccc ccaggctcag ggagtccttt cacctcagcc acctgagtag ctgggtccac      6960
aggtgtacac caccatgcct ggctattgtt ttgtattttt agtagatatg gggtctcacc      7020
atgtttccca ggctggtctt aaactcctta gctcaagtga tccgtccccc taggcctccc      7080
atagtgctag aattacaggt gtgaaccact gtgtctggcc aatattttc ttattaaagt       7140 tccttttata agttttcaa ccttataaat ataaaatgac cccagtgatt ttggcatagc       7200
ttttcagttc tgaaagttgc tgacggggtc agctgtgaga atgagactcc tgtttagcat      7260
ttttattttt atgtggcagg ctgaagactt gaagatgcta atcagacaca tggagcactg      7320
ggcacatagg ctattcccta aactgcagtt tgaggatttt attgacagag ttgaatacct      7380
gggaagtaaa aaggaagttc aggtaagtgt tgagatgatt ataaatatca ttcacatgct      7440
aaatggtagg gtagatttag ttgaggctaa attgctgttt aaagtgttca ttttgaaatc      7500
tcttttggta gagagggaaa agtaatagca aattatctcc ccccaacatg attggtaaag      7560
aggtaaaaat aaataatctc ttttcatttt cagacctgtt taaaacgaat tcgacttgat      7620 ctccctatt tacatgaaga ttttgttagc aataatggta agaatatagg tttatctact       7680
ttataacaat tttgcttta gaaatagatc taggcagggt gtggtggctc aaccctgtaa       7740
tcccagcgct ttgcttttt gtttcatgtt tagggacaga atcttgctct gtcacccagt       7800
ctggagtgca gtagcacaat catagcttac tgcagccttc aactcctggg cttaagggat      7860
cctcccgcct cagcctcccg agtagctggg actgcaggtg catgccattg tgcctggcta      7920
attttaaaat ttttgtagag atggggatct ccctgcgttg ccttggctgc tctcacactc      7980
ctggcctcaa gccatactgt gcctggccaa cttttttttt tttgagctgg agtctcactc      8040
tgtagcccag gctggagtgc agtggcatga tctcggctca ctacaacctc catctcctgg      8100
gtcccagttc aagcaattct cctgcctcag cctcctgagt agctgggatc acaggcatgc      8160
gccaccatgc ccagttaatt tttgtatttt tttttttttt tttttttta gtagagatgg       8220 ggtttcacca tgttggccag gctgttttg aactcctgac ctcgtgatcc gcccaccttg       8280
gcctcccaaa gtgctgggat tataggcgtg agccactgcg cctggcttgt tatttttttt      8340
ttgaagacta gccacatgca atagtgaaaa gggaggaaag agtagaacaa ggagtttgat      8400
ctgtgactgt gaattgataa ctcattacct ttggagcaac cccagttctt tgggaggcca      8460
tggaggtagg attacttgaa tcctagagtt ggagatcagc ccgggcaacc gagtgagacc      8520
ccatctacaa aaatttttaa aaagttaatc aggtgtggtg gcacatgcct gttgtagcta      8580
ctcagggggt tgaggcggga ggatcacttg agcccaggag ttcaaggctg cagtgaacca      8640
ggatcacacc actatactct gggcaataaa tagggtgaga gaccttgtct ggaaaaaaaa      8700 aaaaaaaga aagaaagaat agaagtagtt agaggaggca gtattatagg accagatcct      8760
tagtccatat tgtgtatata attagagtat ggtaaagtac aataaataga taagttaaaa      8820
tgccttggta gtgggctggg cgtggtggct catgcctata atcccagcac tttgggaggc      8880
tgaggtgggc agttcacttg aggtcaggag tttgggaaca gcctgaccaa catggggaaa      8940
ccccatctgt actgaaaata caaaaattag ctgagtgggg tggtgcacgc ctgtaatccc      9000
agctactcag gaggctgagg caggagaatt aacttgaatc caggaggtgg aggttgcagt      9060
gagccgagat tgcgtcgttg caatccagcc tgggtgacag agtgagactc ttgtctcaaa      9120
aaaaacaaag ccttggtaca tctagaatgt tgtatatcaa atttgttgta gaatatgaac      9180
ttttgaaaac tctggtgacc cactgatcct atatagcact tgttaataaa aatatatatc      9240
```

```
aagataaaag tgttcatata catatacacc attggataaa gtggtactgg gaaattaggc    9300
aaaataattt atgatgaaag tttgcatttc acttggagcg cagctctcgg atataggact    9360
ttagtgagac ctttgtgact gttcctggta ttgattgcat ttgttagttg tacagtgcaa    9420
ccatagacag tcacacacat taaaacagat ggttcctgcc gacagggtct gtatagttat    9480
cagattttct gtgcgatggc tccatacatg tttgttttg ttttttaact tttaacagat    9540
gtggaagaaa atacaggttc catgtagaat accctaaagt tatttataaa ctactttcaa    9600
acatgtaaag gaatgtgatt taggccgggc gcggtggctc acgcctgtaa tcccagcact    9660
ttgagaggcc gaggcgggtg gatcacaagg tcaggagatc gagaccatcc tggctaacat    9720
ggtgaaaccc cgtctctact aaaaaataat aaaaaaaatt agccgggtgt ggtggcgggc    9780
acctgtagtc ccagctattc gggaggctga ggcaggagaa tggtgtgaac ctaggaggtg    9840
gagcttgcag tgagccgaga tcacgccact gcactccagc ctgggcgaca gcaagactcc    9900
gtctcaaaaa aaaaaaggaa tgtgatttaa ataatccgtg atttaaattt cttggtaaaa    9960
tatggtatgt atggatggca taggattggg tatatgtaaa ggaatgagtt attacagttc   10020
taaattccac agcatatact actgggttac tttttgaggt gcccggtatg tgataaaggt   10080
tcagggctaa aaaaatgact acgatcaggc ccctttgtgg gcaaatacag tagtgaatga   10140
atcagacata caacattgcc agtagtgtgg taggtgttgt aattagaggt atgagtaggt   10200
cgcagggtgg gatgcaaagg agagcatagt tacatgtccc tgggggtaga gggagaactt   10260
cacaaaggag gattcagaag aattttgatt tgggggtgag aggaagaaaa aagaaattaa   10320
aaagaaaaaa agtattttga atgaacagta gaggtcaggc agaggtgatt ttgaatgggg   10380
gagccatcta tgcagaggtg taaattaact tggatttcag gctctatatt ctatggcagt   10440
aaaaaaaaaa aaaaaaaaag ataaattaag gccaggcgca gtggctcacg cttgtaatcc   10500
tagcactttg ggaggccaag acgggcggat cacttgaggc caggagttcg agaccagcct   10560
ggccaacatg gtgaaacccc atctctacta aaaatacaaa aaattagcct ggcgtagtgg   10620
cacatgcctg taatcctagt tactcgggag gctaaggcag tagaattgct tgaacccgga   10680
aggcggaggt tgcagtgatc cgagattgcg ccattacact ccagcctggg caaaagagt    10740 gaaactctgt ctcaaaaaaa aaaaaggag ataaattaac atggaccatt cagagaatta   10800
caagcatgct gaaatatagg gtacaaataa gagaactgaa tctgagattt ttgtttgttg   10860
tgtcatatat ttaatttgta tcttaatagt ctccaaattt ttttgatcag gtgccacaga   10920
agtaaaaatg ttttgaccat tttatttgtt gattaaatac atttacttct atacggatgt   10980
gatttgtaat gtactttttt tttttgaga cggagtctca ctctgttgcc taggctggag   11040
tgcagtggtg cgatctcggc tcactgcaac ctccacctca gttcaagtga ttctcctgcc   11100
tcagcctccc agtagctggg attacaggtg tgcaccacca cacctggcta attttgtat    11160 ttttagtaga cagggtttt catcacgttg gccaggcttg tctcaaactc ctgatttcag   11220
ttgatccacc tgccttggcc tcccaaagtg ctagagttac aggcgtgagc cagtgagcca   11280
ctgtgcccgg cctaaattta gtttttgtag tgacaggatc tcactatgtt gcccaagctg   11340
gtctgtatct cctggcctca acagtctgc cttggcctcc caacgtgccg ggattacagg   11400
tgtgagccac tgtgcttggc ctccagctgt tccttggaca tttcaggcac attttattc    11460 taaggctttt gtattgccgt actctgcctg gaacactctt cccttgtacc cctcaagtcc   11520
gcatgactgt cttacactcc tcaaactgtg ctcaaatgac aacttggtga agcctcccca   11580
ttacactgtt atagttgcat ccccactccc atcatttctg actcccctat gctgtttcct   11640
```

```
tttgcattgc ccttgtttcc ctttaatttt tatatagttt acttatgttt tagtttgtct   11700
ttactacaat gacggcatcc tgtaacacac tgaatatttc tagctttagc ttcttttgcca  11760 taatcacttg ccaatgaatg ttgcagtaaa tgaatttcat gcgtacttct aattttttaa   11820
aatttcattt ttatttactt atttcttttc gaggcagggc ctcactctgt tgcccagggt   11880
ggagcacagt ggcatgatca tagctctgca gcctcgacct ccagggctta agcaatcctg   11940
ccacctcagt ctcctgagta gtttggatta caggcatgca ccacctgcct gcccaagttt   12000
ttcttttttt ttttttttctt tttttttttg tagagaaagg gtctccctat gttttgcagg   12060
ctggtctcaa actcctgggt ccatgtgatc ctcccacctt gggttcccaa agtgctggga   12120
ttataggcgt gagctgctgc acccagcttt aaatctcatt ttaatcctac tcaaaggaac   12180
cagctgctgc ttacaaaata tattgtttat ataaataggt catttactac tgaagatacc   12240
tttgttttct tggttcataa aaagtagttt tttgcttttt tttttacttt tttttgtaat   12300
agagacgagg tcttgctatg ttggtgatgt tggtcttgaa ctcttgttct caagcaatcc   12360
ttctgcctca atctcccaaa gggccatgat tacaggcgtg agccaccttg tccagtcaaa   12420
attagttctt tgagttcatt tgaagccagg agttagggac cagagtggtc aacacctata   12480
gtcccagcta tttagaaggc tgaggcagga ggatcctttg agtccaagga gtttgaggct   12540
ggagtgagct atgatcatac cactgtactc tagcctgggt gacagagtga gtccccatct   12600
cttgaaaaaa acaaaaaaaa agtagttatt tatgtatttt cttattgatt tagaatcctg   12660
caaccctgta agatgaagca cattaaaaac cccatgtttc ataagtggtt cttttttttga  12720 gacggagttt cactcttgtt gcccaggctg gagtgcagtg gtgtgatctc ggctcactgc   12780
aacctctgcc tcccgggttc aagtgattct cctgcctcag cctcctgagt aggtgggatt   12840
acagtcatgt gccaccatgc ccgactaatt ttgtattttt agtagagacg gggtttcacc   12900
atgttggtcc gactggtctt gaactcctca cctcaggtga tctgcctgcc tcggccccca   12960
aaagtgctgg gattacaggt gtgggccact gcgcctggct cataagtggc tctaatgctt   13020
gtttcttaac tgcttcagca atgtttcata catatactct tatcagtatt tcctgacaat   13080
ggaggccatt ttagtttctt cctacatttt tgttttccat gtcaggaagg aaaagtggct   13140
tttcgttttt cactattaag gaagaaacct taaaagggag tttgattgta aagggctgaa   13200
ttaagtatca tgattttaa atctcactga aataattgta aaggtctgtc tttatgtttt   13260
aaatgttttt ttaattgtga tagttttct ataattagct aatatttcaa ggcataatat   13320
atacatagaa caaggataat gtatataaat atttcaaatg gtgacttgaa ttttttgacc   13380
aacttgtcag atgtgatggg gtttatcttt cttttaattt cataatatgg atgatgtaga   13440
tagaaggtaa agtgtcagct ctgctgtttt tttttatttt tgcttgtgct tctattctac   13500
ctacaggcat tttgttattt tgtagaatct ttttaaccta acacttgtac attttgttgg   13560
ggttgtttgg ttaaattagt aagatgaaat ccatcagttt atttgactgg gcaatcagaa   13620
acagctgtat atctgacatt gtaaagtcag tgggggcccc attctccacc cttttacaat   13680
atggatcttg cctatagagt ggctcacaga tcagacagta actctgtcat aaggacaagg   13740
gacagttaac cactgccagt cttatttttaa atatgttagt aaaacatagt ttttcttaat   13800
tcttaaatga aatataaatg gaagatctat tatttacttt aataccactg tggatcatgt   13860
tggggacatc ctaccttgag ttaactggtt tacaggggct taataatgta ttacttataa   13920
tgtagagcac actgaattta aaaagaaatt aatttggaaa tatgtccata aagttttaaa   13980
```

```
tttcttttct tttttcattt gtctgtgttt aactctacaa aagataatgt cctacataaa   14040 attaccttt  actggccggg tgcattggct cacgcttgta atctcagcac tttgggaggc   14100
tgaggcatgt ggatcacctc aggtcaggaa tttgagacca gcctggccaa tacggtgaaa   14160
ccctgtctct actaaaaata caaaaattag ctgggcatgg tggcgggtgc ctgtaatccc   14220
agcttctcgg gaggctgatg gaggagaatc acatgaatct gggaggcgga ggttgcaatg   14280
agccaagatc gaaccattgc actccagcct gggtgacaag agtgaaactc cgtctcaaaa   14340
aataaaataa aatgtattaa aattaccttt tcccatattg acactgggaa actattgaaa   14400
tgtgttggtt taatgtagaa caagaatatg gtttggattc cttaagctct ttgattaggc   14460
caagcataaa atatttctaa ttacaatcaa gaacttttg tttctttctt ttttttttt    14520 ttttttttg  gagacagtct tgctctgtag cccaggctgg agtgcagtgg cgcaatcttg   14580
ctcactgctg cctccgcctc ccgggtcccg gttcaagcaa ttctcctgcc tcagcctcct   14640
gagtagctgg gattataggc atgcgccacc atgcccagct aattttgta ttttagtag    14700 agatggggtt tcaccatgtt ggccagactg gtcttgaact cctgacctca tgatccaccc   14760
gcctcggctt cccaaagtgt tgggattaca ggcgtgagcc accgcgcccg gccttcatgc   14820
atattttaaa ttgtattttt atttgactta gcattcctct ttaaactgat ttataaatat   14880
ttcttattta attgaatcaa gcatgtattc acaacattct tttttttttt tttttttttt   14940
tttttttttg agacgagtc  tcgctctgtc gcccaggctg gagtgcagtg gcgggatctc   15000
ggctcactgc aagctccgcc tcccgggttc acgccattct cctgcctcag cctcccaagt   15060
agctgggact acaggcgccc gccactacgc ccggctaatt ttttgtattt ttagtagaga   15120
cggggtttca ccgtgttagc cgggatggtc tcgatctcct gacctcgtga tccgcccgcc   15180
tcggcctccc aaagtgctgg gattacaggc gtgagccacc gcgccggcc  cacaacattc   15240 ttatacttca caaattgttt tttcaggtct gtcaccttgc cactttaaat tctttttcaa   15300
tgagaagccc ttctctaact agtctaacac cacagatgta ctatttcttt tctattgcag   15360
atgaagttgc ggagaataat gaacatgatg tcacttctac tgaattagat cccttctga   15420 caaacttatc tgaaagtgag atgtttgctt ctgagttaag tagaagccta acagaagagc   15480
aacaacaaag aattgagaga aataaacaac tggccttgga agaaggcag  gcaaagctgc   15540 tgagtaatag tcagacccta ggaaatggta aattttatgc caaatttat  atgctaccat   15600 taatatatca aggacatgtt agaaattta  acttctctgc tagcccccaa aataaaatac   15660
ttctaggagt ggaaaagtgt gatattaagt ttatgtatat tttagagaca gtgtgtgtga   15720
gagaggagag agagaatggc tgtgttcctt aaagaataaa tgaatccaag atggttttct   15780
ggatagctga gtacctctta aaaaattatt ttaatcacct ggccaggcgt ggtggctcat   15840
gcctgtaatc tcagcacttt ggaggccaa  ggtaggtgga tcgcttgagg tcaggagttc   15900
aagaccagcc tggccaacat gatgaaaccc catctctact aaaattacaa aaattagcca   15960
ggtgtggtgg tgcacaccag taatcccaac tacttgggag gctgaggtac gagaatcacc   16020
tgaatcaaga aggtggagat tgcagtgagc caagatcgtg ccactgcact ccagcctggg   16080
tgacttgagt gagacgctct caaaaaaaaa agaatttatt ttaatcactt gaaattgatt   16140
ttaaattctt aataaacatt cttccctgac tccttaaagc atgtgccata tactattacc   16200
tttaggacaa taattataac aataaataaa gaaaaaata ggccaggtgc agtggctcat   16260
gcctgtaatc ccagcacttt aggaggccaa agtgggccat cacccgaggt cagcagttca   16320
agaccagcct ggccaacatg gtgaaacccc acctctacta aaaatacaaa aattaactgt   16380
```

```
gcatggtggt gtgcacctgt aatcccagcc acttgggagg ctgaggcagg agaattgctt   16440
gaacccagga ggcagaggtt gcagtgagct gagatcaacc cattgcactc cagcctgggc   16500
aacaagagca aaactccatc tcaaaaaaaa aaaaaaaaa aaaaaggcca ggcgcagtgg    16560
ctcacgcctg taatcccagt actttgggag gctgaagtgg gtggatcaca aggtcaggag   16620
atcgagacca tcctggccaa catggtgaaa acccgtctct actaaaaata caaaaatttg   16680
ccgggcatgg tggtgtgtac ctgcctgtaa cccagctgc ttgggaggct gaggcaggag    16740
aatcgcttga acctgggagg tggaggttgc agtgagctga gatcgggcca ctgcactcca   16800
gcctgggtga cagagcaaga ctccgtctca aaaaaaaaa aatgctttt cttgtgtttt     16860 gtcacttggt tgtgagctgt acttttgaaa gtagctgttt aatttgctta tctttagcat   16920 tccctttca cttctaaaac tgcctgaaga tttgctttat taaaaatat attattagta     16980 tttttagaaa cgttgtcaat ctgtcaccca ggctagagtg cagtggtgtg atcttgactc    17040
actgcagcct tgaacttcta gtctcaagca atcctccagc attgggcttc caaagtgctg    17100
ggattgcagg tatgagccag tgtacctggc ctaaatttgc tgttttaac acacattgtg     17160 ggtttggaaa ctatataacc aaatttgtta aaactatatt tagaaagaat tgcaagttgg    17220
ttttgaatga agtaagcagg attgcgtata tcttcttaa tttcccattc agttttcct      17280 ttcaaaatgg aaaataaga attataggcc cagcacagtg tctcttgcct gtaatcccag     17340
cactttggga ggctgaggtg ggcagatcac ttgagcctgg gagttcaaga ccagcctggg    17400
caacatagtg agtccccgtc tctacaaaaa aaaaagaat tataataact agataccatg    17460
ttgtaaacga agtttcaccc aatatattaa cattttaag tgaaaattat tttggctact     17520
ttttttttca gttaagatga attacttt tcttttgct ttttttttt tttttttt           17580 tttttgagat ggagtcttgc tctgtagctc aggctggagt gcagtggcgt gatcttggct    17640
cactgcaacc tctgcctccc gggttcaagc agttccctg cttcagcctc ctcaagtagc     17700
taggactaca agtgcgtgcc cccatgcctg gctaatttt gtattttag tagagaaggg     17760 atttcactgt gttggccagg gtggtcttga actcctgacc tagtgatctg cctgcctcag    17820
cctcccaaag tcctgggatt acaggtgtga gccaccatgc ccagctgaat ttactttttc    17880
cttttttttt ttttttttt tttgagacgg agtcttgctc tgtcacccag gctggagtgc    17940
aatggcgtga tctcggctca ctgcaagccc gcctcccgt gtccatgcca ttctcgtgcc    18000
tcagcctccc gagtagctgg gactacaggt gcctgccacc acgcctggct aattttttgt    18060 attttagta gagacagggt ttcaccgtat cagccaggat ggtctcgatc ccctaacctc     18120
gtgatccacc cacctcggtc tcctaaagtg ctgggattac aggtgtgagc caccgcacct    18180
ggccaattta cttttctttt ataaatggat gttttattag taccatgtga acattacat     18240 gaagatagca ttattcttga tggcagtggc ttctttgctg tcaatatcaa gtatacctgg    18300
cagttggtat ttaaagctca cctctgtta tcatatacaa cttaaaattt gtccaaatgg     18360
aaataagtac tttaaagttt cttatggatc actctgacat aaaacctaaa cgcacttggt    18420
ttttattaga cctcttccta gtagttttca gttttgtttt tttagatggg gcctcactgt    18480
attgcccagg ctggagtgca gttgctgatc tcggcccact gcaacctccg cctcctaggt    18540
tcaagcgatt ctcctgtccc agcctcccga gtagctggga ttacaggcgt gctccaccat    18600
gtccggctaa ttttttgtatt ttttgtagag gcagggtttc accatattgg ccagactggt   18660
ttcaaactcc tgaccttgag tgatctgcct gcctcagcct cccaaagtgc tgagattaca   18720
```

```
ggcatgatcc actgtgcctg ccaatagta gtttgatttt gaataagaac agttacattt    18780
gactatgatc caagagtgtg agttgaataa cattcaaaac cattttgctt tttttttgtt    18840 ttttttggt  tataggatct cactttgtca cccaggctgg agtgcagtgg cacgatcatg    18900
gttcgccacc atagccagct aattattttt tttttattt tatttttttt gatgttttgt    18960
tgacatgggg tctcactatg tggcccaggc tggtcctgaa ctcctgagct ccaatgatcc    19020
tcccacattg ttgggatcgg gcctggcctc tcttgcattt aaaatggatc ttaattgtat    19080
aaaaatgggc ttattggcta ggcgtggtag ctcacgcctg taatcccagg actttgggag    19140
cctgaggcgg gtggatcacc tgaggtcagg agttcgagac cagcctggcc aacatagtga    19200
aaccctgtct cttctaaaaa taccaaaatt agccgggtgt agtggcgggt acctgtaatc    19260
ccagctactc gggaggctga ggcaggagaa tcacttgaac ccggtggagg ttgcagtgag    19320
cccagatcgt gcgattgcac tccagccaaa gtgatggagc gagactccat ctcaaaaaaa    19380 aaaaaaaga tatttaga agaaagtgat cataattaac attaagtgat cttagacttc    19440
attttactaa actgagcttt tgaagaggtt tgtactcatg cggtaagatt ggatcaggta    19500
cttataatga ataataatgg tatgatttct ttcagatatg ttaatgaata cacccagggc    19560
acacacggtt gaagaggtta atactgatga ggatcaaaag gaggagtcaa atggattaaa    19620
cgaagacatt ctggacaatc catgtaatga tgctattgcc aatactttaa atgaagagga    19680
aacactgctg gaccagtctt ttaaaaatgt gcaacagcaa cttgatgcta catccagaaa    19740
tattactgaa gctagataag tttccattaa gagaaaatgt atctgttaag tcatcgtcct    19800
gcaagcttgg cgttactatg tattttttct tcttggagtg aaaatcctta gatagtaaaa    19860
ctgttataga ttattgttta aaatctgata atctggtatt tatttataat tatgcttgtc    19920
actttagtta aatctatttg ttctctttag tgtttgtttt tatataggta tttcttcata    19980
aaatgattag gaggtaataa gcagtttctg ctgctggtct gtcattgaat gccttgtttt    20040
cactaagttg ggaggttttg tttctgtttt ttactgctcc ttgcaaagca gggctaatcc    20100
atggacagtg tgcccagagt agtctagttg aagtttttg ttttgttttg ttttgttttt    20160
tttgacacag agtctcactc tgttggccag gctggagtgc agtggcacag tcttggctca    20220
ctgcaacctc tgcctcctgg gctcaagcaa ttctcctgcc ttagcctccc gagtagctgg    20280
gactacaggc gtgtgccacc acgcttggct aattttgta cttttagtag agatgaggtt    20340
tcaccatgtt ggccaggctg gtctcaaact cctaacctca ggtaatccgc cccctcggc     20400 ctcccaaagt gctgggatta caggtgtgag ccaccgcgcc cagcctgggt gaagttttga    20460
gatgtacata tatactgaat attaatgtca attttttaaa agaagtaaaa a             20511
```

<210> SEQ ID NO 20
<211> LENGTH: 1339
<212> TYPE: PRT
<213> ORGANISM: Homo sapiens
<220> FEATURE:
<221> NAME/KEY: MISC_FEATURE
<222> LOCATION: (1)..(1339)
<223> OTHER INFORMATION: CLSPN

<400> SEQUENCE: 20

Met Thr Gly Glu Val Gly Ser Glu Val His Leu Glu Ile Asn Asp Pro
1               5                   10                  15

Asn Val Ile Ser Gln Glu Glu Ala Asp Ser Pro Ser Asp Ser Gly Gln
            20                  25                  30

Gly Ser Tyr Glu Thr Ile Gly Pro Leu Ser Glu Gly Asp Ser Asp Glu

```
                35                  40                  45
Glu Ile Phe Val Ser Lys Lys Leu Lys Asn Arg Lys Val Leu Gln Asp
 50                  55                  60

Ser Asp Ser Glu Thr Glu Asp Thr Asn Ala Ser Pro Glu Lys Thr Thr
 65                  70                  75                  80

Tyr Asp Ser Ala Glu Glu Asn Lys Glu Asn Leu Tyr Ala Gly Lys
                 85                  90                  95

Asn Thr Lys Ile Lys Arg Ile Tyr Lys Thr Val Ala Asp Ser Asp Glu
                100                 105                 110

Ser Tyr Met Glu Lys Ser Leu Tyr Gln Glu Asn Leu Glu Ala Gln Val
                115                 120                 125

Lys Pro Cys Leu Glu Leu Ser Leu Gln Ser Gly Asn Ser Thr Asp Phe
                130                 135                 140

Thr Thr Asp Arg Lys Ser Ser Lys Lys His Ile His Asp Lys Glu Gly
145                 150                 155                 160

Thr Ala Gly Lys Ala Lys Val Lys Ser Lys Arg Arg Leu Glu Lys Glu
                165                 170                 175

Glu Arg Lys Met Glu Lys Ile Arg Gln Leu Lys Lys Lys Glu Thr Lys
                180                 185                 190

Asn Gln Glu Asp Asp Val Glu Gln Pro Phe Asn Asp Ser Gly Cys Leu
                195                 200                 205

Leu Val Asp Lys Asp Leu Phe Glu Thr Gly Leu Glu Asp Glu Asn Asn
210                 215                 220

Ser Pro Leu Glu Asp Glu Glu Ser Leu Glu Ser Ile Arg Ala Ala Val
225                 230                 235                 240

Lys Asn Lys Val Lys Lys His Lys Lys Glu Pro Ser Leu Glu Ser
                245                 250                 255

Gly Val His Ser Phe Glu Glu Gly Ser Glu Leu Ser Lys Gly Thr Thr
                260                 265                 270

Arg Lys Glu Arg Lys Ala Ala Arg Leu Ser Lys Glu Ala Leu Lys Gln
                275                 280                 285

Leu His Ser Glu Thr Gln Arg Leu Ile Arg Glu Ser Ala Leu Asn Leu
                290                 295                 300

Pro Tyr His Met Pro Glu Asn Lys Thr Ile His Asp Phe Phe Lys Arg
305                 310                 315                 320

Lys Pro Arg Pro Thr Cys His Gly Asn Ala Met Ala Leu Leu Lys Ser
                325                 330                 335

Ser Lys Tyr Gln Ser Ser His His Lys Glu Ile Ile Asp Thr Ala Asn
                340                 345                 350

Thr Thr Glu Met Asn Ser Asp His His Ser Lys Gly Ser Glu Gln Thr
                355                 360                 365

Thr Gly Ala Glu Asn Glu Val Glu Thr Asn Ala Leu Pro Val Val Ser
                370                 375                 380

Lys Glu Thr Gln Ile Ile Thr Gly Ser Asp Glu Ser Cys Arg Lys Asp
385                 390                 395                 400

Leu Val Lys Asn Glu Glu Leu Glu Ile Gln Glu Lys Gln Lys Gln Ser
                405                 410                 415

Asp Ile Arg Pro Ser Pro Gly Asp Ser Ser Val Leu Gln Gln Glu Ser
                420                 425                 430

Asn Phe Leu Gly Asn Asn His Ser Glu Glu Cys Gln Val Gly Gly Leu
                435                 440                 445

Val Ala Phe Glu Pro His Ala Leu Glu Gly Glu Gly Pro Gln Asn Pro
450                 455                 460
```

```
Glu Glu Thr Asp Glu Lys Val Glu Pro Glu Gln Gln Asn Lys Ser
465                 470                 475                 480

Ser Ala Val Gly Pro Pro Glu Lys Val Arg Arg Phe Thr Leu Asp Arg
                485                 490                 495

Leu Lys Gln Leu Gly Val Asp Val Ser Ile Lys Pro Arg Leu Gly Ala
            500                 505                 510

Asp Glu Asp Ser Phe Val Ile Leu Glu Pro Glu Thr Asn Arg Glu Leu
        515                 520                 525

Glu Ala Leu Lys Gln Arg Phe Trp Lys His Ala Asn Pro Ala Ala Lys
    530                 535                 540

Pro Arg Ala Gly Gln Thr Val Asn Val Asn Val Ile Val Lys Asp Met
545                 550                 555                 560

Gly Thr Asp Gly Lys Glu Glu Leu Lys Ala Asp Val Val Pro Val Thr
                565                 570                 575

Leu Ala Pro Lys Lys Leu Asp Gly Ala Ser His Thr Lys Pro Gly Glu
            580                 585                 590

Lys Leu Gln Val Leu Lys Ala Lys Leu Gln Glu Ala Met Lys Leu Arg
        595                 600                 605

Arg Phe Glu Glu Arg Gln Lys Arg Gln Ala Leu Phe Lys Leu Asp Asn
    610                 615                 620

Glu Asp Gly Phe Glu Glu Glu Glu Glu Glu Glu Met Thr Asp
625                 630                 635                 640

Glu Ser Glu Glu Asp Gly Glu Glu Lys Val Glu Lys Glu Glu Lys Glu
                645                 650                 655

Glu Glu Leu Glu Glu Glu Glu Lys Glu Glu Glu Glu Glu Glu Glu Glu
            660                 665                 670

Gly Asn Gln Glu Thr Ala Glu Phe Leu Leu Ser Ser Glu Glu Ile Glu
        675                 680                 685

Thr Lys Asp Glu Lys Glu Met Asp Lys Glu Asn Asn Asp Gly Ser Ser
    690                 695                 700

Glu Ile Gly Lys Ala Val Gly Phe Leu Ser Val Pro Lys Ser Leu Ser
705                 710                 715                 720

Ser Asp Ser Thr Leu Leu Leu Phe Lys Asp Ser Ser Ser Lys Met Gly
                725                 730                 735

Tyr Phe Pro Thr Glu Glu Lys Ser Glu Thr Asp Glu Asn Ser Gly Lys
            740                 745                 750

Gln Pro Ser Lys Leu Asp Glu Asp Ser Cys Ser Leu Leu Thr Lys
        755                 760                 765

Glu Ser Ser His Asn Ser Ser Phe Glu Leu Ile Gly Ser Thr Ile Pro
    770                 775                 780

Ser Tyr Gln Pro Cys Asn Arg Gln Thr Gly Arg Gly Thr Ser Phe Phe
785                 790                 795                 800

Pro Thr Ala Gly Gly Phe Arg Ser Pro Ser Pro Gly Leu Phe Arg Ala
                805                 810                 815

Ser Leu Val Ser Ser Ala Ser Lys Ser Ser Gly Lys Leu Ser Glu Pro
            820                 825                 830

Ser Leu Pro Ile Glu Asp Ser Gln Asp Leu Tyr Asn Ala Ser Pro Glu
        835                 840                 845

Pro Lys Thr Leu Phe Leu Gly Ala Gly Asp Phe Gln Phe Cys Leu Glu
    850                 855                 860

Asp Asp Thr Gln Ser Gln Leu Leu Asp Ala Asp Gly Phe Leu Asn Val
865                 870                 875                 880
```

Arg Asn His Arg Asn Gln Tyr Gln Ala Leu Lys Pro Arg Leu Pro Leu
            885                 890                 895

Ala Ser Met Asp Glu Asn Ala Met Asp Ala Asn Met Asp Glu Leu Leu
        900                 905                 910

Asp Leu Cys Thr Gly Lys Phe Thr Ser Gln Ala Glu Lys His Leu Pro
        915                 920                 925

Arg Lys Ser Asp Lys Lys Glu Asn Met Glu Glu Leu Leu Asn Leu Cys
    930                 935                 940

Ser Gly Lys Phe Thr Ser Gln Asp Ala Ser Thr Pro Ala Ser Ser Glu
945                 950                 955                 960

Leu Asn Lys Gln Glu Lys Glu Ser Ser Met Gly Asp Pro Met Glu Glu
                965                 970                 975

Ala Leu Ala Leu Cys Ser Gly Ser Phe Pro Thr Asp Lys Glu Glu Glu
            980                 985                 990

Asp Glu Glu Glu Glu Phe Gly Asp Phe Arg Leu Val Ser Asn Asp Asn
        995                 1000                1005

Glu Phe Asp Ser Asp Glu Asp Glu His Ser Asp Ser Gly Asn Asp
    1010                1015                1020

Leu Ala Leu Glu Asp His Glu Asp Asp Asp Glu Glu Leu Leu
    1025                1030                1035

Lys Arg Ser Glu Lys Leu Lys Arg Gln Met Arg Leu Arg Lys Tyr
    1040                1045                1050

Leu Glu Asp Glu Ala Glu Val Ser Gly Ser Asp Val Gly Ser Glu
    1055                1060                1065

Asp Glu Tyr Asp Gly Glu Glu Ile Asp Glu Tyr Glu Glu Asp Val
    1070                1075                1080

Ile Asp Glu Val Leu Pro Ser Asp Glu Glu Leu Gln Ser Gln Ile
    1085                1090                1095

Lys Lys Ile His Met Lys Thr Met Leu Asp Asp Asp Lys Arg Gln
    1100                1105                1110

Leu Arg Leu Tyr Gln Glu Arg Tyr Leu Ala Asp Gly Asp Leu His
    1115                1120                1125

Ser Asp Gly Pro Gly Arg Met Arg Lys Phe Arg Trp Lys Asn Ile
    1130                1135                1140

Asp Asp Ala Ser Gln Met Asp Leu Phe His Arg Asp Ser Asp Asp
    1145                1150                1155

Asp Gln Thr Glu Glu Gln Leu Asp Glu Ser Glu Ala Arg Trp Arg
    1160                1165                1170

Lys Glu Arg Ile Glu Arg Glu Gln Trp Leu Arg Asp Met Ala Gln
    1175                1180                1185

Gln Gly Lys Ile Thr Ala Glu Glu Glu Glu Ile Gly Glu Asp
    1190                1195                1200

Ser Gln Phe Met Ile Leu Ala Lys Lys Val Thr Ala Lys Ala Leu
    1205                1210                1215

Gln Lys Asn Ala Ser Arg Pro Met Val Ile Gln Glu Ser Lys Ser
    1220                1225                1230

Leu Leu Arg Asn Pro Phe Glu Ala Ile Arg Pro Gly Ser Ala Gln
    1235                1240                1245

Gln Val Lys Thr Gly Ser Leu Leu Asn Gln Pro Lys Ala Val Leu
    1250                1255                1260

Gln Lys Leu Ala Ala Leu Ser Asp His Asn Pro Ser Ala Pro Arg
    1265                1270                1275

Asn Ser Arg Asn Phe Val Phe His Thr Leu Ser Pro Val Lys Ala

```
                1280                1285                1290

Glu Ala Ala Lys Glu Ser Ser Lys Ser Gln Val Lys Lys Arg Gly
        1295                1300                1305

Pro Ser Phe Met Thr Ser Pro Ser Pro Lys His Leu Lys Thr Asp
        1310                1315                1320

Asp Ser Thr Ser Gly Leu Thr Arg Ser Ile Phe Lys Tyr Leu Glu
        1325                1330                1335

Ser

<210> SEQ ID NO 21
<211> LENGTH: 211
<212> TYPE: PRT
<213> ORGANISM: Homo sapiens
<220> FEATURE:
<221> NAME/KEY: MISC_FEATURE
<222> LOCATION: (1)..(211)
<223> OTHER INFORMATION: MAD2L2

<400> SEQUENCE: 21

Met Thr Thr Leu Thr Arg Gln Asp Leu Asn Phe Gly Gln Val Val Ala
1               5                   10                  15

Asp Val Leu Cys Glu Phe Leu Glu Val Ala Val His Leu Ile Leu Tyr
            20                  25                  30

Val Arg Glu Val Tyr Pro Val Gly Ile Phe Gln Lys Arg Lys Lys Tyr
        35                  40                  45

Asn Val Pro Val Gln Met Ser Cys His Pro Glu Leu Asn Gln Tyr Ile
    50                  55                  60

Gln Asp Thr Leu His Cys Val Lys Pro Leu Leu Glu Lys Asn Asp Val
65                  70                  75                  80

Glu Lys Val Val Val Ile Leu Asp Lys Glu His Arg Pro Val Glu
            85                  90                  95

Lys Phe Val Phe Glu Ile Thr Gln Pro Pro Leu Leu Ser Ile Ser Ser
        100                 105                 110

Asp Ser Leu Leu Ser His Val Glu Gln Leu Leu Arg Ala Phe Ile Leu
    115                 120                 125

Lys Ile Ser Val Cys Asp Ala Val Leu Asp His Asn Pro Pro Gly Cys
    130                 135                 140

Thr Phe Thr Val Leu Val His Thr Arg Glu Ala Ala Thr Arg Asn Met
145                 150                 155                 160

Glu Lys Ile Gln Val Ile Lys Asp Phe Pro Trp Ile Leu Ala Asp Glu
            165                 170                 175

Gln Asp Val His Met His Asp Pro Arg Leu Ile Pro Leu Lys Thr Met
        180                 185                 190

Thr Ser Asp Ile Leu Lys Met Gln Leu Tyr Val Glu Glu Arg Ala His
    195                 200                 205

Lys Gly Ser
    210

<210> SEQ ID NO 22
<211> LENGTH: 282
<212> TYPE: PRT
<213> ORGANISM: Homo sapiens
<220> FEATURE:
<221> NAME/KEY: MISC_FEATURE
<222> LOCATION: (1)..(282)
<223> OTHER INFORMATION: RAD1

<400> SEQUENCE: 22
```

Met Pro Leu Leu Thr Gln Gln Ile Gln Asp Glu Asp Gln Tyr Ser
1               5                   10                  15

Leu Val Ala Ser Leu Asp Asn Val Arg Asn Leu Ser Thr Ile Leu Lys
            20                  25                  30

Ala Ile His Phe Arg Glu His Ala Thr Cys Phe Ala Thr Lys Asn Gly
        35                  40                  45

Ile Lys Val Thr Val Glu Asn Ala Lys Cys Val Gln Ala Asn Ala Phe
    50                  55                  60

Ile Gln Ala Gly Ile Phe Gln Glu Phe Lys Val Gln Glu Glu Ser Val
65                  70                  75                  80

Thr Phe Arg Ile Asn Leu Thr Val Leu Leu Asp Cys Leu Ser Ile Phe
                85                  90                  95

Gly Ser Ser Pro Met Pro Gly Thr Leu Thr Ala Leu Arg Met Cys Tyr
            100                 105                 110

Gln Gly Tyr Gly Tyr Pro Leu Met Leu Phe Leu Glu Glu Gly Gly Val
        115                 120                 125

Val Thr Val Cys Lys Ile Asn Thr Gln Glu Pro Glu Glu Thr Leu Asp
    130                 135                 140

Phe Asp Phe Cys Ser Thr Asn Val Ile Asn Lys Ile Ile Leu Gln Ser
145                 150                 155                 160

Glu Gly Leu Arg Glu Ala Phe Ser Glu Leu Asp Met Thr Ser Glu Val
                165                 170                 175

Leu Gln Ile Thr Met Ser Pro Asp Lys Pro Tyr Phe Arg Leu Ser Thr
            180                 185                 190

Phe Gly Asn Ala Gly Ser Ser His Leu Asp Tyr Pro Lys Asp Ser Asp
        195                 200                 205

Leu Met Glu Ala Phe His Cys Asn Gln Thr Gln Val Asn Arg Tyr Lys
    210                 215                 220

Ile Ser Leu Leu Lys Pro Ser Thr Lys Ala Leu Val Leu Ser Cys Lys
225                 230                 235                 240

Val Ser Ile Arg Thr Asp Asn Arg Gly Phe Leu Ser Leu Gln Tyr Met
                245                 250                 255

Ile Arg Asn Glu Asp Gly Gln Ile Cys Phe Val Glu Tyr Tyr Cys Cys
            260                 265                 270

Pro Asp Glu Glu Val Pro Glu Ser Glu Ser
        275                 280

<210> SEQ ID NO 23
<211> LENGTH: 1208
<212> TYPE: PRT
<213> ORGANISM: Homo sapiens
<220> FEATURE:
<221> NAME/KEY: MISC_FEATURE
<222> LOCATION: (1)..(1208)
<223> OTHER INFORMATION: TIMELESS

<400> SEQUENCE: 23

Met Asp Leu His Met Met Asn Cys Glu Leu Leu Ala Thr Cys Ser Ala
1               5                   10                  15

Leu Gly Tyr Leu Glu Gly Asp Thr Tyr His Lys Glu Pro Asp Cys Leu
            20                  25                  30

Glu Ser Val Lys Asp Leu Ile Arg Tyr Leu Arg His Glu Asp Glu Thr
        35                  40                  45

Arg Asp Val Arg Gln Gln Leu Gly Ala Ala Gln Ile Leu Gln Ser Asp
    50                  55                  60

Leu Leu Pro Ile Leu Thr Gln His His Gln Asp Lys Pro Leu Phe Asp

```
            65                  70                  75                  80
Ala Val Ile Arg Leu Met Val Asn Leu Thr Gln Pro Ala Leu Leu Cys
                    85                  90                  95

Phe Gly Asn Leu Pro Lys Glu Pro Ser Phe Arg His His Phe Leu Gln
                100                 105                 110

Val Leu Thr Tyr Leu Gln Ala Tyr Lys Glu Ala Phe Ala Ser Glu Lys
                115                 120                 125

Ala Phe Gly Val Leu Ser Glu Thr Leu Tyr Glu Leu Leu Gln Leu Gly
            130                 135                 140

Trp Glu Glu Arg Gln Glu Glu Asp Asn Leu Leu Ile Glu Arg Ile Leu
145                 150                 155                 160

Leu Leu Val Arg Asn Ile Leu His Val Pro Ala Asp Leu Asp Gln Glu
                    165                 170                 175

Lys Lys Ile Asp Asp Asp Ala Ser Ala His Asp Gln Leu Leu Trp Ala
                180                 185                 190

Ile His Leu Ser Gly Leu Asp Asp Leu Leu Leu Phe Leu Ala Ser Ser
                195                 200                 205

Ser Ala Glu Glu Gln Trp Ser Leu His Val Leu Glu Ile Val Ser Leu
    210                 215                 220

Met Phe Arg Asp Gln Asn Pro Glu Gln Leu Ala Gly Val Gly Gln Gly
225                 230                 235                 240

Arg Leu Ala Gln Glu Arg Ser Ala Asp Phe Ala Glu Leu Glu Val Leu
                245                 250                 255

Arg Gln Arg Glu Met Ala Glu Lys Lys Thr Arg Ala Leu Gln Arg Gly
                260                 265                 270

Asn Arg His Ser Arg Phe Gly Gly Ser Tyr Ile Val Gln Gly Leu Lys
                275                 280                 285

Ser Ile Gly Glu Arg Asp Leu Ile Phe His Lys Gly Leu His Asn Leu
    290                 295                 300

Arg Asn Tyr Ser Ser Asp Leu Gly Lys Gln Pro Lys Lys Val Pro Lys
305                 310                 315                 320

Arg Arg Gln Ala Ala Arg Glu Leu Ser Ile Gln Arg Arg Ser Ala Leu
                325                 330                 335

Asn Val Arg Leu Phe Leu Arg Asp Phe Cys Ser Glu Phe Leu Glu Asn
                340                 345                 350

Cys Tyr Asn Arg Leu Met Gly Ser Val Lys Asp His Leu Leu Arg Glu
                355                 360                 365

Lys Ala Gln Gln His Asp Glu Thr Tyr Tyr Met Trp Ala Leu Ala Phe
    370                 375                 380

Phe Met Ala Phe Asn Arg Ala Ala Ser Phe Arg Pro Gly Leu Val Ser
385                 390                 395                 400

Glu Thr Leu Ser Val Arg Thr Phe His Phe Ile Glu Gln Asn Leu Thr
                405                 410                 415

Asn Tyr Tyr Glu Met Met Leu Thr Asp Arg Lys Glu Ala Ala Ser Trp
                420                 425                 430

Ala Arg Arg Met His Leu Ala Leu Lys Ala Tyr Gln Glu Leu Leu Ala
                435                 440                 445

Thr Val Asn Glu Met Asp Ile Ser Pro Asp Glu Ala Val Arg Glu Ser
    450                 455                 460

Ser Arg Ile Ile Lys Asn Asn Ile Phe Tyr Val Met Glu Tyr Arg Glu
465                 470                 475                 480

Leu Phe Leu Ala Leu Phe Arg Lys Phe Asp Glu Arg Cys Gln Pro Arg
                485                 490                 495
```

```
Ser Phe Leu Arg Asp Leu Val Glu Thr Thr His Leu Phe Leu Lys Met
            500                 505                 510

Leu Glu Arg Phe Cys Arg Ser Arg Gly Asn Leu Val Gln Asn Lys
        515                 520                 525

Gln Lys Lys Arg Lys Lys Lys Lys Val Leu Asp Gln Ala Ile
530                 535                 540

Val Ser Gly Asn Val Pro Ser Pro Glu Val Glu Ala Val Trp
545                 550                 555                 560

Pro Ala Leu Ala Glu Gln Leu Gln Cys Cys Ala Gln Asn Ser Glu Leu
                565                 570                 575

Ser Met Asp Ser Val Val Pro Phe Asp Ala Ala Ser Glu Val Pro Val
            580                 585                 590

Glu Glu Gln Arg Ala Glu Ala Met Val Arg Ile Gln Asp Cys Leu Leu
        595                 600                 605

Ala Gly Gln Ala Pro Gln Ala Leu Thr Leu Leu Arg Ser Ala Arg Glu
    610                 615                 620

Val Trp Pro Glu Gly Asp Val Phe Gly Ser Gln Asp Ile Ser Pro Glu
625                 630                 635                 640

Glu Glu Ile Gln Leu Leu Lys Gln Ile Leu Ser Ala Pro Leu Pro Arg
                645                 650                 655

Gln Gln Gly Pro Glu Glu Arg Gly Ala Glu Glu Glu Glu Glu Glu
            660                 665                 670

Glu Glu Glu Glu Glu Glu Leu Gln Val Val Gln Val Ser Glu Lys Glu
        675                 680                 685

Phe Asn Phe Leu Asp Tyr Leu Lys Arg Phe Ala Cys Ser Thr Val Val
    690                 695                 700

Arg Ala Tyr Val Leu Leu Leu Arg Ser Tyr Gln Gln Asn Ser Ala His
705                 710                 715                 720

Thr Asn His Cys Ile Val Lys Met Leu His Arg Leu Ala His Asp Leu
                725                 730                 735

Lys Met Glu Ala Leu Leu Phe Gln Leu Ser Val Phe Cys Leu Phe Asn
            740                 745                 750

Arg Leu Leu Ser Asp Pro Ala Ala Gly Ala Tyr Lys Glu Leu Val Thr
        755                 760                 765

Phe Ala Lys Tyr Ile Leu Gly Lys Phe Phe Ala Leu Ala Ala Val Asn
    770                 775                 780

Gln Lys Ala Phe Val Glu Leu Leu Phe Trp Lys Asn Thr Ala Val Val
785                 790                 795                 800

Arg Glu Met Thr Glu Gly Tyr Gly Ser Leu Asp Asp Arg Ser Ser Ser
                805                 810                 815

Arg Arg Ala Pro Thr Trp Ser Pro Glu Glu Glu Ala His Leu Arg Glu
            820                 825                 830

Leu Tyr Leu Ala Asn Lys Asp Val Glu Gly Gln Asp Val Val Glu Ala
        835                 840                 845

Ile Leu Ala His Leu Asn Thr Val Pro Arg Thr Arg Lys Gln Ile Ile
    850                 855                 860

His His Leu Val Gln Met Gly Leu Ala Asp Ser Val Lys Asp Phe Gln
865                 870                 875                 880

Arg Lys Gly Thr His Ile Val Leu Trp Thr Gly Asp Gln Glu Leu Glu
                885                 890                 895

Leu Gln Arg Leu Phe Glu Glu Phe Arg Asp Ser Asp Val Leu Gly
            900                 905                 910
```

His Ile Met Lys Asn Ile Thr Ala Lys Arg Ser Arg Ala Arg Ile Val
          915                 920                 925

Asp Lys Leu Leu Ala Leu Gly Leu Val Ala Glu Arg Arg Glu Leu Tyr
930                 935                 940

Lys Lys Arg Gln Lys Lys Leu Ala Ser Ser Ile Leu Pro Asn Gly Ala
945                 950                 955                 960

Glu Ser Leu Lys Asp Phe Cys Gln Glu Asp Leu Glu Glu Glu Glu Asn
              965                 970                 975

Leu Pro Glu Glu Asp Ser Glu Glu Glu Glu Gly Gly Ser Glu Ala
          980                 985                 990

Glu Gln Val Gln Gly Ser Leu Val Leu Ser Asn Glu Asn Leu Gly Gln
          995                 1000                1005

Ser Leu His Gln Glu Gly Phe Ser Ile Pro Leu Leu Trp Leu Gln
    1010                1015                1020

Asn Cys Leu Ile Arg Ala Ala Asp Asp Arg Glu Glu Asp Gly Cys
    1025                1030                1035

Ser Gln Ala Val Pro Leu Val Pro Leu Thr Glu Glu Asn Glu Glu
    1040                1045                1050

Ala Met Glu Asn Glu Gln Phe Gln Gln Leu Leu Arg Lys Leu Gly
    1055                1060                1065

Val Arg Pro Pro Ala Ser Gly Gln Glu Thr Phe Trp Arg Ile Pro
    1070                1075                1080

Ala Lys Leu Ser Pro Thr Gln Leu Arg Arg Ala Ala Ser Leu
    1085                1090                1095

Ser Gln Pro Glu Glu Gln Lys Leu Gln Pro Glu Leu Gln Pro
    1100                1105                1110

Lys Val Pro Gly Glu Gln Gly Ser Asp Glu Glu His Cys Lys Glu
    1115                1120                1125

His Arg Ala Gln Ala Leu Arg Ala Leu Leu Ala His Lys Lys
    1130                1135                1140

Lys Ala Gly Leu Ala Ser Pro Glu Glu Glu Asp Ala Val Gly Lys
    1145                1150                1155

Glu Pro Leu Lys Ala Ala Pro Lys Lys Arg Gln Leu Leu Asp Ser
    1160                1165                1170

Asp Glu Glu Gln Glu Glu Asp Glu Gly Arg Asn Arg Ala Pro Glu
    1175                1180                1185

Leu Gly Ala Pro Gly Ile Gln Lys Lys Lys Arg Tyr Gln Ile Glu
    1190                1195                1200

Asp Asp Glu Asp Asp
    1205

<210> SEQ ID NO 24
<211> LENGTH: 301
<212> TYPE: PRT
<213> ORGANISM: Homo sapiens
<220> FEATURE:
<221> NAME/KEY: MISC_FEATURE
<222> LOCATION: (1)..(301)
<223> OTHER INFORMATION: TIPIN

<400> SEQUENCE: 24

Met Leu Glu Pro Gln Glu Asn Gly Val Ile Asp Leu Pro Asp Tyr Glu
1               5                   10                  15

His Val Glu Asp Glu Thr Phe Pro Pro Phe Pro Pro Ala Ser Pro
            20                  25                  30

Glu Arg Gln Asp Gly Glu Gly Thr Glu Pro Asp Glu Glu Ser Gly Asn

```
                35                  40                  45
Gly Ala Pro Val Arg Val Pro Pro Lys Arg Thr Val Lys Arg Asn Ile
        50                  55                  60

Pro Lys Leu Asp Ala Gln Arg Leu Ile Ser Glu Arg Gly Leu Pro Ala
65                   70                  75                  80

Leu Arg His Val Phe Asp Lys Ala Lys Phe Lys Gly Lys Gly His Glu
                85                  90                  95

Ala Glu Asp Leu Lys Met Leu Ile Arg His Met Glu His Trp Ala His
                100                 105                 110

Arg Leu Phe Pro Lys Leu Gln Phe Glu Asp Phe Ile Asp Arg Val Glu
                115                 120                 125

Tyr Leu Gly Ser Lys Lys Glu Val Gln Thr Cys Leu Lys Arg Ile Arg
                130                 135                 140

Leu Asp Leu Pro Ile Leu His Glu Asp Phe Val Ser Asn Asn Asp Glu
145                 150                 155                 160

Val Ala Glu Asn Asn Glu His Asp Val Thr Ser Thr Glu Leu Asp Pro
                165                 170                 175

Phe Leu Thr Asn Leu Ser Glu Ser Glu Met Phe Ala Ser Glu Leu Ser
                180                 185                 190

Arg Ser Leu Thr Glu Glu Gln Gln Gln Arg Ile Glu Arg Asn Lys Gln
                195                 200                 205

Leu Ala Leu Glu Arg Arg Gln Ala Lys Leu Leu Ser Asn Ser Gln Thr
        210                 215                 220

Leu Gly Asn Asp Met Leu Met Asn Thr Pro Arg Ala His Thr Val Glu
225                 230                 235                 240

Glu Val Asn Thr Asp Glu Asp Gln Lys Glu Glu Ser Asn Gly Leu Asn
                245                 250                 255

Glu Asp Ile Leu Asp Asn Pro Cys Asn Asp Ala Ile Ala Asn Thr Leu
                260                 265                 270

Asn Glu Glu Glu Thr Leu Leu Asp Gln Ser Phe Lys Asn Val Gln Gln
                275                 280                 285

Gln Leu Asp Ala Thr Ser Arg Asn Ile Thr Glu Ala Arg
        290                 295                 300
```